United States Patent [19]

Aono et al.

[11] Patent Number: 5,300,639
[45] Date of Patent: Apr. 5, 1994

[54] THIAZOLO [5,4-B]AZEPINE COMPOUNDS

[75] Inventors: Tetsuya Aono, Nagaokakyo; Masahiro Suno, Kobe; Go Kito, Yao, all of Japan

[73] Assignee: Takeda Chemical Industries, Ltd., Osaka, Japan

[21] Appl. No.: 852,657

[22] Filed: Mar. 17, 1992

Related U.S. Application Data

[62] Division of Ser. No. 558,507, Jul. 27, 1990, Pat. No. 5,118,806, which is a division of Ser. No. 383,071, Jul. 21, 1989, Pat. No. 4,956,360.

[51] Int. Cl.$^5$ ............................................. C07D 223/12
[52] U.S. Cl. ................................................. 540/527
[58] Field of Search ........................................ 540/527

[56] References Cited

FOREIGN PATENT DOCUMENTS 53-121781 10/1978 Japan .
58-37097 3/1983 Japan .
63-283591 3/1987 Japan .

OTHER PUBLICATIONS

Potts Comprehensive Heterocyclic Chemistry 6. p. 302 (1984).

*Primary Examiner*—Robert Gerstl
*Attorney, Agent, or Firm*—Wegner, Cantor, Mueller & Player

[57] ABSTRACT

New thiazolo[5,4-b]azepine compounds represented by

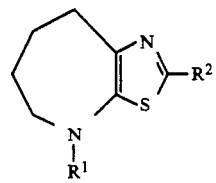

wherein $R^1$ is a hydrogen atom, an aliphatic group which may be substituted, a carboxylic acyl group which may be substituted or a sulfonic acyl group which may be substituted; $R^2$ is a hydrogen atom, an aromatic group which may be substituted or an aliphatic group which may be substituted, which are capable of e.g., inhibiting lipoperoxide formation.

11 Claims, No Drawings

THIAZOLO [5,4-B]AZEPINE COMPOUNDS

This application is a divisional of Ser. No. 07/558,507, filed Jul. 27, 1990, U.S. Pat. No. 5,118,806 which is a divisional of Ser. No. 07/383,071, filed Jul. 21, 1989, which issued as U.S. Pat. No. 4,956,360, on Sep. 11, 1990.

BACKGROUND OF THE INVENTION

1. Field of the Invention

The present invention relates to novel thiazolo[5,4-b]-azepine derivatives or salts thereof, and their manufacturing method and pharmaceutical compositions. More particularly, it provides a novel inhibitory agent for lipoperoxide formation or lipoxygenase which is useful in the prevention or treatment of various diseases such as cancers, arteriosclerosis, hepatic diseases, cerebrovascular diseases, inflammation or the like.

2. Description of the Prior Art

The formation of lipoperoxide in the living body and its accompanying radical reactions have been proven to have various ill effects in the living body causing various membrane and enzyme disorders. Accordingly, the application of antioxidative lipoperoxide formation inhibitors as medicines has been attempted. However, most lipoperoxide formation inhibitors used in the art at present are derivatives of natural antioxidants such as vitamin C or vitamin E, and phenol derivatives, and accordingly have not been satisfactory for practical use. In order to utilize lipoperoxide formation inhibitors widely in medicinal fields, the development of lipoperoxide formation inhibitors having new chemical structures has been required. The main object of the present invention is to provide new compounds which are capable of inhibiting lipoperoxide formation.

SUMMARY OF THE INVENTION

In order to solve the above mentioned problem, the inventors of the present invention synthesized many new compounds and examined their inhibitory action on lipoperoxide formation.

Thus, we succeeded in the creation of thiazolo [5,4-b] azepine derivatives having a new chemical structure of the formula (I):

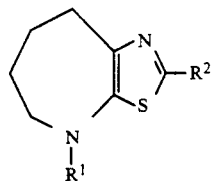

[I]

wherein $R^1$ is a hydrogen atom, an aliphatic group which may be substituted, or a carboxylic acyl or sulfonic acyl group which may be substituted; $R^2$ is a hydrogen atom or an aromatic or aliphatic group which may be substituted. This class of compounds was found to possess action useful as medicines, such as potent inhibitory action on lipoperoxide formation, inhibitory or supressive action on 12-hydroxy heptadecatrienoic acid (hereinafter abbrebiated as HHT) and lipoxygenase and/or antagonistic action on leukotriene D4 (LTD4)-acceptor.

According to the present invention, it provides new thiazolo[5,4-b]azepine derivatives of the above mentioned formula (I) and salts thereof, their manufacturing method and pharmaceutical composition containing said compound as the active ingredient.

PREFERRED EMBODIMENTS OF THE INVENTION

In the formula (I), the aliphatic group which may be substituted represented by $R^1$ may be saturated or unsaturated and includes a straight, branched or cyclic alkyl group as the saturated group and a straight or branched alkenyl and alkynyl group as the unsaturated group. The alkyl group is suitably a lower alkyl group containing 1 to 6 carbon atoms, e.g., methyl, ethyl, propyl, i-propyl, butyl, i-butyl, t-butyl, pentyl, hexyl, cyclopropyl, cyclobutyl or cyclopentyl. The alkenyl group is suitably a lower alkenyl group containing 2 to 6 carbon atoms, e.g., vinyl, allyl, propenyl, i-propenyl, 2-butenyl, 2,4-butadienyl, 1,3-butadienyl, 2-pentenyl or 2,4-pentadienyl. The alkynyl group represented by $R^1$ is preferably a lower alkynyl having 2 to 6 carbon atoms, e.g. ethynyl or 2-propynyl.

Substituents on the aliphatic groups which may be substituted are not particularly limited but normally could be conventional ones used in the pharmaceutical field. Examples of the substituents are hydroxy; a $C_{1-3}$ alkoxy such as methoxy, ethoxy, n-propoxy or i-propoxy (thus forming e.g., methoxymethyl or 1-ethoxyethyl); an aryloxy such as phenoxy or naphthoxy; a phenylalkoxy such as benzyloxy or phenethyloxy; mercapto; a $C_{1-3}$ alkylthio such as methylthio or ethylthio; an arylthio such as phenylthio or naphthylthio; a phenylalkylthio such as benzylthio or phenethylthio; amino (forming e.g. 2-aminoethyl); a mono- or di- $C_{1-3}$ alkylamino such as methylamino, ethylamino or dimethylamino; a halogen such as chlorine or bromine (forming e.g., 2-bromoethyl); an esterified carboxyl such as $C_{2-4}$ alkoxycarbonyl (e.g., methoxycarbonyl or ethoxycarbonyl) or benzyloxycarbonyl; a $C_{2-4}$ alkoxycarbonyloxy; formyl; an alkanoyl such as acetyl or propionyl, or benzoyl; an alkanoyloxy such as acetoxy, propionyloxy or pivaloyloxy, or benzoyloxy; cyano; phthalimido; an alkanoylamino such as acetamido, or benzamido; a $C_{2-5}$ alkoxycarbonylamino such as methoxycarbonylamino or ethoxycarbonylamino; a phenylalkoxycarbonylamino such as benzyloxycarbonylamino; a cyclic amino such as pyrrodino morpholino; carboxyl; and carbamoyl (these groups being hereinafter called as Group A).

Among the group in Group A, particularly preferred are carboxyl, an esterified carboxyl, carbamoyl and a $C_{1-3}$ alkylamino groups.

The sulfonic acyl group which may be substituted represented by $R_1$ may be a $C_{1-3}$ alkyl sulfonyl such as methanesulfonyl, ethanesulfonyl or propanesulfonyl, or phenylsulfonyl. The alkyl sulfonyl group may possess substituent(s) selected from the above Group A. The preferred substituents are mono- or di-$C_{1-3}$ alkyl amino such as dimethylamino or diethylamino. In the case of phenylsulfonyl as $R^1$ having substituents(s) on the phenyl ring, examples of these substituents are a halogen; nitro; an amino (which may be substituted by a $C_{1-3}$ alkyl, a $C_{2-4}$ alkenyl, a $C_{3-8}$ cycloalkyl or phenyl); sulfo; mercapto; hydroxy; sulfoxy; sulfamoyl; a $C_{1-6}$ alkyl (which may be substituted by amino, a di $C_{1-3}$ alkylamino; a mono $C_{1-3}$ alkylamino, a halogen, hydroxy, cyano or carboxy); a $C_{1-6}$ alkoxy (which may be substituted by a $C_{1-3}$ alkylthio); benzyloxy; a $C_{1-3}$ alkylthio; a $C_{1-3}$ alkylsulfonamido; an amidino (which may be substituted by a $C_{1-3}$ alkyl and benzyl); methylenedioxy; alkoxy formimidoyl; a $C_{1-3}$ alkylsulfonyl; a $C_{1-3}$ alkylsulfonylamino; an esterified carboxy such as a $C_{2-4}$ alkoxycarbonyl (especially methoxycarbonyl or ethoxycarbonyl) or benzyloxycarbonyl; formyl; an alkanoyl such as acetyl or propionyl, or benzoyl; an alkanoyloxy such as acetoxy, propionyloxy or pivaloyloxy; cyano; phthalimido; an alkanoylamino such as acetamido, or benzamido; a $C_{2-4}$ alkoxycarbonylamino such as methoxycarbonylamino or ethoxycarbonylamino; a phenylalkoxycarbonylamino such as benzyloxycarbonylamino; a cyclic amino such as pyrolidino or morpholino; carboxy; carbamoyl or phenyl which may be substituted by a halogen, methoxy $C_{1-3}$ alkyl and the like (these substituents are hereinafter called as Group P). Among these substituents, preferred is hydroxy, a $C_{1-6}$ alkoxy, a $C_{1-6}$ alkyl, a halogen, nitro, amino, a mono- or di-($C_{1-6}$ alkyl) amino, a $C_{1-6}$ alkylthio, a $C_{1-6}$ alkoxycarbonyl, a $C_{1-6}$ alkoxycarbonyloxy, amidino, an amino-$C_{1-6}$ alkyl, cyano, phenyl, phenylamino or an alkoxyformimidoyl. Particularly, methyl, methoxy, chlorine, fluorine, amino or a mono- or di-($C_{1-6}$ alkyl) amino is preferable.

Also, the carboxylic acyl group which may be substituted represented by $R_1$ may be a group of the formula : $R^3CO$—in which $R^3$ is a saturated or unsaturated aliphatic group which may be substituted or an aromatic group which may be substituted.

The aromatic group of $R^3$ includes an aromatic carbocyclic group and an aromatic heterocyclic group. Examples of the aromatic carbocyclic groups are phenyl and naphthyl. Preferable examples of the aromatic heterocyclic groups are 5 to 6 membered aromatic heterocyclic groups containing 1 to 4 (preferably 1 or 2) of hetero atoms such as nitrogen, oxygen and sulfur atoms. Specifically, the aromatic heterocyclic group may be pyridyl, furyl, thienyl, pyrazinyl, oxazolyl, thiazolyl, pyrrolyl, imidazolyl or isoxazolyl, without limitation thereof. Other preferred examples include aromatic groups condensed with an aromatic heterocyclic or carbocyclic ring. As these condensed aromatic groups, mention is made of, for example, indolyl, quinolyl, benzimidazolyl, imidazopyridyl and thiazolopyridyl.

Examples of substituents on the aromatic carbocyclic groups are groups selected from the above mentioned Group P. Examples of substituents on the aromatic heterocyclic group are an amino (optionally possessing substituent(s) such as a $C_{2-10}$ alkanoyl, benzoyl, a halogen substituted $C_{2-4}$ alkanoyl, phenyl or a $C_{1-3}$ alkyl), a halogen, nitro, sulfo, cyano, hydroxy, carboxy, oxo, a $C_{1-10}$ alkyl (optionally possessing substituent(s) such as phenyl, a halogen, amino, hydroxy, carboxy, a $C_{1-3}$ alkoxy, a $C_{1-3}$ alkylsulfonyl or a $C_{1-3}$ dialkylamino), a $C_{3-6}$ cycloalkyl, a $C_{1-3}$ alkoxy, a $C_{2-10}$ alkanoyl, benzoyl, a phenyl (optionally possessing substituent(s) such as a halogen, nitro, an alkyl, an alkoxy, amino, sulfo, hydroxy or cyano), oxo or a $C_{1-10}$ alkylthio (optionally possessing substituent(s) such as phenyl, a halogen, amino, hydroxy, carboxy, a $C_{1-3}$ alkoxy, a $C_{1-3}$ alkylsulfonyl or a di-$C_{1-3}$ alkylamino) (these substituents being hereinafter called as Group H). Among the groups in Group H, particularly preferred are $C_{1-10}$ alkyls, amino, mono- or di-($C_{1-3}$ alkyl) amino and halogens.

Among the groups in Group H, particularly preferred are $C_{1-10}$ alkyls, amino, mono- or di-($C_{1-3}$ alkyl) amino and halogens.

The aliphatic group of $R^3$ may be one which is either saturated or unsaturated, e.g., alkyl, alkenyl and alkynyl groups. The alkyl group includes the lower alkyl as mentioned above and a higher alkyl group containing 7 or more carbon atoms, such as heptyl, octyl, nonyl, decyl, undecyl, dodecyl, heptadecyl or octadecyl. The alkyl group of $R^3$ is preferably an alkyl group containing 1-18 carbon atoms. As the alkenyl group and alkynyl group represented by $R^3$, preferred are the alkenyl and alkynyl groups as mentioned above for $R^1$. The carbon number of the alkenyl group and alkynyl group is preferably 2-4.

Examples of substituents on the saturated or unsaturated aliphatic groups of $R^3$ are the groups belonging to the above mentioned Group A; a phenyl group which may be substituted by substituent(s) selected from the Group P as mentioned above; a phenethylamino or benzylamino group optionally having on its ring substituent(s) selected from the above mentioned Group P; and a heterocyclic group which may be substituted by substituent(s) selected from the above mentioned Group H. The heterocyclic groups include partially or totally saturated heterocyclic groups(e.g., morpholino, piperidinyl, piperidino, piperazinyl or pyrrolidinyl), in addition to the aromatic heterocyclic groups mentioned in the aromatic group of $R^3$.

The aliphatic groups of $R^2$ include the saturated or unsaturated aliphatic groups as described with respect to $R^1$. Further, the unsaturated aliphatic groups include not only the lower alkenyl or alkynyl groups as described with respect to $R^1$ mentioned above but also those having 7-10 carbon atoms. Preferably, the aliphatic group of $R^2$ is a group of the formula $R^4X$ ($R^4$ is an aromatic group which may be substituted and X is an unsaturated aliphatic group being capable of conjugating the thiazole ring in the thiazoloazepine ring and $R^4$). Examples of the groups of the formula $R^4X$ are alkenyl or alkynyl groups substituted by a phenyl optionally having substituent(s) selected from the Group P or possessing an oxo group.

The aromatic groups of $R^2$ include the aromatic carbocyclic or aromatic heterocyclic groups or their condensed aromatic groups as described with respect to $R^3$. Examples of substituents on the aromatic carbocyclic group are groups selected from the Group P and examples of substituents on the aromatic heterocyclic group are groups selected from the Group H.

The number of substituents in the groups which may be substituted for $R^1$ and $R^2$ is 1-5, preferably 1-3.

With respect to $R^1$, preferred compounds of the formula (I) are compounds where $R^1$ is a hydrogen atom or a carboxylic acyl (preferably acetyl or propionyl which may be substituted on the methyl or ethyl moiety). Particularly, preferred are compounds of the formula (I) wherein $R^1$ is a hydrogen atom. With respect to $R^2$, preferred are compounds of the formula (I) wherein $R^2$ is a phenyl, an aromatic heterocyclic group, or an alkenyl which may also be substituted by an aromatic groups. Preferred are compounds of the formula (I) in which the aliphatic group which may be substituted for $R^2$ is a group of the formula : $R^4 X$ wherein $R^4$ is an aromatic group which may be substituted and X is an unsaturated aliphatic group being capable of conjugating the thiazole ring in the thiazoloazepine ring and $R^4$. More preferred ones are those where $R^1$ is hydrogen atom and $R^2$ is a phenyl, an aromatic heterocyclic group, or a $C_{2-4}$ alkenyl which may be substituted by phenyl, thienyl, furyl, pyridyl, pyrazinyl or imidazolyl, which is conjugated with the thiazo ring. Most preferably, $R^2$ is a vinyl or butadienyl substituted by a phenyl or an aromatic heterocyclic group which may be substituted.

Besides, the compounds of the formula (I) may form their stereoisomers depending upon the kind of the substituents $R^1$ and $R^2$. The present invention intends to include a single form of such stereoisomers as well as a mixture thereof.

The salts of the compounds of the formula (I) are preferably the pharmaceutically acceptable salts, e.g., salts with an inorganic acid such as hydrogen halide (e.g., hydrogen chloride or hydrogen bromide), phosphoric acid or sulfuric acid; or an organic acid such as an organic carboxylic acid (e.g., oxalic acid, phthalic acid, fumaric acid or maleic acid) or a sulfonic acid (e.g., methanesulfonic acid or benzenesulfonic acid). When the compounds (I) possess an acidic group such as a carboxyl group, it can form its salt with an inorganic base such as an alkali metal (e.g., sodium or potassium) or alkali earth metal (e.g., magnesium) compound, or with an organic base such as an amine (e.g., dicyclohexylamine, triethylamine or 2,6-lutidine).

The compound of the formula (I) and its salt are hereinafter stated by a general term of the compound (I).

The compound (I) of the present invention can be prepared e.g., by the method illustrated by Chart-I.

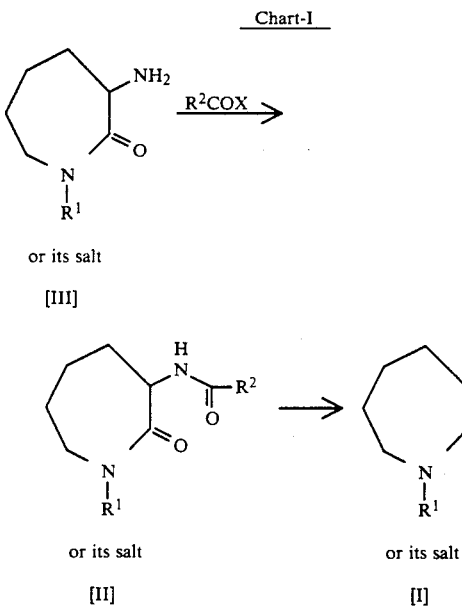

Chart-I

In Chart-I, $R^1$ and $R^2$ have the same meanings as defined above and $R^2$COX is a reactive derivative of a carboxylic acid.

That is, the compound (III) or salt thereof (the salt of the compound (I) as mentioned above being applicable) is acylated with a reactive derivative of a carboxylic acid having the formula : $R^2$COX to yield the compound (II), which then is treated with a thiation agent to obtain the compound (I). More specifically, the reactive derivative of $R^2$COX may be an acid chloride, acid bromide, imidazolide, acid anhydride, acid azide, N-phthalimido ester or N-oxysuccinimido ester. Instead of using the above active ester, a carboxylic acid having the formula : $R^2$COOH may be caused to react directly with the compound (III) in the presence of a coupling agent such as N,N-dicyclohexylcarbodimide (sometimes abbreviated as DCC).

The reactive derivative of $R^2$COX is used in about 1-3 mols, preferably about 1-1.2 mols, to one mol of the compound (III). On the other hand, the carboxylic acid of the formula $R^2$COOH is used in about 1-3 mols, preferably about 1-1.2 mols in the presence of about 1-1.2 mols of the coupling agent, based upon one mol of the compound (III).

The reaction will proceed smoothly generally at a temperature range extending from the temperature of cooling ice to room temperature (room temperature used here and hereinafter in the explanation of the preparation method refers specifically to the temperature range 5°-35° C.). Solvents employed may be any inert solvents and there are no particular limitations. Chloroform, methylene chloride, tetrahydrofuran, dioxane or dimethylformamide is frequently used. When an acid chloride or acid bromide is used as the acylating agent, it is preferable to add an amine such as triethylamine or pyridine in the reaction system. The reaction time is generally between 30 minutes to 12 hours, depending upon the reagent, solvent and temperature to be adopted.

The reaction of converting the compound (II) into the compound (I) is conducted in the presence of a thiation agent such as phosphorus pentasulfide or Lawesson's reagent. The amount of the thiation agent to be employed is generally about 1-3 mols, or preferably an amount which is equivalent to one mol of the compound (II). The reaction solvent is preferably pyridine, but is not limited to pyridine. The reaction is conducted at a temperature of about 50°-120° C., preferably at about 80°-120° C. The reaction time depends mainly upon the reaction temperature, but is generally between 3-12 hours, for example, approximately 5 hours at about 100°-120° C.

In Chart-I, the substituent of $R^1$ may be converted to another substituent of $R^1$ at any stage in the process. However, it is generally advantageous to convert only after the formation of the compound (I). Typical examples of the conversion reaction of $R^1$ is to subject a compound wherein $R^1$ is a hydrogen atom to an alkylation, sulfonation or acylation thus creating the object compound wherein $R^1$ is an alkyl, sulfonic acyl or carboxylic acyl group which may be substituted.

These reactions may be conducted in accordance with the methods known per se, but also by the following methods.

The conversion of $R^1$ in the compound (I) from being a hydrogen atom hereinafter sometimes abbreviated as the compound (I) ($R^1$=H) into $R^1$ which is an acyl group is achieved through an acylation of the compound (I) ($R^1$=H). For obtaining $R^1$ being carboxylic acyl, a reactive derivative of a desired carboxylic acyl is caused to react with the compound (I) ($R^1$=H). The kind of the reactive derivatives and the reaction conditions mentioned in the reaction from the compound (III) into the compound (II) are generally those applicable for that in the above acylation. Under such conditions, the acylation will proceed smoothly. In order to convert the compound (I) ($R^1$=H) into the compound (I) of $R^1$ which is a sulfonic acyl, it is convenient to cause a reaction of the compound (I) ($R^1$=H) with a halogenated sulfonyl. This reaction is usually conducted in the presence of an amine such as triethylamine or pyridine. The reaction may be conducted using any inert solvent, preferably acetone, dioxane, dimethylformamide, tetrahydrofuran, chloroform or methylenechloride. Under certain circumstances, pyridine may be used as the solvent. The reaction will proceed smoothly at 0° C. to room temperature and will be completed in 30 minutes to 5 hours. In the above reaction, about 1-3 mols of the amine and about 1-2 mols of the acylation agent are used for one mol of the compoud (I).

In order to obtain the compound (I) where $R^1$ is an alkyl, the compound (I) ($R^1=H$) is subjected to an alkylation. Examples of the alkylating agents are halogenated alkyls (halogen being chlorine, bromine or iodine) and sulfonic acid alkyl esters (e.g., p-toluenesulfonic acid alkylester or methanesulfonic acid alkyl ester). The alkylating agent is used in a proportion of about 1-2 mol, to one mol of the compound (I). The reaction is usually conducted in the presence of an inorganic base such as potassium carbonate or sodium carbonate, or an organic base such as triethylamine or pyridine. It is desirable that the amount of base used is equivalent to the amount of the alkylating agent. The solvent may be suitably tetrahydrofuran, dioxane, dimethylformamide or dimethylacetamide, without particular limitation thereof. The reaction is usually conducted under heating, suitably at about 30° C–100° C.

The compound (I) where $R^1$ is alkyl can also be obtained by reducing the compound (I) where $R^1$ is a carboxylic acyl. The reduction can be conducted in accordance with conventional methods, but is suitably conducted by use of a reducing agent such as lithium aluminum hydride or diborane. Such solvent as tetrahydrofuran or dioxane is used and the reaction will usually proceed under refluxing.

Furthermore, the compound (III) where $R^1$ is a hydrogen atom as the starting material in the preparation method of the present invention is known and the compounds (III) where $R^1$ are groups other than a hydrogen atom can be synthesized in accordance with, e.g., J. P. Snyder et al's method, *J. Med. Chem.* 29, 251 (1986), as shown by Chart-II.

Chart-II

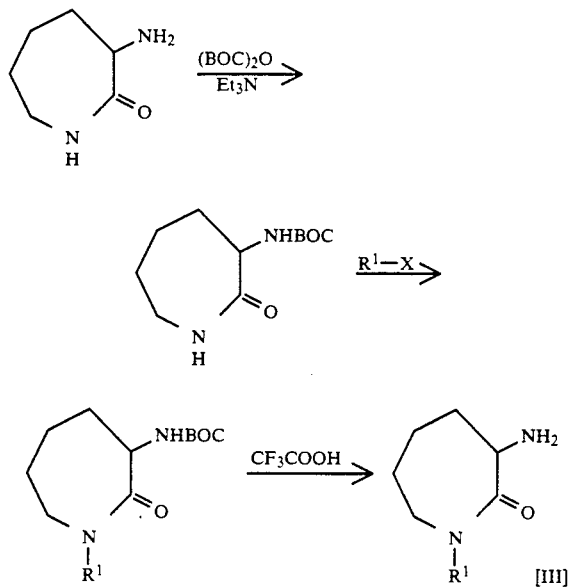

In the formulae, $R^1$ has the same meaning as defined before, X is a halogen atom and BOC stands for tert-butoxycarbonyl group.

Also, the compound (III) may be prepared from the corresponding compound of $R^1$ being a hydrogen atom in accordance with the conversion reactions of $R^1$ moiety in the compound (I) into other $R^1$ moieties as mentioned above.

Some of the compounds (I) can be produced also by a known method or a method analogous thereto. The compound (I) as obtained by the above methods may be isolated and purified by conventional separation means such as recrystallization, distillation or chromatography. The resulting compound (I) in free form can be converted into the corresponding salt in accordance with the method known per se, e.g., neutralization reaction. Alternatively, the compound (I) in salt form may be converted into the free form in accordance with the conventional method.

The compounds (I) of the present invention possess improving actions on the circulatory system and antiallergic action, such as improving the metabolism of polyunsaturated fatty acids (e.g., linoleic acid, γ-linolenic acid, γ-linolenic acid, arachidonic acid, di-homo-γ-linolenic acid or eicosapentalnoic acid), especially inhibitory action on the formation of lipoperoxide (antioxydative action), inhibitory action on the formation of 5-lipoxygenase metabolites (e.g., leucotrienes, 5-hydroperoxyeicosatetraenoic acid (HPETE), 5-hydroxyeicosatetraenenoic acid (HETE), lipoxins or leukotoxins), inhibitory action for thromboxane $A_2$ synthetic enzyme, promoting action for prostaglandin $I_2$ synthetic enzyme, antagonistic action for $LTD_4$ acceptor or eliminating action for active oxygen species. Among these actions, the compounds (I) tend to exert remarkable inhibitory action on the formation of lipoperoxide (i.e., antioxydative action).

The compounds (I) have low toxicity and side effects.

Accordingly, the compound (I) is effective for treating or preventing the following diseases in mammals (mouse, rat, rabbit, dog, monkey and man): Thrombosis caused by platelet aggregation, ischemic diseases caused by smooth muscle-contraction or vasospasm of arterial vessels of the heart, lung, brain and kidney (e.g., cardiac infarction cerebral apoplexy), neuronal degeneration (e.g., Parkinson's disease, Alzheimer's disease, Lou-Gehrig's diseases or muscular dystrophy), functional, memory and emotional disorders caused by damage to the central nervous system such as head or spinal injuries (disturbances due to necrosis of nerve cells induced by oxygen deficiency, brain damage, cerebral apoplexy, cerebral infarction or cerebral thrombosis), seizure and epilepsy after cerebral apoplexy, cerebral infarction, cerebral surgery and head injury, nephritis, pulmonary insufficiency, bronchial asthma, inflammation, arteriosclerosis, atherosclerosis, hepatitis, acute hepatitis, liver cirrhosis, hypersensitive pneumonitis, immunodeficiency, circulatory diseases (myocardial infarction, cerebral apoplexy, cerebral edema, nephritis and so on) induced by disturbances of enzyme, tissues or cells which are caused by active oxygen species (e.g., superoxide or hydroxy radical), and other diseases such as tissue-fibrogenesis or cancer. Thus, it is useful as medicine, e.g., antithrombogenic agent, anti-angiospastic agent, anti-asthmatic agent, anti-allergic agent, agent for improving circulatory organs such as heart and brain, agent for improving nephritis and hepatitis, inhibitor for tissue-fibrogenesis, agent for eliminationg active oxygen species or as an agent for controlling and improving arachidonate cascade.

The compound (I) may be safely administered through oral or parenteral routes as it is or in its pharmaceutical composition mixed with a pharmaceutically acceptable carrier or excipient, or the like (e.g., tablets, capsules, liquids, injections or suppository). The dosage depends upon subjects, routes and symptoms. However, for example, its oral dosage for adult patients suffering from circulatory diseases is usually about 0.1-20 mg/kg body weight/once, preferably about 0.2-10 mg/kg body weight given once to three times a day.

It will be understood that the compounds (I) possess inhibitory action for the formation of lipoperoxide (antioxidating action) and inhibitory action for the formation of of lipoxygenase metabolites, and HHT as illustrated by the following tests and hence are useful as medicines for treating or preventing circulatory diseases, inflammation or allergic diseases.

The compound (I) of the invention (I) has, as shown in the following test examples, inhibitory action for the formation of lipoperoxide, antioxidative action, and inhibitory actions for lipoxygenase and the formation of HHT, being useful as medicine for treatment or prevention of circulatory diseases, inflammation and allergic diseases.

Test examples, examples and reference examples are described in the following. The invention is not limited to these examples.

TEST EXAMPLE 1

Inhibitory Action on 5-lipoxygenase

RBL-1 cells (rat basophilic leukemia cells) of $10^7$ were suspended in 0.9 ml of MCM (mast cell medium). To the suspension was added the test solution (the final concentration of 10 $\mu$M, 1 $\mu$M and 0.1 $\mu$M) prepared in advance. The mixture was incubated at 37° C. for 5 minutes. Then, 0.1 ml of MCM containing 50 $\mu$g of arachidonic acid and 10 $\mu$g of calcium ionophore A-23187 was added and further the mixture was incubated at 37° C. for 15 minutes. After the reaction, 1 ml of ethanol was added, well shaken and subjected to high performance liquid chromatography to determine 5-HETE. The absorption at 240 nm due to 5-HETE was measured by an ultraviolet abosorption monitor. The inhibition rate of 5HETE formation calculated from the peak area is shown in Table 1.

The inhibition rate of 5-HETE formation is represented by $(1-b/a) \times 100$, wherein a is the peak height or area in the absence of the compound (I) and b is that in the presence of the compound (I).

TABLE 1

| Compound Example No. | Inhibition rate (%) | | |
|---|---|---|---|
| | $10^{-6}$* | $10^{-7}$* | $10^{-8}$* |
| 9 | 100 | 79 | 12 |
| 2 | 100 | 56 | 14 |
| 28 | 95 | 56 | 9 |
| 22 | 100 | 49 | 4 |
| 20 | 100 | 44 | 2 |
| 24 | 93 | 53 | 26 |

*Concentration of test compound (M)

By the above results, the compounds of the invention are proved to inhibit lipoxygenase even at low concentration and also to inhibit the formation of 5-HETE.

TEST EXAMPLE 2

Inhibitory Action for the Formation of HHT (12-hydroxyheptadeca-5,8,10-trienoic acid) in Rat's Platelet Eight ml of blood was gathered from the abdominal aorta of a rat (JcI : Wistar, male, 12-15 weeks age) subjected to abdominal incision under anesthesia by the use of 3.2 % sodium citrate (1 volume of sodium citrate solution to 9 volume of whole blood). The blood was centrifuged at 800 rpm for 10 minutes at room temperature to gather PRP (platelet rich plasma), and the residual blood was further centrifuged at 3000 rpm for 10 minutes to gather PPP (platelet poor plasma). The platelet number in PRP was measured and the PRP was adjusted by diluting with PPP so that the concentration of platelet was one million/$\mu$l. To 0.25 ml of the PRP, 125 $\mu$g of arachidonic acid and the test compound (the final concentration of 100 $\mu$M, 10 $\mu$M, 1 $\mu$M and 0.1 $\mu$M) were added, and the mixture was incubated at 37° C. for 15 minutes. After the reaction, 1.1 ml of ethanol was added, well shaken and centrifuged at 2000 rpm for 10 minutes to separate the supernatant. To 1 ml of the supernatant 1 ml of water was added and subjected to high performance liquid chromatography to determine HHT. The absorption at 240 nm due to HHT was measured by an ultraviolet absorption monitor. The inhibition rate of HHT formation calculated from the peak area is shown in Table 2.

The inhibition rate of HETE formation is represented by $(1-b/a) \times 100$, wherein a is the peak height or area in the absence of the compound (I) and b is that in the presence of the compound (I).

TABLE 2

| Compound Example No. | Inhibition rate (%) | | |
|---|---|---|---|
| | $10^{-4}$* | $10^{-5}$* | $10^{-6}$* |
| 41 | 87 | 63 | 23 |
| 3 | 100 | 83 | 22 |
| 26 | 100 | 63 | 22 |
| 31 | 100 | 80 | 19 |
| 20 | 96 | 43 | 18 |
| 2 | 100 | 58 | 16 |

*Concentration of test compound (M)

TEST EXAMPLE 3

Inhibitory Action for Lipoperoxide Formation in Rat's Brain Homogenate

According to the method by Suno et al. (*Japan J. Pharmacol.*, 35, 196(1984) , the concentration of the compound necessary for 50% inhibition of lipoperoxide formation in rat's brain homogenate was determined by examining the lipoperoxide formation using the thiobarbituric acid method. The results obtained are shown in Table 3.

TABLE 3

| Compounds Example No. | $IC_{50}$ (M) $\times 10^{-7}$ |
|---|---|
| 28 | 7 |
| 23 | 12 |
| 26 | 12 |
| 21 | 7 |
| 6 | 7 |
| 9 | 7 |
| 12 | 6 |
| 7 | 8 |

TABLE 3-continued

| Compounds Example No. | $IC_{50}(M) \times 10^{-7}$ |
|---|---|
| 8 | 7 |

From the above results, the compounds of the invention proved to have an excellent inhibitory action for lipoperoxide formation.

TEST EXAMPLE 4

Action of the Drug on Behavior Change due to the Spinal Intrathecal Injection (i.t.) of Ferrous Chloride in Mice In male Slc : ICR mouse of 5 weeks age 10 mice per group were used. After 5 µl/mouse of saline dissolved 50 mM of ferrous chloride was intrathecally injected from the 6th lumbar segment to the 1st sacral segment, the mouse's behavior was observed for 15 minutes to an hour. The evaluation point of behavior change was scored according to the following criterion.

| Evaluation point | Behavior change |
|---|---|
| 0 | Normal |
| 1 | Repeated bites on the legs and abdomen |
| 2 | a) Violent bites on the abdomen sometimes tumbling about. |
|   | b) Sensitive response to external stimulus and aggressiveness |
|   | c) Tremor |
| 3 | Clonus |
| 4 | Tetanus or paralysis in uni- or bi-lateral leg |
| 5 | Death |

The inhibition rate was shown based on the evaluation point under the above criterion. The test compound was orally administered 30 minutes before the i.t. injection of ferrous chloride.

Table 4 shows the average score and inhibition rate when 100 mg/kg of the compound (I) was orally administered.

TABLE 4

| Compound Example No. | Average score | | Inhibition rate (%) |
|---|---|---|---|
| | 100 mg/kg dose | saline dose | |
| 21 | 1.7 | 4.6 | 63.0 |
| 2 | 1.2 | 4.7 | 74.5 |
| 16 | 0.3 | 5.0 | 94.0 |
| 5 | 0.9 | 5.0 | 82.0 |
| 28 | 1.1 | 4.7 | 76.6 |

From the above results, the compounds of the invention are proved to have an excellent inhibitory action on the central nervous disorders accompanied by lipoperoxide formation due to ferrous chloride

TEST EXAMPLE 5

Leukotriene $D_4$ ($LTD_4$) Receptor Antagonism.

According to the method by S. S. Pong , and R. N. DeHaven (*Proceedings of the National Academy of Sciences of the United States of America*, 80, 7415–7419 (1983) , the leukotriene $D_4$($LTD_4$) receptor antagonism was measured by using [$^3$H]$LTD_4$ and guinea pigs' lung membrane fraction. The results are shown in Table 5.

TABLE 5

| Compound Example No. | Inhibition rate (%) | | |
|---|---|---|---|
| | $10^{-6}$* | $10^{-7}$* | $10^{-8}$* |
| 30 | 100 | 98.8 | 76.0 |
| 6 | 100 | 94.3 | 64.4 |
| 8 | 94.6 | 92.4 | 54.8 |
| 13 | 100 | 92.5 | 61.0 |

*Concentration of test compound (M)

From the above results, the compounds of the invention are proved to have excellent $LTD_4$ receptor antagonism.

TEST EXAMPLE 6

Effect on Cerebral Blood Flow after complete Cerebral Ischemia-Reperfusion in Dogs Fourteen adult mongrel dogs were anesthetized with a combination of α-chloralose and urethane. Polyethylene catheters were introduced into the femoral artery and vein. Systemic blood pressure was measured through the cannulated femoral artery with an electromanometer. Heart rate was recorded with a cardiotachometer. The regional cerebral blood flow ($\gamma$-CBF) was measured using a thermal diffusion flow probe incorporating a Peltier stack. The animals were subjected to positive-pressure ventilation with room-air. A thoracotomy was performed in the third right intercostal space. The ligatures were loosely placed around the ascending aorta, inferior vena cava, and superior vena cava above the azygos vein. Occlusion was maintained for 10 minutes. After reperfusion, all physiological variables were continuously recorded for 3 hours. After 3 hours of reperfusion, animals were sacrificed. The regional cerebral cortex was removed, weighed and then dried (48 hours at 120° C.) to remove water content. The test drugs were given intravenously 5 minutes before ischemia.

In the group treated with the compound of Example 106, $\gamma$-CBF after reperfusion transiently increased, with reactive hyperemia to the same extent as that of the control group. Thereafter $\gamma$-CBF recovered to the pre-occlusion level 30 minutes after reperfusion, and then decreased gradually. However, the compound of Example 106 (1 mg/kg, i.v.) significantly inhibited a decrease in $\gamma$-CBF 3 hours after reperfusion (Decrease rate 3 hours after reperfusion : Compound of Example 106 18.0±3.1%, Control 44.3±1.4%). Wherereas the compound of Example 106 at 10 mg/kg (i.v.) almost completely inhibited the post-ischemia hypoperfusion in $\gamma$-CBF (Decrease rate 3 hours after reperfusion : compound of example 106 6.5±2.5%). The compound of Example 106 significantly inhibited the increase in water content in the cerebral cortex 3 hours after reperfusion.

| | | Water Content (%) |
|---|---|---|
| Control | | 79.81 ± 0.21 |
| Compound of Example 106 | 1 mg/kg. i.v. | 78.22 ± 0.08 (p 0.01) |
| Compound of Example 106 | 10 mg/kg. i.v. | 77.56 ± 0/36 (p 0.01) |

These results show that the compounds of the present invention offer potential protective effects in the case of complete cerebral ischemia-reperfusion.

This invention is illustrated in further detail in the Reference Examples and Examples, which are only examples, and do not limit this invention. Modification within the scope of this invention are permissible.

Elution in a column chromatography in the Reference Examples and Examples was conducted while monitoring with TLC (Thin Layer Chromatography). In the TLC monitoring, the TLC plate used was Kieselgel 60F$_{250}$ manufactured by Merck Co. (70-230 mesh), the developing solvent was the same as the one used for eluting in the column chromatography, and the detection was conducted with a UV detector. The silica gel for the column was Kieselgel 60 manufactured by Merck Co. (West Germany) (70-230 mesh). NMR spectra were indicated in $^1$H-NMR and measured using tetramethylsilane as an internal standard with a spectrometer Varian EM390 (90MHz) or a Gemini-200 (200 MHz) and all δ values are expressed in ppm. The symbols in Reference Examples and Examples have the following meaning.

s : singlet
br. : broad
d : doublet
t : triplet
q : quartet
m : multiplet
dd : doublet of doublets
J : coupling constant
Hz : Hertz
CDCl$_3$ : deutero-chloroform
D$_6$-DMSO: deutero-dimethylsulfoxide
% : percentage by weight
THF : tetrahydrofuran Further, room temperature means 15°-25° C., and all of melting points and temperature were shown on the centigrade.

REFERENCE EXAMPLE 1

3-(4-Chloro-cinnamoyl)amino-ε-caprolactam

N,N'-Carbonyldiimidazole (13.9 g) was added to a solution of p-cholorocinnamic acid (13.0 g) in THF (500 ml), and the whole was stirred for 20 mins. at room temperature, following by addition of 3-amino-δ-caprolactam (9.12 g). After stirring for 5 hrs., the resultant precipitate was collected by filtration, washed and dried under reduced pressure to give the title compound (Yield 11 g). This compound was used in the following reaction without purification. m.p. 256°-257°.

IR(KBr)cm$^{-1}$: 3198, 1686, 1644, 1614, 1563, 1348, 814.
NMR(CDCl$_3$)δ: 1.30-2.20(6H,m), 3.20-3.42(2H,m), 4.55-4.78(1H,m), 6.43(1H,d,J=16 Hz), 7.10(2H,m), 7.39(2H,m), 7.56(1H,d,J=16 Hz).

The following compounds were obtained in the method of the above Reference Example 1.

REFERENCE EXAMPLE 2

3-(4-Methoxycinnamoyl)amino-ε-caprolactam m.p. 238°-239°.
IR(KBr)cm$^{-1}$: 1672, 1650, 1604, 1532, 1511, 1275, 1172.
NMR(d$_6$-DMSO)δ: 1.18-1.85(6H,m), 3.07-3.25(2H,m), 3.76(3H,s), 4.52(1H,dd,J=7 Hz,10 Hz), 6.77(1H,d,J=16 Hz), 6.95(2H,d,J=8 Hz), 7.34(1H,d,J=16 Hz), 7.51(2H,d,J=8 Hz), 7.84(1H,t,J=5 Hz), 7.97(1H,d,J=7 Hz).

REFERENCE EXAMPLE 3

3-Cinnamoylamino-ε-caprolactam m.p. 194°-196°.
IR(KBr)cm$^{-1}$: 3294, 2924, 1656, 1619, 1536, 1480, 1433, 1226.
MNR(CDCl$_3$)δ: 1.28-2.23(6H,m), 3.09-3.40(2H,m), 4.56-4.79(1H,m), 6.49(1H,d,J=15 Hz), 6.90-7.60(5H,m), 7.61(1H,d,J=15 Hz).

REFERENCE EXAMPLE 4

3-(2-Phenylbutyryl)amino-ε-caprolactam m.p. 152°-153°.
IR(KBr)cm$^{-1}$: 3280, 2934, 1641, 1531, 1479, 1436.
NMR(CDCl$_3$)δ: 0.88(3H,t,J=7 Hz), 1.33-2.32(8H,m), 3.13-3.37(2H,m), 4.00(1H,t,J=7 Hz), 4.36-4.61(1H,m), 7.30(5H,s).

REFERENCE EXAMPLE 5

3-(4-Methoxybenzoyl)amino-δ-caprolactam m.p. 214°-215°.
IR(KBr)cm$^{-1}$: 2926, 1641, 1548, 1505, 1246, 1187.
NMR(d$_6$—DMSO)δ: 1.17-2.02(6H,m), 3.11-3.30(2H,m), 3.82(3H,s), 4.56-4.64(1H,m), 7.00 (2H,d,J=9 Hz), 7.83(2H,d,J=9 Hz), 8.09 (1H,d,J=6 Hz).

REFERENCE EXAMPLE 6

3-(4-Methylcinnamoyl)amino-ε-caprolactam m.p. 229°-230°.
IR(KBr)cm$^{-1}$: 3196, 2932, 1685, 1610, 1347, 807.
NMR(CDCl$_3$)δ: 1.22-2.28(6H,m), 2.37(3H,s), 3.23-3.50(2H,m), 4.59-4.81(1H,m), 6.46(1H,d,J=16 Hz), 7.20(2H,d,J=9 Hz), 7.43(2H,d,J=9 Hz), 7.63(1H,d,J=16 Hz).

REFERENCE EXAMPLE 7

3-(4-Ethoxycinnamoyl)amino-ε-caprolactam m.p. 236°-237°.
IR(KBr)cm$^{-1}$: 1686, 1644, 1605, 1562, 1513, 1304, 1233, 1173.
NMR(d$_6$-DMSO)δ: 1.32(3H,t,J=7 Hz), 1.20-2.00(6H,m), 3.09-3.33(2H,m), 4.06(2H,q,J=7 Hz), 4.44-4.63(1H,m), 6.72(1H,d,J=16 Hz), 6.93(2H,d,J=9 Hz), 7.32(1H,d,J=16 Hz), 7.50(2H,d,J=9 Hz).

REFERENCE EXAMPLE 8

3-(4-Isopropylcinnamoyl)amino-ε-caprolactam m.p. 199°-200°.
IR(KBr)cm$^{-1}$: 3320, 1670, 1651, 1615, 1528, 1430.
NMR(d$_6$-DMSO)δ: 1.18(6H,d,J=6 Hz), 1.33-2.00(6H,m), 2.81-2.98(1H,m), 3.04-3.25(2H,m), 4.43-4.63(1H,m), 6.83(1H,d,J=16 Hz), 7.24(2H,d,J=7 Hz), 7.38(1H,d,J=16 Hz), 7.50(2H,d,J=7 Hz).

REFERENCE EXAMPLE 9

3-[5-(4-Methoxyphenyl)pentadienoyl]amino-ε-caprolactam m.p. 204°-206°.
IR(KBr)cm$^{-1}$: 1645, 1598, 1510, 1480, 1435, 1255, 1176, 1029.
NMR(d$_6$-DMSO)δ: 1.15-1.93(6H,m), 3.00-3.20(2H,m), 3.77(3H,s), 4.38-4.61(1H,m), 6.26 (1H,d,J=14 Hz), 6.83-7.05(3H,m), 6.91(2H,d,J=8 Hz), 7.50(2H,d,J=8 Hz).

REFERENCE EXAMPLE 10

3-(4-Isopropoxycinnamoyl)amino-ε-caprolactam m.p. 225°–226°.

IR(KBr)cm$^{-1}$: 1671, 1651, 1606, 1535, 1510, 1254.

NMR(CDCl$_3$)δ: 1.16–2.30(6H,m), 1.32(6H,d,J=6 Hz), 3.12–3.40(2H,m), 4.42–4.78(2H,m), 6.33(1H,d,J=16 Hz), 6.83(2H,d,J=9 Hz), 7.41(2H,d,J=9 Hz), 7.55(1H,d,J=16 Hz).

REFERENCE EXAMPLE 11

3-(3,5-Di-tert-butyl-4-hyroxycinnamoyl)amino-ε-caprolactam m.p. 112°–113°.

IR(KBr)cm$^{-1}$: 2956, 1657, 1615, 1479, 1435, 1208.

NMR(d$_6$-DMSO)δ: 1.10–2.00(6H,m), 1.39(18H,s), 3.04–3.32(2H,m), 4.43–4.65(1H,m), 6.76(1H,d,J=16 Hz), 7.29(1H,d,J=16 Hz), 7.31(2H,s).

REFERENCE EXAMPLE 12

3-(2-Methoxycinnamoyl)amino-ε-caprolactam m.p. 213°–214°.

IR(KBr)cm$^{-1}$: 3216, 1685, 1643, 1613, 1557, 1448, 1245.

NMR(d$_6$-DMSO)δ: 1.18–1.96(6H,m), 3.03–3.27(2H,m), 3.83(3H,s), 4.43–4.65(1H,m), 6.76–7.56(6H,m).

REFERENCE EXAMPLE 13

3-(3,4-Methylenedioxycinnamoyl)amino-ε-caprolatam m.p. 275°–276°.

IR(KBr)cm$^{-1}$: 1669, 1652, 1616, 1532, 1500, 1488, 1250.

NMR(d$_6$-DMSO)δ: 1.17–1.95(6H,m), 3.05–3.32(2H,m), 4.40–4.60(1H,m), 6.03(2H,s), 6.73(1H,d,J=16 Hz), 6.80–7.17(3H,m), 7.30(1H,d,J=16 Hz).

REFERENCE EXAMPLE 14

3-Phenylcinnamoyl)amino-ε-caprolactam m.p. 159°–160°.

IR(KBr)cm$^{-1}$: 3354, 3254, 1656, 1617, 1501, 1445, 709.

NMR(d$_6$-DMSO)δ: 1.22–1.98(6H,m), 3.00–3.19(2H,m), 4.40(1H,dd,J=4 Hz,7 Hz), 6.95–7.56 (11H,m).

REFERENCE EXAMPLE 15

3-(2,3,4-Trimethoxycinnamoyl)amino-ε-caprolactam m.p. 208°–209°.

IR(KBr)cm$^{-1}$: 1673, 1646, 1614, 1495, 1464, 1297, 1097.

NMR(d$_6$-DMSO)δ: 1.18–1.97(6H,m), 3.08–3.22(2H,m), 3.75(3H,s), 3.80(3H,s), 3.82(3H,s), 4.43–4.63(1H,m), 6.79(1H,d,J=16 Hz), 6.89(1H,d,J=9 Hz), 7.32(1H,d,J=9 Hz), 7.53(1H,d,J=16 Hz).

REFERENCE EXAMPLE 16

3-(3,4-Dimethoxycinnamoyl)amino-ε-caprolactam m.p. 185°–186°.

IR(KBr)cm$^{-1}$: 3302, 1650, 1611, 1514, 1468, 1260, 1137.

NMR(d$_6$-DMSO)δ: 1.18–1.96(6H,m), 3.08–3.29(2H,m), 3.79(3H,s), 3.81(3H,s), 4.49–5.08 (1H,m), 6.86(1H,d,J=16 Hz), 6.98 (1H,d,J=8 Hz), 7.13(1H,dd,J=2 Hz,8 Hz), 7.23(1H,d,J=2 Hz), 7.34(1H,d,J=16 Hz).

REFERENCE EXAMPLE 17

3-(3,4-Dimethoxybenzoyl)amino-ε-caprolactam

N,N′-Carbonyldiimidazole (9.79 g) was added to a solution of 3,4-dimethoxybenzoic acid (10.0 g) in THF (300 ml) and the whole was stirred for 30 mins. at room temperature. Then, following by addition of 3-amino-ε-caprolactam (7.04 g), the mixture was stirred for 5 hrs. The resultant precipitate was collected by filtration, washed and dried under reduced pressure to give the title compound (8.5 g). This product was used in the following reaction without purification. m.p. 190°–191°.

IR(KBr)cm$^{-1}$: 1657, 1617, 1574, 1510, 1476, 1263.

NMR(d$_6$-DMSO)δ: 1.16–2.00(6H,m), 3.03–3.25(2H,m), 3.81(6H,s), 4.57–4.65(1H,m), 7.02 (1H,d,J=8 Hz), 7.43–7.50(2H,m), 7.83–7.89(1H,m), 8.15(1H,d,J=7 Hz).

The following compounds were obtained in the method of the above Reference Example 17.

REFERENCE EXAMPLE 18

3-(3-Methoxycinnamoyl)amino-ε-caprolactam m.p. 173°–174°.

IR(KBr)cm$^{-1}$: 3312, 1671, 1653, 1621, 1578, 1540, 1434, 1289.

NMR(d$_6$-DMSO)δ: 1.15–2.00(6H,m), 3.12–3.28(2H,m), 3.79(3H,s), 4.54(1H,dd,J=3 Hz,7 Hz), 6.92–7.41(6H,m), 7.88(1H,t,J=4 Hz), 8.05(1H,d,J=7 Hz).

REFERENCE EXAMPLE 19

3-(3,5-Dimethoxycinnamoyl)amino-ε-caprolactam m.p. 174°–175°.

IR(KBr)cm$^{-1}$: 1654, 1619, 1535, 1426, 1208, 1160.

NMR(d$_6$-DMSO)δ: 1.20–1.97(6H,m), 3.09–3.32(2H,m), 3.77(6H,s), 4.53(1H,dd,J=4 Hz,7 Hz), 6.50(1H,t,J=2 Hz), 6.77(2H,d,J=2 Hz), 6.98(1H,d,J=16 Hz), 7.32(1H,d,J=16 Hz), 7.88(1H,t,J=6 Hz),8.01(1H,d,J=7 Hz).

REFERENCE EXAMPLE 20

3-(2,3-Dimethoxycinnamoyl)amino-ε-caprolactam m.p. 187°–188°.

IR(KBr)cm$^{-1}$: 3208, 1686, 1613, 1577, 1480, 1270.

NMR(d$_6$-DMSO)δ: 1.18–1.89(6H,m), 3.09–3.28(2H,m), 3.75(3H,s), 3.82(3H,s), 4.54(1H,dd, J=3 Hz,7 Hz), 6.93(1H,d,J=16 Hz), 7.03–7.22(3H,m), 7.64(1H,d,J=16 Hz), 7.85 (1H,t,J=6 Hz), 8.13(1H,d,J=7 Hz).

REFERENCE EXAMPLE 21

3-(2,5-Dimethoxycinnamoyl)amino-ε-caprolactam m.p. 190°–191°.

IR(KBr)cm$^{-1}$: 1655, 1600, 1524, 1494, 1431, 1223.

NMR(d$_6$-DMSO)δ: 1.20–1.93(6H,m), 3.00–3.26(2H,m), 3.75(3H,s), 3.80(3H,s), 4.54(1H,dd, J=2 Hz,6 Hz), 6.92–7.01(3H,m), 7.14 (1H,d,J=3 Hz), 7.64(1H,d,J=16 Hz), 7.88(1H,t,J=7 Hz), 8.02(1H,d,J=6 Hz).

REFERENCE EXAMPLE 22

3-(4-Methoxy-3-methylcinnamoyl)amino-ε-caprolactam m.p. 218°–219°.

IR(KBR)cm$^{-1}$: 3280, 2920, 1660, 1640, 1600, 1500, 1248, 1122.

NMR(d$_6$-DMSO)δ: 1.20–1.92(6H,m), 2.16(3H,s), 3.06–3.25(2H,m), 3.82(3H,s), 4.48–4.57 (1H,m), 6.78(1H,d,J=16 Hz), 6.97(1H,d, J=9 Hz), 7.31(1H,d,J=16 Hz), 7.39–7.42 (2H,m), 7.86(1H,t,J=5 Hz), 7.95(1H,d,J=7 Hz).

REFERENCE EXAMPLE 23

3-[4-Methoxy-3-(2-methylthioethoxy)cinnamoyl]-amono-ε-caprolactam m.p. 192°–193°.

IR(KBr)cm$^{-1}$: 1673, 1650, 1610, 1511, 1428, 1262, 1143.

NMR(d$_6$-DMSO)δ: 1.19–1.97(6H,m), 2.18(3H,s), 2,87 (2H,t,J=7 Hz), 3.02–3.28(2H,m), 3.79(3H,s), 4.17(2H,t,J=7 Hz), 4.52 (1H,dd,J=3 Hz,5 Hz), 6.84(1H,d,J=16 Hz), 6.98(1H,d,J=8 Hz), 7.13(1H,dd,J=3 Hz,8 Hz), 7.24(1H,d,J=3 Hz), 7.32(1H,d,J=16 Hz), 7.85–7.91(2H,m).

REFERENCE EXAMPLE 24

3-(3,4,5-Trimethoxycinnamoyl)amino-ε-caprolactam m.p. 197°–198°.

IR(KBr)cm$^{-1}$: 1667, 1645, 1600, 1578, 1502, 1411, 1122.

NMR(d$_6$-DMSO)δ: 1.18–1.97(6H,m), 3.03–3.24(2H,m), 3.69(3H,s), 3.82(6H,s), 4.53(1H,dd, J=3 Hz,7 Hz), 6.95(2H,s), 6.96(1H,d,J =16 Hz), 7.34(1H,d,J=16 Hz), 7.89–7.93(2H,m).

REFERENCE EXAMPLE 25

3-(2,4-Dimethoxycinnamoyl)amino-ε-caprolactam m.p. 207°–208°.

IR(KBr)cm$^{-1}$: 3294, 1678, 1644, 1599, 1519, 1212, 1159.

NMR(d$_6$-DMSO)δ: 1.21–1.89(6H,m), 3.07–3.20(2H,m), 3.81(3H,s), 3.86(3H,s), 4.53(1H,dd, J=3 Hz, 7 Hz), 6.56–6.61(2H,m), 6.78 (1H,d,J=16 Hz), 7.49(1H,d,J=9 Hz), 7.58 (1H,d,J=16 Hz), 7.84(1H,t,J=6 Hz), 7.95 (1H,d,J=7 Hz).

REFERENCE EXAMPLE 26

3-(3-Bromo-4-methoxycinnamoyl)amino-ε-caprolactam m.p. 226°–227°.

IR(KBr)cm$^{-1}$: 1671, 1649, 1619, 1598, 1496, 1260.

NMR(d$_6$-DMSO)δ: 1.19–1.96(6H,m), 3.08–3.25(2H,m), 3.89(3H,s), 4.48–4.57(1H,m), 6.89(1H, d,J=16 Hz), 7.16(1H,d,J=9 Hz), 7.33(1H,d, J=16 Hz), 7.59(1H,dd,J=2 Hz,9 Hz), 7.85 (1H,d,J=2 Hz).

REFERENCE EXAMPLE 27

3-(3,5-Di-tert-butyl-4-hydroxybenzoyl)amino-ε-caprolactam m.p. 131°–132°.

IR(KBr)cm$^{-1}$: 2954, 1710, 1675, 1644, 1479, 1427, 1231.

NMR(d$_6$-DMSO)δ: 1.23–1.98(6H,m), 1.41(18H,s), 3.09–3.28(2H,m), 4.53–4.62(1H,m), 7.59(2H,s).

REFERENCE EXAMPLE 28

3-(2,4-Dimethoxybenzoyl)amino-ε-caprolactam m.p. 196°–197°.

IR(KBr)cm$^{-1}$: 3310, 1669, 1494, 1328, 1261, 1210, 1013.

NMR(d$_6$-DMSO)δ: 1.18–2.09(6H,m), 3.04–3.24(2H,m), 3.83(3H,s), 3.95(3H,s), 4.50–4.58 (1H,m), 6.63–6.68(2H,m), 7.93(1H,d, J=9 Hz).

REFERENCE EXAMPLE 29

3-(3,4-Dimethylcinnamoyl)amino-ε-caprolactam m.p. 226°–227°.

IR(KBr)cm$^{-1}$: 2934, 1685, 1643, 1613, 1562, 1479, 1242.

NMR(d$_6$—DMSO)δ: 1.16–1.98(6H,m), 2.24(6H,s), 3.03–3.21(2H,m), 4.49–4.58(1H,m), 6.88 (1H,d,J=16 Hz), 7.17(1H,d,J=8 Hz), 7.29–7.37(3H,m).

REFERENCE EXAMPLE 30

3-(2-Methoxy-3-methylcinnamoyl)amino-ε-caprolactam m.p. 186°–187°.

IR(KBr)cm$^{-1}$: 3270, 3222, 1684, 1638, 1621, 1569, 1467.

NMR(d$_6$-DMSO)δ: 1.19–1.98(6H,m), 2.26(3H,s), 3.06–3.24(2H,m), 3.68(3H,s), 4.51–4.60 (1H,m), 6.94(1H,d,J=16 Hz), 7.09(1H,t, J=6 Hz), 7.24(1H,d,J=6 Hz), 7.47(1H,d, J=6 Hz), 7.63(1H,d,J=16 Hz), 7.87(1H,t, J=5 Hz), 8.15(1H,d,J=7 Hz).

REFERENCE EXAMPLE 31

3-(3-Methoxybenzoyl)amino-ε-caprolactam m p. 148°–149°.

IR(KBr)cm$^{-1}$: 1680, 1648, 1587, 1542, 1487, 1300.

NMR(d$_6$-DMSO)δ: 1.19–2.00(6H,m), 3.03–3.27(2H,m), 3.81(3H,s), 4.57–4.68(1H,m), 7.07–7.14(1H,m), 7.35–7.42(3H,m).

REFERENCE EXAMPLE 32

3(α-Methylcinnamoyl)amino-ε-caprolactam m.p. 160°–161°.

IR(KBr)cm$^{-1}$: 3384, 1672, 1660, 1593, 1511, 1475.

NMR(d$_6$-DMSO)δ: 1.18–1.96(6H,m), 2.03(3H,s), 3.02–3.27(2H,m), 4.46–4.54(1H,m), 7.29–7.43(6H,m).

REFERENCE EXAMPLE 33

3-(4-Trifluoromethylbenzoyl)amino-ε-caprolactam.

m.p. 283°–284°.

IR(KBr)cm$^{-1}$: 1687, 1636, 1324, 1295, 1174, 1116.

NMR(d$_6$-DMSO)δ: 1.14–2.00(6H,m), 3.04–3.24(2H,m), 4.60–4.71(1H,m), 7.86(2H,d,J=8 Hz), 8.07(2H,d,J=8 Hz).

REFERENCE EXAMPLE 34

3-(3,4-Methylenedioxybenzoyl)amino-ε-caprolactam m.p. 196°–197°.

IR(KBr)cm$^{-1}$: 1660, 1635, 1602, 1475, 1253, 1033.

NMR(d$_6$—DMSO)δ: 1.12–1.99(6H,m), 3.08–3.27(2H,m), 4.55–4.62(1H,m), 6.11(2H,s), 6.99 (1H,d,J=8 Hz), 7.39(1H,d,J=2 Hz), 7.45 (1H,dd,J=2 Hz,8 Hz).

REFERENCE EXAMPLE 35

3-(p-Toluoyl)amino-ε-caprolactam m.p. 202°–203°.

IR(KBr)cm$^{-1}$: 3262, 3200, 1654, 1539, 1295, 1282.

NMR(d$_6$-DMSO)δ: 1.22–1.98(6H,m), 2.36(3H,s), 3.03–3.24(2H,m), 4.56–4.64(1H,m), 7.28(2H,d,J=8 Hz), 7.76(2H,d,J=8 Hz).

REFERENCE EXAMPLE 36

3-(2,3,4-Trimethoxybenzoyl)amino-ε-caprolactam m.p. 240°–241°.

IR(KBr)cm$^{-1}$: 3262, 1678, 1656, 1634, 1519, 1482, 1093.

NMR(d$_6$-DMSO)δ: 1.15–2.08(6H,m), 3.08–3.21(2H,m), 3.78(3H,s), 3.85(3H,s), 3.90(3H,s), 4.52–4.61(1H,s), 6.95(1H,d,J=9 Hz), 7.70(1H,d,J=9 Hz).

REFERENCE EXAMPLE 37

3-(3-Trifluoromethylcinnamoyl)amino-ε-caprolactam m.p. 203°–204°

IR(KBr)cm$^{-1}$: 1673, 1651, 1624, 1347, 1162, 1121.

NMR(d$_6$-DMSO)δ: 1.17–1.98(6H,m), 3.09–3.36(2H,m), 4.50–4.59(1H,m), 7.15(1H,d,J=16 Hz), 7.50(1H,d,J=16 Hz), 7.61–7.98(4H,m).

REFERENCE EXAMPLE 38

3-(N-tert-Butoxycarbonyl-β-alanyl)amino-ε-caprolactam m.p. 110°–111°.

IR(KBr)cm$^{-1}$: 3346, 1677, 1632, 1526, 1285, 1173.

NMR(d$_6$—DMSO)δ: 1.25–2.18(6H,m), 1.42(9H,s), 2.41(2H,t,J=6 Hz), 3.14–3.47(4H,m), 4.41–4.60(1H,m).

REFERENCE EXAMPLE 39

3-(4-Methoxycarbonylbenzoyl)amino-ε-caprolactam m.p. 226°–227°.

IR(KBr)cm$^{-1}$: 3306, 1714, 1672, 1632, 1428, 1284.

NMR(d$_6$-DMSO)δ: 1.20–2.02(6H,m), 3.10–3.22(2H,m), 3.89(3H,s), 4.60–4.68(1H,m), 7.98 (2H,d,J=9 Hz), 8.06(2H,d,J=9 Hz).

REFERENCE EXAMPLE 40

3-(4-Ethoxycarbonylstyryl)amino-ε-caprolactam m.p. 208°–209°.

IR(KBr)cm$^{-1}$: 1715, 1670, 1655, 1619, 1282, 1272.

NMR(d$_6$-DMSO)δ: 1.21–1.98(6H,m), 1.33(3H,t,J=7 Hz),
3.07–3.22(2H,m), 4.33(2H,q,J=7 Hz),
4.50–4.59(1H,m), 7.09(1H,d,J=16 Hz),
7.46(1H,d,J=16 Hz), 7.72(2H,d,J=8 Hz),
7.98(2H,d,J=8 Hz).

REFERENCE EXAMPLE 41

3-[(4-tert-Butoxycarbonylaminomethyl)benzoyl]amino-ε-caprolactam m.p. 174°–175°.

IR(KBr)cm$^{-1}$: 3364, 1683, 1637, 1527, 1288, 1170.

NMR(d$_6$-DMSO)δ: 1.21–2.00(6H,m), 1.40(9H,s), 3.02–3.28(2H,m), 4.17(2H,d,J=8 Hz), 4.56–4.65(1H,m), 7.32(2H,d,J=8 Hz), 7.80(2H,d,J=8 Hz).

REFERENCE EXAMPLE 42

3-(4-Ethoxycarbonyloxycinnamoyl)amino-ε-caprolactam

Ethyl chloroformate (22.2 ml) was added dropwise to a mixture of 3-hydroxy-4-methoxycinnamic acid (22.5 g), triethylamine (32.3 ml) and THF (400 ml) under ice-cooling and stirring, followed by stirring for 15 mins. Subsequently, to the mixture was added dropwise a solution of 3-amino-ε-caprolactam (14.9 g) in THF (200 ml), and then the whole was stirred for 1 hr. at room temperature. After completing the dropping, the reaction mixture was concentrated under reduced pressure, and the residue was dissolved in chloroform. This solution was washed with water, dried and distilled under reduced pressure to remove the solvent. The residue was washed with ethyl acetate, dried under reduced pressure to give the title compound (28 g). This compound was used in the following reaction without purification. m.p. 209°–210°.

IR(KBr)cm$^{-1}$: 1770, 1650, 1613, 1515, 1249, 1217.

NMR(CDCl$_3$)δ: 1.23–1.95(6H,m), 1.37(3H,t,J=7 Hz), 3.20–3.40(2H,m), 3.86(3H,s), 4.41 (2H,q,J=7 Hz), 4.55–4.78(1H,m), 6.35 (1H,d,J=16 Hz), 6.92(1H,d,J=9 Hz), 7.30–7.40(2H,m), 7.51(1H,d,J=16 Hz).

The following compound was obtained by the method of the above

REFERENCE EXAMPLE 42.

REFERENCE EXAMPLE 43

(4-Ethoxycarbonyloxybenzoyl)amino-ε-caprolactam m.p 195°–196°.

IR(KBr)cm$^{-1}$: 3312, 3266, 1766, 1683, 1634, 1290, 1252, 1212.

NMR(d$_6$-DMRO)δ: 1.40(3H,t,J=9 Hz), 1.53–2.36(6H,m), 3.20–3.41(2H,m), 4.31(2H,q,J=9 Hz), 4.58–4.80(1H,m), 7.26(2H,d,J=8 Hz), 7.90(2H,d,J=8 Hz).

REFERENCE EXAMPLE 44

3-(4-cyanobenzoyl)amino-ε-caprolactam

The title compound was obtained in the method of Reference Example 17.

m.p. 189°–190°.

IR(KBr)cm$^{-1}$: 2224, 1643, 1549, 1300, 937, 758.

NMR(d$_6$-DMSO)δ: 1.17–2.01(6H,m), 3.10–3.26(2H,m), 4.59–4.60(1H,m), 7.96(2H,d,J=8 Hz), 8.03(2H,d,J=8 Hz).

REFERENCE EXAMPLE 45

3-(3-Cyanobenzoyl)amino-ε-caprolactam

The title compound was obtained in the method of Reference Example 17.

m.p. 221°–222°.

IR(KBr)cm$^{-1}$: 2932, 1682, 1669, 1647, 1551, 1301.

NMR(d$_6$-DMSO)δ: 1.20–2.00(6H,m), 3.09–3.28(2H,m), 4.60–4.71(1H,m), 7.70(1H,t,J=8 Hz), 7.84(1H,t,J=6 Hz), 7.99–8.04(1H,m), 8.15–8.20(1H,m), 8.31–8.32(1H,m), 8.58(1H,d,J=7 Hz).

REFERENCE EXAMPLE 46

3-(5-Benzimidazolecarbonyl)amino-ε-caprolactam

The title compound was obtained in the method of Reference Example 17.

m.p. 297°–299°.

IR(KBr)cm$^{-1}$: 3258, 1672, 1623, 1540, 1305, 1289.
NMR(d$_6$-DMSO)δ: 1.15–2.02(6H,m), 3.09–3.26(2H,m), 4.64(1H,dd,J=7 Hz,10 Hz), 7.64–8.34 (6H,m).

REFERENCE EXAMPLE 47

3-Nicotinoylamino-ε-caprolactam

The title compound was obtained in the method of Reference Example 17.
m.p. 220°–221°.
IR(KBr)cm$^{-1}$: 3338, 1677, 1646, 1528, 1418, 1334.
NMR(d$_6$-DMSO)δ: 1.15–2.01(6H,m), 3.02–3.28(2H,m), 4.60–4.70(1H,m), 7.46–7.55(1H,m,J=1H, 5 Hz,8 Hz), 7.83(1H,t,J=7 Hz), 8.20(1H, dt,J=2 Hz,8 Hz), 8.54(1H,d,J=7 Hz), 8.70 (1H,dd,J=2 Hz,5 Hz), 9.02(1H,dd,J=1 Hz,2 Hz).

REFERENCE EXAMPLE 48

3-Picolinoylamino-ε-caprolactam

The title compound was obtained in the method of Reference Example 17.
m.p. 177°–178°.
IR(KBr)cm$^{-1}$: 1685, 1653, 1509, 1487, 1469, 1424.
NMR(d$_6$-DMSO)δ: 1.22–2.11(6H,m), 3.03–3.19(2H,m), 4.52–4.62(1H,m), 7.60–7.68(1H,m), 7.98–8.16(3H,m), 8.66–8.72(1H,m), 9.04(1H,d,J=6 Hz).

REFERENCE EXAMPLE 49

3-[4-(4-Methylpiperazinyl)benzoyl]amino-ε-caprolactam

The title compound was obtained in the method of Reference Example 17.
m.p. 232°–234°.
IR(KBr)cm$^{-1}$: 3282, 1679, 1544, 1513, 1451, 1293, 1244.
NMR(d$_6$-DMSO)δ: 1.16–1.98(6H,m), 2.22(3H,s), 2.44 (4H,t,J=5 Hz), 3.12–3.21(2H,m), 3.25(4H,t,J=5 Hz), 4.53–4.63(1H,m), 6.96(2H,d,J=9 Hz), 7.73(2H,d,J=9 Hz).

REFERENCE EXAMPLE 50

3-(1-Methyl-1H-1,2,3-triazole-4-carbonyl)amino-ε-caprolactam

The title compound was obtained in the method of Reference Example 17.
m.p. 259°–260°.
IR(KBr)cm$^{-1}$: 3388, 3108, 1677, 1640, 1571, 1502.
NMR(d$_6$-DMSO)δ: 1.13–2.07(6H,m), 3.03–3.28(2H,m), 4.09(3H,s), 4.55(1H,dd,J=6 Hz,10 Hz), 8.05(1H,t,J=6 Hz), 8.26(1H,d,J=6 Hz), 8.54(1H,s).

REFERENCE EXAMPLE 51

3-(Indole-3-carbonyl)amino-ε-caprolactam

The title compound was obtained in the method of Reference Example 17.
m.p. 243°–244°.
IR(KBr)cm$^{-1}$: 3272, 1675, 1620, 1548, 1439, 1310, 1209.
NMR(d$_6$—DMSO)δ: 1.17–2.01(6H,m), 3.05–3.26(2H,m), 4.66(1H,dd,J=7 Hz,10 Hz), 7.11–7.20 (2H,m), 7.42–7.47(1H,m), 7.71(1H, d,J=7 Hz), 7.88–7.93(1H,m), 8.04–8.09(2H,m), 11.63(1H,br.).

EXAMPLE 1

2-(4-Chlorostyryl)-5,6,7,8-tetrahydro-4H-thiazolo[5,4-b]azepine 3-(4-Chlorocinnamoyl)amino-ε-caprolactam (11.0 g) and phosphorus pentasulfide (8.37 g) were added to 500 ml of pyridine, and the whole was refluxed for 1.5 hrs. After cooling, the reaction mixture was added to a sodium hydrogen carbonate solution and extracted with chloroform. The extract was washed with water, dried and the solvent was distilled off under reduced pressure. The residue was purified by a column chromatography on silica gel, and recrystallized from cyclohexane to give the title compound as crystals, m.p. 188°–189° (yield 6.28 g, 57% of theory).
IR(KBr)cm$^{-1}$: 1 3274, 2926, 1543, 1432, 1355, 1090, 807.
NMR(CDCl$_3$)δ: 1.50–1.98(4H,m), 2.83–2.97(2H,m), 3.07–3.16(2H,m), 3.96(1H,br.s), 6.98(2H,d,J=1Hz), 7.32(4H,d,J=1Hz).
Elemental analysis for C$_{15}$H$_{15}$N$_2$SCl;
Calculated: C, 61.95; H, 5.20; N, 9.63.
Found : C, 62.08; H, 5.08; N, 9.90.

EXAMPLE 2

2-(4-Methoxystyryl)-5,6,7,8-tetrahydro-4H-thiazolo[5,4-b]azepine

The title compound was obtained by reacting 3-(4-methoxycinnamoyl)amino-ε-caprolactam and phosphorus pentasulfide in the method described in Example 1.
Yield 34.8%.
m.p. 130°–131° (recrystallized from cyclohexane).
IR(KBr)cm$^{-1}$: 2914, 1601, 1547, 1510, 1251, 1175, 949.
NMR(CDCl$_3$)δ: 1.67–1.84(4H,m), 2.89(2H,t,J=6 Hz), 3.11(2H,t,J=5 Hz), 3.82(3H,s), 6.88 (2H,d,J=9 Hz), 6.98(2H,s), 7.41(2H,d J=9 Hz).
Elemental analysis for C$_{16}$H$_{18}$N$_2$OS;
Calculated: C, 67.10; H, 6.33; N, 9.78.
Found : C, 67.29; H, 6.23; N, 9.70.

EXAMPLE 3

2-Styryl-5,6,7,8-tetrahydro-4H-thiazolo[5,4-b]azepine

The title compound was obtained by reacting 3-cinnamoylamino-ε-caprolactam and phosphorus pentasulfide in the method described in Example 1.
Yield 40.3%.
m.p. 169°–170° (recrystallized from cyclohexane).
IR(KBr)cm$^{-1}$: 3220, 2918, 1523, 1439, 1362, 1269, 938.
NMR(CDCl$_3$)δ: 1.50–1.93(4H,m), 2.80–2.92(2H,m), 3.01–3.12(2H,m), 7.05(2H,s), 7.23–7.59(5H,m).
Elemental analysis for C$_{15}$H$_{16}$N$_2$S;
Calculated: C, 70.27; H, 6.29; N, 10.93.
Found : C, 70.53; H, 6.30; N, 10.94.

EXAMPLE 4

2-(1-Phenylpropyl)-5,6,7,8-tetrahydro-4H-thiazolo[5,4-b]azepine

The title compound was obtained by reacting 3-(2-phenylbutyryl)amino-ε-caprolactam and phosphorus pentasulfide in a manner similar to that described in Example 1.
Yield 31.9%.
m.p. 106°–107° (recrystallized from hexane).
IR(KBr)cm$^-$: 3244, 2924, 1474, 1261, 701.

NMR(CDCl₃)δ: 0.89(3H,t,J=7 Hz),1.38-2.38(6H,m), 2.77-3.05(4H,m), 3.32(1H,br.s), 4.93(1H,t,J=8 Hz), 7.28(5H,s).

Elemental analysis for $C_{16}H_{20}N_2S$;
Calculated: C, 70.55; H, 7.40; N, 10.28.
Found : C, 70.45; H, 7.27; N, 10.15.

EXAMPLE 5

2-(4-Methoxyphenyl)-5,6,7,8-tetrahydro-4H-thiazolo[5,4-b]azepine hydrochloride

By using the method of Example 1, the title compound was obtained by reacting 3-(4-methoxybenzoyl)amino-ε-caprolactam and phosphorus pentasulfide, purifying and then making a salt from hydrochloric acid.

Yield 9.6%.

m.p. 177°-178° (recrystallized from a mixture of methanol and ethyl ether).

IR(KBr)cm⁻¹: 1605, 1533, 1292, 1281, 1263, 1190, 832.

NMR(CDCl₃)δ: 1.50-1.90(4H,m), 3.03-3.30(4H,m), 3.80(3H,s), 6.89(2H,d,J=9 Hz), 7.98 (2H,d,J=9 Hz).

Elemental analysis for $C_{14}H_{16}N_2S \cdot HCl$;
Calculated: C, 56.65; H, 5.77; N, 9.44; Cl, 11.94.
Found : C, 56.48; H, 5.87; N, 9.40; Cl, 12.17.

EXAMPLE 6

2-(4-Methylstyryl)-5,6,7,8-tetrahydro-4H-thiazolo[5,4-b]-azepine

The title compound was obtained by reacting 3-(4-methylcinnamoyl)amino-ε-caprolactam and phosphorus pentasulfide in the method described in Example 1.

Yield 49.5%.

m.p. 166°-167° (recrystallized from cyclohexane).

IR(KBr)cm⁻¹: 2920, 1546, 1438, 1355, 1270, 955, 802.

NMR(CDCl₃)δ: 1.5-1.95(4H,m), 2.35(3H,s), 2.80-2.93(2H,m), 3.01-3.15(2H,m), 7.05(2H,s), 7.15(2H,d,J=8 Hz), 7.38 (2H,d,J=8 Hz).

Elemental analysis for $C_{16}H_{18}N_2S$;
Calculated: C, 71.07; H, 6.71; N, 10.36.
Found : C, 71.02; H, 6.57; N, 10.23.

EXAMPLE 7

2-(4-Ethoxystyryl)-5,6,7,8-tetrahydro-4H-thiazolo[5,4-b]azepine

The title compound was obtained by reacting 3-(4-ethoxycinnamoyl)amino-ε-caprolactam and phosphorus pentasulfide the method described in Example 1.

Yield 42.6%.

m.p. 159°-160° (recrystallized from cyclohexane).

IR(KBr)cm⁻¹: 2924, 1601, 1550, 1510, 1268, 1244, 1176.

NMR(CDCl₃)δ: 1.40(3H,t,J=7 Hz), 1.60-1.93(4H,m), 2.89(2H,dd,J=4 Hz,6 Hz), 3.11(2H,t,J=5 Hz), 4.03(2H,q,J=7 Hz), 6.84(2H,d,J=9 Hz), 6.96(2H,s), 7.36(2H,d,J=9 Hz).

Elemental analysis for $C_{17}H_{20}N_2OS$;
Calculated: C, 67.97; H, 6.71; N, 9.32.
Found : C, 68.06; H, 6.63; N, 9.45.

EXAMPLE 8

2-(4-Isopropylstyryl)-5,6,7,8-tetrahydro-4H-thiazolo[5,4-b]azepine

The title compound was obtained by reacting 3-(4-isopropylcinnamoyl)amino-ε-caprolactam and phosphorus pentasulfide in the method described in Example 1.

Yield 47.8%.

m.p. 148°-149°.

IR(KBr)cm⁻¹: 3258, 2950, 2922, 1547, 1438, 1357, 1266.

NMR(CDCl₃)δ: 1.23(6H,d,J=7 Hz), 1.61-1.93(4H,m), 2.72-3.18(5H,m), 7.19(2H,d,J=9 Hz), 7.20(2H,s), 7.38(2H,d,J=9 Hz).

Elemental analysis for $C_{18}H_{22}N_2S$;
Calculated: C, 72.44; H, 7.43; N, 9.39.
Found : C, 72.11; H, 7.34; N, 9.35.

EXAMPLE 9

2-[4-(4-Methoxyphenyl)butadienyl]-5,6,7,8-tetrahydro-4H-thiazolo [5,4-b]azepine

The title compound was obtained by reacting 3-[5-(4-methoxyphenyl)pentadienoyl]amino-ε-caprolactam and phosphorus pentasulfide in the method described in Example 1.

Yield 19.4%.

m.p. 140°-142° (recrystallized from cyclohexane).

IR(KBr)cm⁻¹: 1542, 1509, 1441, 1368, 1251, 1172, 986.

NMR(CDCl₃)δ: 1.52-1.93(4H,m), 2.80-2.92(2H,m), 3.03-3.14(2H,m), 3.80(3H,s), 6.43-6.76(4H,m), 6.83(2H,d,J=9 Hz), 7.35 (2H,d,J=9 Hz).

Elemental analysis for $C_{18}H_{20}N_2OS$;
Calculated: C, 69.20; H, 6.45; N, 8.97.
Found : C, 68.90; H, 6.62; N, 8.80.

EXAMPLE 10

2-(4-Isopropoxystyryl)-5,6,7,8-tetrahydro-4H-thiazolo[5,4-b]azepine

The title compound was obtained by reacting 3-(4-isopropoxycinnamoyl)amino-ε-caprolactam and phosphorus pentasulfide in the method described in Example 1.

Yield 35.5%.

m.p. 161°-162° (recrystallized from cyclohexane).

IR(KBr)cm⁻¹: 3266, 1547, 1509, 1442, 1359, 1239, 943.

NMR(CDCl₃)δ: 1.30(6H,d,J=6 Hz), 1.58-1.92(4H,m), 2.80-2.95(2H,m), 3.03-3.13(2H,m), 4.53(1H,m), 6.82(2H,J=9 Hz), 6.92(2H,s), 7.34(2H,d,J=9 Hz).

Elemental analysis for $C_{18}H_{22}N_2OS$;
Calculated: C, 68.75; H, 7.05; N, 8.91.
Found : C, 69.10; H, 7.12; N, 9.01.

EXAMPLE 11

2-(3,5-Di-tert-butyl-4-hydroxystyryl)-5,6,7,8-tetrahydro-4H-thiazolo[5,4-b]azepine oxalate By using the method of Example 1, the title compound was obtained by reacting 3-(3,5-di-tert-butyl-4-hydroxycinnamoyl)amino-ε-caprolactam and phosphorus pentasulfide, purifying and then neutralizing with oxalic acid.

Yield 37.4%.

m.p. 205°-206°.

IR(KBr)cm⁻¹: 2958, 1729, 1592, 1437, 1374, 1237, 1208.

NMR(CDCl₃)δ: 1.40(18H,s), 1.53-1.83(4H,m), 2.60-2.76(2H,m), 2.86-3.03(2H,m), 6.94(2H,s), 7.28(2H,s).

Elemental analysis for $C_{23}H_{32}N_2OS \cdot C_2H_2O_4 \cdot H_2O$;

Calculated: C, 60.95; H, 7.37; N, 5.69.
Found : C, 60.97; H, 7.30; N, 5.72.

EXAMPLE 12

2-(2-Methoxystyryl)-5,6,7,8-tetrahydro-4H-thiazolo [5,4-b]azepine oxalate

By using the method of Example 1, the title compound was obtained by reacting 3-(2-methoxycinnamoyl)-amino-ε-caprolactam and phosphorus pentasulfide, purifying and then neutralizing with oxalic acid.
Yield 36.7%.
m.p. 171°-172°.
IR(KBr)cm$^{-1}$: 1592, 1519, 1378, 1352, 1253, 1207.
NMR(d$_6$-DMSO)δ: 1.33-1.82(4H,m), 2.68-2.80(2H,m), 2.90-3.02(2H,m), 3.84(3H,s), 6.83-7.63(4H,m), 7.15(2H,s).
Elemental analysis for $C_{16}H_{18}N_2OS \cdot C_2H_2O_4 \cdot 0.3H_2O$;
Calculated: C, 56.62; H, 5.44; N, 7.34.
Found : C, 56.67; H, 5.13; N, 7.14.

EXAMPLE 13

2-(3,4-Methylenedioxystyryl)-5,6,7,8-tetrahydro-4H-thiazolo[5,4-b]azepine hydrochloride By using the method of Example 1, the title compound was obtained by reacting 3-(3,4-methylenedioxycinnamoyl)amino-ε-caprolactam and phosphorus pentasulfide, purifying and then neutralizing with hydrochloric acid.
Yield 42.3%.
m.p. 196°-197° (recrystallized from a mixture of chloroform and ethyl ether).
IR(KBr)cm$^{-1}$: 1597, 1505, 1487, 1449, 1356, 1256.
NMR(d$_6$-DMSO)δ: 1.50-1.91(4H,m), 2.75-2.93(2H,m), 2.99-3.15(2H,m), 6.06(2H,s), 6.90-7.55(5H,m).
Elemental analysis for $C_{16}H_{16}N_2O_2S \cdot HCl \cdot 0.3H_2O$;
Calculated: C, 56.15; H, 5.18; N, 8.19.
Found : C, 56.38; H, 4.89; N, 8.22.

EXAMPLE 14

2-(α-Phenylstyryl)-5,6,7,8-tetrahydro-4H-thiazolo [5,4-b]azepine hydrochloride

By using the method of Example 1, the title compound was obtained by reacting 3-(α-phenylcinnamoyl)-amino-ε-caprolactam and phosphorus pentasulfide, purifying and then neutralizing with hydrochloric acid.
Yield 13.5%.
m.p. 188°-189°.
IR(KBr)cm$^{-1}$: 3180, 1595, 1506, 1490, 1352, 693.
NMR(d$_6$-DMSO)δ: 1.47-1.90(4H,m), 2.83-3.11(4H,m), 6.90-7.56(11H,m).
Elemental analysis for $C_{21}H_{20}N_2S \cdot HCl \cdot 0.2H_2O$;
Calculated: C, 67.71; H, 5.79; N, 7.52.
Found : C, 67.79; H, 5.68; N, 7.53.

EXAMPLE 15

2-(2,3,4-Trimethoxystyryl)-5,6,7,8-tetrahydro-4H-thiazolo[5,4-b]azepine oxalate

By using the method of Example 1, the title compound was obtained by reacting 3-(2,3,4-trimethoxycinnamoyl)amino-ε-caprolactam and phosphorus pentasulfide, purifying and then neutralizing with oxalic acid.
Yield 42.7%.
m.p. 145°-146° (recrystallized from ethyl acetate).
IR(KBr)cm$^{-1}$: 1742, 1588, 1495, 1283, 1203, 1108, 1098.
NMR(d$_6$-DMSO)δ: 1.56-1.69(4H,m), 2.73(2H,t,J=5 Hz), 2.94-2.99(2H,m), 3.76(3H,s), 3.80 (3H,S), 3.82(3H,s), 6.83(1H,d,J=9 Hz), 7.06(2H,s), 7.39(1H,d,J=9 Hz).
Elemental analysis for $C_{18}H_{22}N_2O_3S \cdot C_2H_2O_4 \cdot 0.5H_2O$;
Calculated: C, 53.92; H, 5.66; N, 6.29.
Found : C, 53.66; H, 5.41; N, 6.14.

EXAMPLE 16

2-(3,4-Dimethoxystyryl)-5,6,7,8-tetrahydro-4H-thiazolo[5,4-b]azepine hydrochloride By using the method of Example 1, the title compound was obtained by reacting 3-(3,4-dimethoxycinnamoyl)amino-ε-caprolactam and phosphorus pentasulfide, purifying and then neutralizing with hdyrochloric acid.
Yield 23.7%.
m.p. 159°-160° (recrystallized from a mixture of chloroform and ehtyl ether).
IR(KBr)cm$^{-1}$: 3438, 3220, 1609, 1593, 1516, 1268.
NMR(d$_6$-DMSO)δ: 1.62-1.73(4H,m), 2.80-2.85(2H,m), 3.04-3.09(2H,m), 3.80(3H,s), 3.82 (3H,s), 7.01(1H,d,J=8 Hz), 7.17(1H,dd, J=8 Hz,2 Hz), 7.26(1H,d,J=2 Hz), 7.24(1H,d, J=16 Hz), 7.43(1H,d,J=16 Hz).
Elemental analysis for $C_{17}H_{20}N_2O_2S \cdot HCl \cdot 1.3H_2O$;
Calculated: C, 54.26; H, 6.32; N, 7.44.
Found : C, 54.48; H, 6.31; N, 7.46.

EXAMPLE 17

2-(9-Decenyl)-5,6,7,8-tetrahydro-4H-thiazolo[5,4-b]azepine 1,1'-Carbonyldiimidazole (15.8 g) was added to a solution of undecylenic acid (15 g) in THF, and the whole was stirred for 15 mins. at room temperature. After addition of 3-amino-ε-caprolactam (10.4 g), the mixture was stirred for 5 hrs. at room temperature, and then distilled under reduced pressure to remove the solvent. The resultant crude 3-(10-undecenoyl)amino-ε-caprolactam and phosphorus pentasulfide (18.1 g), were added to 500 ml of pyridine, and the whole was refluxed under stirring for 1 hr. After cooling, the reaction mixture was added to a saturated sodium hydrogen carbonate solution and extracted with chloroform. The extract was washed with water, dried and distilled under reduced pressure to remove the solvent. The residue was purified by a column chromatography on silica gel and made a salt of oxalic acid. It was recrystallized from isopropyl ether to give the title compound (yield 7.7 g, 24.7%).
m.p. 94°-95°.
IR(KBr)cm$^{-1}$: 2928, 2854, 1607, 1528, 1404, 1279, 720.
NMR(CDCl$_3$)δ: 1.30(12H,br.s), 1.50-2.16(6H,m), 2.78-3.17(6H,m), 4.89-5.07(2H,m), 5.58-6.03(1H,m).
Elemental analysis for $C_{17}H_{28}N_2S \cdot C_2H_2O_4$;
Calculated: C, 59.66; H, 7.90; N, 7.32.
Found : C, 59.78; H, 8.13; N, 7.28.

EXAMPLE 18

2-(2,6-Difluorophenyl)-5,6,7,8-tetrahydro-4H-thiazolo[5,4-b]azepine 1,1'-Carbonyldiimidazole (14.8 g), was added to a solution of 2,6-difluorobenzoic acid (12 g) in THF (200 ml) and followed by stirring for 15 mins. at room temperature. Then to the mixture was added 9.73 g of 3-amino-ε-caprolactam, and the whole was stirred for 5 hrs. at room temperature and the solvent was distilled off under reduced pressure. The residue was washed with methylenechloride to give 3-(2,6-difluorobenzoyl)amino-ε-caprolactam (13.5 g) as crude crystals. The crude crystals and phosphorus pentasulfide (8.96 g) were added to 200 ml of pyridine, and the whole was refluxed under stirring for 24 hrs. After cooling, the mixture was distilled to remove the solvent. To the residue was added a saturated sodium hydrogen carbonate solution and extracted with chloroform. The extract was washed with water, dried and concentrated under reduced pressure. The residue was purified by a column chromatography on silica gel and then recrystallized from a mixture of methylenechloride and isopropyl ether to give the title compound (3.19 g, 23.8%).
m.p. 143°–144°.
IR(KBr)cm$^{-1}$: 3230, 2912, 1467, 1355, 1013, 990, 783.
NMR(CDCl$_3$)δ: 1.50-2.00(4H,m), 2.91-3.25(4H,m), 6.78-7.45(3H,m).
Elemental analysis for C$_{13}$H$_{12}$N$_2$SF$_2$;
Calculated: C, 58.63; H, 4.54; N, 10.52.
Found C, 58.72; H, 4.52; N, 10.32.

EXAMPLE 19

2-(2,4-Difluorophenyl)-5,6,7,8-tetrahydro-4H-thiazolo[5,4-b]azepine

The title compound was obtained by reacting 2,4-difluorobenzoic acid, 3-amino-ε-caprolactam and phosphorus pentasulfide in the method described in Example 18.
Yield 43.7%.
m.p. 105.5°–107.0° (recrystallized from cyclohexane).
IR(KBr)cm$^{-1}$: 1545, 1504, 1479, 1436, 1351, 1095.
NMR(CDCl$_3$)δ: 1.50-1.98(4H,m), 2.90-3.16(4H,m), 3.76(1H,br.s), 6.73-7.03(2H,m), 8.03-8.30(1H,m).
Elemental analysis for C$_{13}$H$_{12}$N$_2$SF$_2$;
Calculated: C, 58.63; H, 4.54; N, 10.52.
Found : C, 58.68; H, 4.47; N, 10.59.

EXAMPLE 20

2-(3,4-Dichlorostyryl)-5,6,7,8-tetrahydro-4H-thiazolo[5,4-b]azepine

The title compound was obtained by reacting 3,4-dichlorocinnamic acid, 3-amino-ε-caprolactam and phosphorus pentasulfide in the method described in Example 18.
m.p. 191°–192° (recrystallized from isopropanol).
IR(KBr)cm$^{-1}$: 3276, 2922, 1539, 1428, 1355, 940.
NMR(CDCl$_3$)δ: 1.65-1.72(2H,m), 1.80-1.88(2H,m), 2.92(2H,t,J=6 Hz), 3.13(2H,t,J=5 Hz), 6.93(1H,d,J=16 Hz), 7.10(1H,d,J=16 Hz), 7.28(1H,dd,J=8 Hz,2 Hz), 7.40(1H,d,J=8 Hz), 7.52(1H,d,J=2 Hz).
Elemental analysis for C$_{15}$H$_{14}$N$_2$SCl$_2$;
Calculated: C, 55.39; H, 4.34; N, 8.61.
Found : C, 55.22; H, 4.26; N, 8.91.

EXAMPLE 21

2-(4-Phenylbutadienyl)-5,6,7,8-tetrahydro-4H-thiazolo[5,4-b]azepine

The title compound was obtained by reacting 5-phenyl-2,4-pentadienic acid, 3-amino-ε-caprolactam and phosphorus pentasulfide in the method described in Example 18.
Yield 31.9%.
m.p. 156°–157° (recrystallized from cyclohexane).
IR(KBr)cm$^{-1}$: 3278, 2914, 1547, 1509, 1495, 1369 980.
NMR(CDCl$_3$)δ: 1.53-1.92(4H,m), 2.80-2.92(2H,m), 3.03-3.16(2H,m), 6.70-6.87(4H,m), 7.18-7.46(5H,m).
Elemental analysis for C$_{17}$H$_{18}$N$_2$S;
Calculated: C, 72.30; H, 6.42; N, 9.92.
Found : C, 72.12; H, 6.35; N, 9.66.

EXAMPLE 22

2-(4-Nitrostyryl)-5,6,7,8-tetrahydro-4H-thiazolo-[5,4-b]azepine

The title compound was obtained reacting 4-nitrocinnamic acid, 3-amino-ε-caprolactam and phosphorus pentasulfide in the method described in Example 18.
Yield 20.2%.
m.p. 219°–220° (recrystallized from isopropanol).
IR(KBr)cm$^{-1}$: 3278, 1595, 1531, 1514, 1435, 1356, 1338, 1270, 936.
NMR(d$_6$-DMSO)δ: 1.65 (4H,br.s), 2.70-2.83(2H,m), 2.93-3.04(2H,m), 7.10(1H,d,J=16 Hz), 7.46(1H,d,J=16 Hz), 7.87(2H,d,J=9 Hz), 8.21(2H,d,J=9 Hz).
Elemental analysis for C$_{15}$H$_{15}$N$_3$O$_2$S;
Calculated: C, 59.78; H, 5.02; N, 13.94.
Found : C, 59.49; H, 4.88; N, 13.61.

EXAMPLE 23

2-(2-Fluorophenyl)-5,6,7,8-tetrahydro-4H-thiazolo[5,4-b]azepine

3-Amino-ε-caprolactam (11.0 g) and triethylamine (15.7 ml) were added to 200 ml of methylenechloride. Then a solution of 2-fluorobenzoyl chloride (15.0 g) in methylenechloride (30 ml) was added dropwise to the mixture under ice-cooling and stirring. Thereafter, the mixture was stirred for 1.5 hrs. at room temperature, and the resultant precipitate was collected by filtration to give 3-(2-fluorobenzoyl)amino-ε-caprolactam as crude crystals. This crystals and phosphorus pentasulfide (16.5 g) were added to 200 ml of pyridine, and the whole was refluxed for 12 hrs. After cooling, the pyridine was removed by distillation, and to the residue was added a saturated sodium hydrogen carbonate solution and extracted with chloroform. The extract was washed with water, dried, and the solvent was distilled off under reduced pressure. The residue was purified by a column chromatography on silica gel, and then recrystallized from ethyl ether to give the title compound (4.55 g, 24.7%).
m.p. 115°–116°.
IR(KBr)cm$^{-1}$: 3236, 2944, 2916, 1496, 1453, 1371, 1357, 1102, 757.
NMR(CDCl$_3$)δ: 1.36-2.03(4H,m), 2.92-3.20(4H,m), 3.66(1H,br.s), 6.93-7.32(3H,m), 8.08-8.27(1H,m).
Elemental analysis for C$_{13}$H$_{13}$N$_2$SF;
Calculated: C, 62.88; H, 5.28; N, 11.28.
Found : C, 62.87; H, 5.14; N, 11.36.

EXAMPLE 24

2-(4-Nitrophenyl)-5,6,7,8-tetrahydro-4H-thiazolo[5,4-b]azepine

The title compound was obtained by reacting 4-nitrobenzoylchloride, 3-amino-ε-caprolactam and phosphorus pentasulfide in the method described in Example 23.

Yield 44.8%.

m.p. 159°–160° (recrystallized from cyclohexane).

IR(KBr)cm$^{-1}$: 2920, 1592, 1534, 1510, 1490, 1430, 1355, 1303, 1103.

NMR(CDCl$_3$)δ: 1.49–1.96(4H,m), 2.90–3.00(2H,m), 3.10–3.20(2H,m), 4.14(1H,br.s), 7.86(2H,d,J=9 Hz), 8.21(2H,d,J=9 Hz).

Elemental analysis for C$_{13}$H$_{13}$N$_3$O$_2$S;
Calculated: C, 56.71; H, 4.76; N, 15.26.
Found : C, 56.90; H, 4.69; N, 15.39.

EXAMPLE 25

2-(3-Nitrophenyl)-5,6,7,8-tetrahydro-4H-thiazolo[5,4-b]azepine

The title compound was obtained by reacting 3-nitrobenzoylchloride, 3-amino-ε-caprolactam and phosphorus pentasulfide in the method described in Example 23.

Yield 45.7%.

m.p. 168°–169° (recrystallized from a mixture of chloroform and isopropyl ether).

IR(KBr)cm$^{-1}$: 2920, 1520, 1450, 1370, 1345, 1300, 1270, 735.

NMR(CDCl$_3$)δ: 1.49–1.99(4H,m), 2.93(2H,dd,J=4 Hz, 6 Hz), 3.06–3.16(2H,m), 3.83–4.19(1H,br.s), 7.50(1H,t,J=8 Hz), 8.00–8.16(2H,m), 8.57(1H,t,J=2 Hz).

Elemental analysis for C$_{13}$H$_{13}$N$_3$O$_2$S;
Calculated: C, 56.71; H, 4.76; N, 15.26.
Found : C, 56.66; H, 4.71; N, 15.10.

EXAMPLE 26

2-Phenyl-5,6,7,8-tetrahydro-4H-thiazolo[5,4-b]azepine

The title compound was obtained by reacting benzoyl chloride, 3-amino-ε-caprolactam and phosphrus pentasulfide in the method described in Example 23.

Yield 44.5%.

m.p. 122.0°–123.5° (recrystallized from a mixture of ethanol and water).

IR(KBr)cm$^{-1}$: 3228, 3004, 2926, 1564, 1524, 1502, 1462, 1370, 1270, 757.

NMR(CDCl$_3$)δ: 1.50–1.96(4H,m), 2.89–3.15(4H,m), 3.56(1H,br.s), 7.26–7.48(3H,m), 7.69–7.80(2H,m).

Elemental analysis for C$_{13}$H$_{14}$N$_2$S;
Calculated: C, 67.79; H, 6.13; N, 12.16.
Found : C, 67.55; H, 6.04; N, 12.17.

EXAMPLE 27

2-Ethyl-5,6,7,8-tetrahydro-4H-thiazolo[5,4-b]azepine oxalate

The title compound was obtained by reacting propionyl bromide, 3-amino-ε-caprolactam and phosphorus pentasulfide, purifying and then neutralizing with oxalic acid in the the method described in Example 23.

Yield 34.0%.

m.p. 145°–146° (recrystallized from isopropanol).

IR(KBr)cm$^{-1}$: 2930, 1720, 1600, 1520, 1370, 1275, 1200, 720.

NMR(d$_6$-DMSO)δ: 1.16(3H,t,J=7 Hz), 1.32–1.81(4H,m), 2.46–2.73(4H,m), 2.81–2.92(2H,m).

Elemental analysis for C$_9$H$_{14}$N$_2$S·C$_2$H$_2$O$_4$;
Calculated: C, 48.52; H, 5.92; N, 10.29.
Found : C, 48.52; H, 5.98; N, 10.18.

EXAMPLE 28

2-Styryl-5,6,7,8-tetrahydro-4H-thiazolo[5,4-b]azepine oxalate

The title compound was obtained by reacting cinnamoyl chloride, 3-amino-ε-caprolactam and phosphorus pentasulfide, purifying and then neutralizing with oxalic acid in the method described in Example 23.

Yield 53%.

m.p. 188°–189° (recrystallized from ethyl ether).

IR(KBr)cm$^{-1}$: 3280, 2920, 1610, 1590, 1520, 1380, 1350, 1190. NMR(CDCl$_3$)δ: 1.46–1.96(4H,m), 2.77–3.17(4H,m), 6.93(1H,d,J=16 Hz), 7.15(1H,d,J=16 Hz), 7.19–7.60(5H,m).

Elemental analysis for C$_{15}$H$_{16}$N$_2$S C$_2$H$_2$O$_4$ 0.5H$_2$O;
Calculated: C, 57.45; H, 5.39; N, 7.88.
Found : C, 57.46; H, 5.13; N, 7.91.

EXAMPLE 29

2-Heptadecyl-5,6,7,8-tetrahydro-4H-thiazolo[5,4-b]azepine

The title compound was obtained by reacting stearoyl chloride, 3-amino-ε-caprolactam and phosphorus pentasulfide in the method described in Example 23.

Yield 26.1%.

m.p. 75–76° (recrystallized from methanol).

IR(KBr)cm$^{-1}$: 3230, 2930, 2850, 1465, 1265.

NMR(CDCl$_3$)δ: 0.88(3H,t,J=5 Hz), 1.26(30H,br.s), 1.47–1.90(4H,m), 2.67–2.90(4H,m), 2.98–3.10(2H,m).

Elemental analysis for C$_{24}$H$_{44}$N$_2$S;
Calculated: C, 73.41; H, 11.29; N, 7.13.
Found : C, 73.46; H, 11.00; N, 7.31.

EXAMPLE 30

2-(2-Naphthyl)-5,6,7,8-tetrahydro-4H-thiazolo[5,4-b]azepine

The title compound was obtained by reacting naphthoyl chloride, 3-amino-ε-caprolactam and phosphorus pentasulfide in the method described in Example 23.

Yield 42.9%.

m.p. 171°–172°.

IR(KBr)cm$^{-1}$: 3442, 3240, 2920, 1529, 1508, 1371.

NMR(CDCl$_3$)δ: 1.56–2.00(4H,m), 2.92–3.18(4H,m), 7.35–8.18(7H,m).

Elemental analysis for C$_{17}$H$_{16}$N$_2$S;
Calculated: C, 72.82; H, 5.75; N, 9.99.
Found : C, 72.78; H, 5.87; N, 9.79.

EXAMPLE 31

2-(2-Thienyl)-5,6,7,8-tetrahydro-4H-thiazolo[5,4-b]azepine

The title compound was obtained by reacting 2-thenoyl chloride, 3-amino-ε-caprolactam and phosphorus pentasulfide in the method described in Example 23.

Yield 59%.

m.p. 123°–124°.

IR(KBr)cm$^{-1}$: 3240, 2916, 1554, 1519, 1415, 1370.

NMR(CDCl$_3$)δ: 1.47–1.95(4H,m), 2.83–2.95(2H,m), 3.00–3.11(2H,m), 3.65(1H,br.s), 6.90–7.00(1H,m), 7.19–7.23(2H,m).

Elemental analysis for C$_{11}$H$_{12}$N$_2$S$_2$;

Calculated: C, 55.90; H, 5.12; N, 11.85.
Found : C, 55.80; H, 5.13; N, 11.83.

EXAMPLE 32

4(4-Methyl-1-piperadinyl)acetyl-2-phenyl-5,6,7,8-tetrahydro-4H-thiazolo[5,4-b]azepine Chloroacetyl chloride (2.2 g) was added dropwise to a mixture of 2-phenyl-5,6,7,8-tetrahydro-4H-thiazolo[5,4-b]-azepine (3.0 g), triethylamine (3.6 ml) and methylenechloride (100 ml) under ice-cooling and stirring. After stirring for 30 mins. at room temperature, the mixture was distilled under reduced pressure to remove the solvent, and the residue was extracted with chloroform. The extract was washed with a saturated sodium hydrogen carbonate solution, water, dried over anhydrous sodium sulfate and the solvent removed by distillation under reduced pressure to give a crude product (4.0 g). To a solution of the above product (1.9 g) and triethylamine (2.6 ml) in 20 ml of THF was added N-methylpiperazine (1.4 ml), and the whole was stirred for 5 hrs. at room temperature. The reaction mixture was concentrated and extracted with ethyl ether. The extract was washed with water, dried and concentrated under reduced pressure. The residue was purified by a column chromatography on silica gel, converted into a salt of hydrochloric acid and then recrystallized from a mixture of isopropanol and ethyl ether to give the title compound (1.66 g, 56%).

m.p. 195°–197°.

IR(KBr)cm$^{-1}$: 3340, 2560, 1660, 1460, 1370.

NMR(CDCl$_3$)δ: 1.50–2.15(4H,m), 2.26(3H,s), 2.33–2.76(8H,m), 2.83–3.12(2H,m), 3.21 (2H,s), 3.62–3.86(2H,m), 7.30–7.54 (3H,m), 7.80–8.00(2H,m).

Elemental analysis for $C_{20}H_{26}N_4OS \cdot 2HCl \cdot 2H_2O$;
Calculated: C, 50.10; H, 6.73; N, 11.69.
Found : C, 49.83; H, 6.71; N, 11.67.

EXAMPLE 33

4-Morpholinoacetyl-2-phenyl-5,6,7,8-tetrahydro-4H-thiazolo[5,4-b]azepine hydrochloride The title compound was obtained by reacting 2-phenyl-5,6,7,8-tetrahydro-4H-thiazolo[5,4-b]azepine, chloroacetyl chloride and morpholine in the method described in Example 32.

Yield 34.4%.

m.p. 208°–211° (recrystallized from a mixture of isopropanol and ethyl ether).

IR(KBr)cm$^{-1}$: 2490, 1680, 1460, 1450, 1365, 1120.

NMR(CDCl$_3$)δ: 1.53–2.20(4H,m), 2.40–2.70(4H,m), 2.83–3.12(2H,m), 3.20(2H,s), 3.53–3.94(6H,m), 7.30–7.53(3H,m, 7.80–7.98(2H,m).

Elemental analysis for $C_{19}H_{23}N_3O_2S \cdot HCl \cdot 0.5H_2O$;
Calculated: C, 56.64; H, 6.25; N, 10.43.
Found : C, 56.40; H, 6.32; N, 10.49.

EXAMPLE 34

4-[3-(4-Methyl-1-piperazinyl)propionyl]-2-phenyl-5,6,7,8-tetrahydro-4H-thiazolo[5,4-b]azepine fumarate The title compound was obtained by reacting 2-phenyl-5,6,7,8-tetrahydro-4H-thiazolo[5,4-b]azepine, 3-chloropropionyl chloride, N-methylpiperazine and fumaric acid in the method described in Example 32.

Yield 35%.

m.p. 201°–202° (recrystallized from isopropanol).

IR(KBr)cm$^{-1}$: 2930, 1660, 1540, 1450, 1380, 1170.

NMR(CDCl$_3$)δ: 1.54–2.20(4H,m), 2.23(3H,s), 2.41 (8H,m), 2.59–2.76(4H,m), 2.88–3.13 (2H,m), 3.60–3.94(2H,m), 7.33–7.55 (3H,m), 7.80–7.96(2H,m).

Elemental analysis for $C_{21}H_{28}N_4OS \cdot C_4H_4O_4$;
Calculated: C, 59.98; H, 6.44; N, 11.19.
Found : C, 59.82; H, 6.58; N, 11.16.

EXAMPLE 35

4-(3-Morpholinopropionyl)-2-phenyl-5,6,7,8-tetrahydro-4H-thiazolo[5,4-b]azepine hydrochloride The title compound was obtained by reacting 2-phenyl-5,6,7,8-tetrahydro-4H-thiazolo[5,4-b]azepine, 3-chloropropionyl chloride, morpholine and hydrogen chloride in the method described in Example 32.

Yield 43%.

m.p. 184°–186° (recrystallized from isopropanol).

IR(KBr)cm$^{-1}$: 3450, 2920, 2370, 1640, 1455, 1430.

NMR(CDCl$_3$)δ: 1.52–2.19(4H,m), 2.29–2.51(4H,m), 2.60–2.73(4H,m), 2.86–3.10(2H,m), 3.50–3.88(6H,m), 7.32–7.53(3H,m), 7.81–7.97(2H,m).

Elemental analysis for $C_{20}H_{25}N_3O_2S \cdot HCl \cdot 0.5H_2O$;
Calculated: C, 57.61; H, 6.53; N, 10.08.
Found : C, 57.77; H, 6.49; N, 9.98.

EXAMPLE 36

4-[3-(3,4-Dimethoxyphenethyl)aminopropionyl]-2-phenyl-5,6,7,8-tetrahydro-4H-thiazolo[5,4-b ]azepine fumarate The title compound was obtained by reacting 2-phenyl-5,6,7,8-tetrahydro-4H-thiazolo[5,4-b]azepine, chloropropionyl chloride, β-(3,4-dimethoxyphenyl)ethylamine and fumaric acid in the method described in Example 32.

Yield 42%.

m.p. 143°–144° C. (recrystallized from ethyl ether).

IR(KBr)cm$^{-1}$: 1710, 1660, 1342, 1320, 1405, 1255.

NMR(CDCl$_3$)δ: 1.50–2.13(5H,m), 2.46–3.20(10H,m), 3.55–4.00(2H,m), 4.81(3H,s), 4.83 (3H,s), 6.75(3H,br.s), 7.33–7.98 (3H,m), 7.80–7.98(2H,m).

Elemental analysis for $C_{26}H_{31}N_3O_3S \cdot C_4H_4O_4 \cdot 0.5H_2O$;
Calculated: C, 61.00; H, 6.14; N, 7.11.
Found : C, 61.17; H, 5.94; N, 6.84.

EXAMPLE 37

4-(4-Methyl-1-piperazinyl)acetyl-2-styryl-5,6,7,8-tetrahydro-4H-thiazolo [5,4-b]azepine hydrochloride The title compound was obtained by reacting 2-styryl-5,6,7,8-tetrahydro-4H-thiazolo[5,4-b]azepine, chloroacetyl chloride, N-methylpiperazine and hydrogen chloride in the method described in Example 32.

Yield 23%.

m.p. 182°–184° (recrystallized from a mixture of methanol and ethyl ether).

IR(KBr)cm$^{-1}$: 3400, 1670, 1610, 1440, 1410.

NMR(d$_6$-DMSO)δ: 1.36–2.13(4H,m), 2.72–3.02 (5H,m), 3.27(2H,s), 3.36–4.00 (10H,m), 7.27–7.75(7H,m).

Elemental analysis for $C_{22}H_{28}N_4OS \cdot 3HCl \cdot 1.3H_2O$;
Calculated: C, 49.92; H, 6.40; N, 10.58.
Found : C, 49.97; H, 6.57; N, 10.59.

EXAMPLE 38

4-[(3,4-Dimethoxyphenethyl)aminoacetyl]-2-styryl-5,6,7,8-tetrahydro-4H-thiazolo [5,4-b]azepine hydrochloride The title compound was obtained by reacting 2-styryl-5,6,7,8-tetrahydro-4H-thiazolo5,4-b ]azepine, chloroacetyl chloride, 8-(3,4-dimethoxyphenyl)ethylamine and hydrogen chloride in the method described in Example 32.
Yield 29%.
m.p. 170°–172°.
IR(KBr)cm$^{-1}$: 1660, 1600, 1520, 1410, 1255, 1235.
NMR(CDCl$_3$)δ: 1.49–2.11(5H,m), 2.60–3.06(6H,m), 3.12(2H,s), 3.56–3.80(2H,m), 3.82 (3H,s), 3.84(3H,s), 6.74(3H,br.s), 7.26–7.41(7H,m).
Elemental analysis for C$_{27}$H$_{31}$N$_3$O$_3$S·3HCl·0.4H$_2$O;
Calculated: C, 58.14; H, 6.11; N, 7.53; S, 5.75.
Found : C, 58.23; H, 6.02; N, 7.47; S, 6.01.

EXAMPLE 39

2-(2-Fluorophenyl)-4-[3-(N-(4-fluorophenyl)-piperazino)propionyl]-5,6,7,8-tetrahydro-4H-thiazolo[5,4-b]azepine hydrochloride The title compound was obtained by reacting 2-(2-fluorophenyl)-5,6,7,8-tetrahydro-4H-thiazolo[5,4-b]azepine, 3-chloropropionyl chloride, N-(4-fluorophenyl)-piperazine and hydrogen chloride in the method described in Example 32.
Yield 51%.
m.p. 131°–132°.
IR(KBr)cm$^{-1}$: 3350, 1645, 1509, 1443, 1410, 1229.
NMR(d$_6$-DMSO)δ: 1.50–2.10(4H,m), 2.89–3.10(2H,m), 3.30–4.00(14H,m), 6.95–7.63(7H,m), 8.05–8.30(1H,m).
Elemental analysis for C$_{26}$H$_{28}$N$_4$OSF$_2$·3HCl·0.9H$_2$O;
Calculated: C, 51.35; H, 5.44; N, 9.21, S, 5.27; Cl, 17.49.
Found C, 51.39; H, 5.44; N, 9.16; S, 5.27; Cl, 17.14.

EXAMPLE 40

2-phenyl-4-stearoyl-5,6,7,8-tetrahydro-4H-thiazolo[5,4-b]azepine

Stearoyl chloride (4.65 ml) was added dropwise to a mixture of 2-phenyl-5,6,7,8-tetrahydro-4H-thiazolo[5,4-b]-azepine (2.65 g), triethylamine (2.26 ml) and THF (30 ml) under ice-cooling and stirring. After completing addtion dropwise, the mixture was stirred for 1.5 hrs. at room temperature and distilled under reduced pressure to remove the solvent. The residue was extracted with chloroform, and the extract was washed with water, dried and distilled to remove the solvent. The residue was purified by a column chromatography on silica gel to give the title compound (4.31 g, 76%).
m.p. 38°–40°.
IR(KBr)cm$^{-1}$: 2900, 2850, 1670, 1640, 1450, 1410.
NMR(CDCl$_3$)δ: 0.87(3H,t,J=6 Hz), 1.24(30H, br.s), 1.52–2.10(4H,s), 2.41(2H,t,J=5 Hz), 2.97(2H,t,J=5 Hz), 3.61–3.92(2H,m), 7.32–7.53(3H,m), 7.81–8.03(2H,m).
Elemental analysis for C$_{31}$H$_{48}$N$_2$OS;
Calculated: C, 74.95; H, 9.74; N, 5.64:
Found : C, 74.64; H, 9.67; N, 5.77.

EXAMPLE 41

4-Methanesulfonyl-2-(4-pyridyl)-5,6,7,8-tetrahydro-4H-thiazolo[5,4-b]azepine

Carbonyldiimidazole (15.8 g) was added gradually to a suspension of isonicotinic acid (10 g) in dimethylformamide (300 ml). The mixture was stirred for 30 mins. at room temperature, and then there was added 10.4 g of 3-amino-ε-caprolactam. The mixture was stirred for 3 hrs. at room temperature and the solvent was distilled off under reduced pressure. To the residue were added 200 ml of pyridine and 12.4 g of phosphorus pentasulfide, and the whole was refluxed for 1.5 hrs. After cooling, the mixture was distilled under reduced pressure to remove the solvent, and the residue was extracted with chloroform. The extract was washed with an aqueous sodium hydrogen carbonate and water, dried and the solvent removed by distillation under reduced pressure to give 14.3 g of a powder. To the powder (2.5 g) was added a solution (30 ml) of triethylamine (2.28 ml) in THF, and then added dropwise methanesulfonyl chloride (1.08 ml) under ice-cooling and stirring. The mixture was stirred for 1 hr. at room temperature, distilled to remove the solvent and extracted with chloroform. The extract was washed, dried and distilled under reduced pressure to remove the solvent. The residue was purified by a column chlomatography on silica gel and recrystallized from a mixture of methylenechloride and isopropyl ether to give the title compound (105 g, 24%).
m.p 193°–194°.
IR(KBr)cm$^{-1}$: 1595, 1530, 1430, 1370, 1340, 1150.
NMR(CDCl$_3$)δ: 1.56–2.16(4H,m), 3.00–3.20(2H,m), 3.04(3H,s), 3.79(2H,t,J=5 Hz), 7.66–7.80(2H,m), 8.61–8.78(2H,m).
Elemental analysis for C$_{13}$H$_{15}$N$_3$O$_2$S$_2$;
Calculated: C, 50.46; H, 4.89; N, 13.58.
Found : C, 50.33; H, 4.91; N, 13.61.

EXAMPLE 42

4-(5-Methyl-4-isooxazolyl)carbonyl-2-methyl-5,6,7,8-tetrahydro-4H-thiazolo[5,4-b]azepine A mixture of 3-acetylamino-ε-caprolactam (2.55 g), phosphorus pentasulfide (6.08 g) and pyridine (40 ml) was stirred for 20 hrs. at 80° C. on oil-bath. After cooling, to the reaction mixture was added chloroform, and the whole was washed with a sodium hydrogen carbonate solution and water, dried and removed the solvent by distillation under reduced pressure to give an oil (2.59 g). The oil was dissolved in 40 ml of pyridine, and to the whole was added dropwise (5-methyl-4-isooxazolyl)carbonyl chloride (4 g) under ice-cooling. After completing addition, the mixture was stirred at room temperature overnight, and distilled under reduced pressure to remove the solvent. The residue was purified by a column chromatography on silica gel, and then recrystallized from hexane to give the title compound (0.9 g, 19%).
m.p. 117.0°–118.5°.
IR(Nujol)cm$^{-1}$: 1650, 1605, 1560, 1450, 1400, 1240, 1180.
NMR(CDCl$_3$)δ: 1.5–2.2(4H,m), 2.9–3.2(2H,m), 3.7–4.0(2H,m), 2.60(6H,s), 7.60(1H,s).
Elemental analysis for C$_{13}$H$_{15}$N$_3$O$_2$S;
Calculated: C, 56.30; H, 5.45; N, 15.15.
Found C, 56.33; H, 5.33; N, 14.94.

EXAMPLE 43

4-(4-Fluorobenzoyl)-2-methyl-5,6,7,8-tetrahydro-4H-thiazolo[5,4-b]azepine

The title compound was obtained by reacting 3-acetylamino-ε-caprolactam, phosphorus pentasulfide and 4-chlorobenzoyl chloride in the method described in Example 42.

Yield 37%.

m.p. 93.5°–95.0° C. (recrystallized from hexane).

IR(Nujol)cm$^{-1}$: 1640, 1600, 1440, 1405, 1315, 1295, 1225, 1180, 845, 760.

NMR(CDCl$_3$)δ: 1.6–2.2(4H,m), 2.48(3H,s), 2.90–3.17(2H,m), 3.77–4.00(2H,m), 6.83–7.53(4H,m).

Elemental analysis for $C_{15}H_{15}N_2OSF$;
Calculated: C, 62.05; H, 5.21; N, 9.65.
Found : C, 62.24; H, 5.28; N, 9.60.

EXAMPLE 44

4-(α-Thenoyl)-2-methyl-5,6,7,8-tetrahydro-4H-thiazolo-[5,4-b]azepine

The title compound was obtained by reacting 2-acetylamino-ε-caprolactam, phosphorus pentasulfide and α-thenoyl chloride in the method described in Example 42.

Yield 45%.

m.p. 108.0°–110.0° (recrystallized from hexane).

IR(Nujol)cm$^{-1}$: 1630, 1440, 1420, 1302, 1290, 1180, 735.

NMR(CDCl$_3$)δ: 1.6–2.3(4H,m), 2.57(3H,s), 2.88–3.15(2H,m), 3.73–4.03(2H,m), 6.85–7.50(3H,m).

Elemental analysis for $C_{13}H_{14}N_2OS_2$;
Calculated: C, 56.09; H, 5.07; N, 10.06.
Found : C, 56.12; H, 5.04; N, 10.02.

EXAMPLE 45

4-Nicotinoyl-2-methyl-5,6,7,8-tetrahydro-4H-thiazolo-[5,4-b]azepine

The title compound was obtained by reacting 3-acetylamino-ε-caprolactam, phosphorus pentasulfide and nicotinoyl chloride in the method described in Example 42.

Yield 34%.

m.p. 107.0–109.0° C. (recrystallized from hexane).

IR(Nujol)cm$^{-1}$: 1650, 1585, 1550, 1465, 1420, 1310,

NMR(CDCl$_3$)δ: 1.8–2.3(4H,m), 2.45(3H,s), 2.92–3.20(2H,m), 3.77–4.03(2H,m), 7.13–8.6(4H,m).

Elemental analysis for $C_{14}H_{15}N_3OS$:
Calculated: C, 61.52; H, 5.53; N, 15.37.
Found: C, 61.84; H, 5.55; N, 15.20.

EXAMPLE 46

2-(3-Methoxystyryl)-5,6,7,8-tetrahydro-4H-thiazolo[5,4-b]azepine hydrochloride

By using the method of Example 1, the title compound was obtained by reacting 3-(3-methoxycinnamoyl)amino-ε-caprolactam and phosphorus pentasulfide, purifying and neutralizing with hydrogen chloride.

Yield 30.3%.

m.p. 177–178° (recrystallized from a mixture of chloroform and ethanol).

IR(KBr)cm$^{-1}$: 3366, 3216, 2930, 1604, 1525, 1489, 1269.

NMR(d$_6$—DMSO)δ: 1.63–1.74(4H,m), 2.80–2.86(2H,m), 3.01–3.07(2H,m), 3.80(3H,s), 6.94 (1H,dd,J=3Hz,7Hz), 7.18–7.20(2H,m), 7.32(1H,d,J=8Hz), 7.38(2H,s).

Elemental analysis for $C_{16}H_{19}N_2OSCl$:
Calculated: C, 59.52; H, 5.93; N, 8.68.
Found C, 59.19; H, 5.85; N, 8.69.

EXAMPLE 47

2-(3,5-Dimethoxystyryl)-5,6,7,8-tetrahydro-4H-thiazolo-[5,4-b]azepine

The title compound was obtained by reacting 3-(3,5-dimethoxycinnamoyl)amino-ε-caprolactam and phosphorus pentasulfide in the method described in Example 1.

Yield 21.4%.

m.p. 104°–105° C. (recrystallized from ethyl ether).

IR(KBr)cm$^{-1}$: 1594, 1546, 1431, 1419, 1355, 1207, 1156.

NMR(CDCl$_3$)δ: 1.62–1.90(4H,m), 2.90(2H,t,J=6Hz), 3.12(2H,t,J=5Hz), 3.81(6H,s), 3.93 (1H,br), 6.40(1H,t,J=2Hz), 6.62(2H, d,J=2Hz), 6.92(1H,d,J=16Hz), 7.10 (1H,d,J=16Hz).

Elemental analysis for $C_{17}H_{20}N_2O_2S$:
Calculated: C, 64.53; H, 6.37; N, 8.85.
Found C, 64.59; H, 6.52; N, 8.80.

EXAMPLE 48

2-(2,3-Dimethoxystyryl)-5,6,7,8-tetrahydro-4H-thiazolo-[5,4-b]azepine

The title compound was obtained by reacting 3-(2,3-dimethoxycinnamoyl)amino-ε-caprolactam and phosphorus pentasulfide in the method described in Example 1.

Yield 35%.

m.p. 125°–126° (recrystallized from cyclohexane).

IR(KBr)cm$^{-1}$: 3214, 1527, 1476, 1447, 1422, 1270, 1072.

NMR(CDCl$_3$)δ: 1.50–1.89(4H,m), 2.90(2H,t,J=6Hz), 3.12(2H,t,J=5Hz), 3.85(3H,s), 3.88 (3H,s), 6.84(2H,dd,J=2Hz,8Hz), 7.05 (1H,t,J=8Hz), 7.15(1H,d,J=16Hz), 7.16 (1H,dd,J=2Hz,8Hz), 7.31(1H,d,J=16Hz).

Elemental analysis for $C_{17}H_{20}N_2OS$:
Calculated: C, 64.53; H, 6.37; N, 8.85.
Found C, 64.44; H, 6.30; N, 8.91.

EXAMPLE 49

2-(2,5-Dimethoxystyryl)-5,6,7,8-tetrahydro-4H-thiazolo-[5,4-b]azepine

The title compound was obtained by reacting 3-(2,5-dimethoxycinnamoyl)amino-ε-caprolactam and phosphorus pentasulfide in the method described in Example 1.

Yield 32.3%.

m.p. 155–156° (recrystallized from cyclohexane).

IR(KBr)cm$^{-1}$: 1527, 1498, 1436, 1362, 1226, 1213.

NMR(CDCl$_3$)δ: 1.50–1.78(4H,m), 2.74(2H,t,J=6Hz), 2.92–3.02(2H,m), 3.75(3H,s), 3.80 (3H,s), 6.83(1H,dd,J=3Hz,9Hz), 6.96 (1H,d,J=9Hz), 7.18–7.21(3H,m).

Elemental analysis for $C_{17}H_{20}N_2O_2S$:
Calculated: C, 64.53; H, 85.
C, 64.39; H, 6.31; N, 8.71.

EXAMPLE 50

2-(3,4-Dimethoxyphenyl)-5,6,7,8-tetrahydro-4H-thiazolo-[5,4-b]azepine hydrochloride By using the method of Example 1, the title compound was obtained by reacting 3-( 3,4- dimethoxybenzoyl)amino-ε-caprolactam and phosphorus pentasulfide, purifying and then neutralizing with hydrogen chloride.

Yield 45.5%.

m.p. 186–187° (recrystallized from a mixture of methanol and ethyl ether).

IR(KBr)cm$^{-1}$: 1609, 1535, 1509, 1342, 1268, 1152.

NMR(d$_6$—DMSO)δ: 1.56–1.82(4H,m), 2.88–2.94(2H,m), 3.02–3.08(2H,m), 3.82(3H,s), 3.85 (3H,s), 7.05(1H,d,J=9Hz), 7.35(1H,dd, J=2Hz,9Hz), 7.58(1H,d,J=2Hz).

Elemental analysis for C$_{15}$H$_{19}$N$_2$O$_2$Cl·0.5H$_2$O:
Calculated: C, 53.64; H, 6.00; N, 8.34.
Found C, 53.39; H, 5.86; N, 8.05.

EXAMPLE 51

2-(4-Methoxy-3-methylstyryl)-5,6,7,8-tetrahydro-4H-thiazolo-[5,4-b]azepine

The title compound was obtained by reacting 3-(4-methoxy-3-methylcinnamoyl)amino-ε-caprolactam and phosphorus pentasulfide in the method described in Example 1.

Yield 33.6%.

m.p. 139–140° (recrystallized from cyclohexane).

IR(KBr)cm$^{-1}$: 2922, 1542, 1506, 1365, 1255, 1129.

NMR(CDCl$_3$)δ: 1.59–1.88(4H,m), 2.22(3H,s), 2.89 (2H,t,J=6Hz); 3.11(2H,t,J=5Hz), 3.84 (3H,s), 6.80(1H,d,J=9Hz), 6.96(2H,s), 7.26–7.30(2H,m).

Elemental analysis for C$_{17}$H$_{20}$N$_2$OS:
Calculated: C, 67.97; H, 6.71; N, 9.32.
Found C, 68.19; H, 6.80; N, 9.39.

EXAMPLE 52

2-[4-Methoxy-3-(2-methylthioethoxy)styryl]-5,6,7,8-tetrahydro-4H-thiazolo[5,4-b]azepine The title compound was obtained by reacting 3-4-methoxy-3-(2-methylthioethoxy)cinnamoyl]amino-ε-caprolactam and phosphorus pentasulfide in the method described in Example 1.

Yield 15.0%.

m.p. 117–118° (recrystallized from cyclohexane).

IR(KBr)cm$^{-1}$: 1553, 1514, 1442, 1358, 1263, 1141.

NMR(CDCl$_3$)δ: 1.97(4H,m), 2.20(3H,s), 2.81–2.95(2H,m), 2.90(2H,t,J=7Hz), 3.04–3.17(2H,m), 3.85(3H,s), 4.20(2H,t,J=7Hz), 6.81(1H,d,J=9Hz), 6.92(2H,s), 6.97–7.06(2H,m).

Elemental analysis for C$_{19}$H$_{24}$N$_2$O$_2$S$_2$:
Calculated: C, 60.61; H, 6.42; N, 7.44.
Found C, 60.62; H, 6.47; N, 7.40.

EXAMPLE 53

2-(3,4,5-Trimethoxystryl)-5,6,7,8-tetrahydro-4H-thiazolo-[5,4-b]azepine hydrochloride By using the method of Example 1, the title compound was obtained by reacting 3-(3,4,5-trimethoxycinnamoyl)amino-ε-caprolactam and phosphorus pentasulfide, purifying and then neutralizing with hydrogen chloride.

Yield 22.8%.

m.p. 204–205° (recrystallized from a mixture of methanol and ethyl ether).

IR(KBr)cm$^{-1}$: 2910, 1572, 1500, 1432, 1410, 1238, 1120.

NMR(d$_6$—DMSO)δ: 1.55–1.80(4H,m), 2.77–2.85(2H,m), 3.02–3.09(2H,m), 3.69(3H,s), 3.82 (6H,s), 6.95(2H,s), 7.28(2H,s).

Elemental analysis for C$_{18}$H$_{23}$N$_2$O$_3$SCl:
Calculated: C, 56.46; H, 6.05; N, 7.32.
Found C, 56.14; H, 6.01; N, 7.28.

EXAMPLE 54

2-(3-Ethoxycarbonyloxy-4-methoxystyryl)-5,6,7,8-tetrahydro-4H-thiazolo[5,4-b]azepine The title compound was obtained by reacting 3-(3-ethoxycarbonyloxy-4-methoxycinnamoyl)amino-ε-caprolactam and phosphorus pentasulfide in the method described in

EXAMPLE 1.

Yield 65.4%.

m.p. 132–133° (recrystallized from isopropyl ether).

IR(KBr)cm$^{-1}$: 1761, 1514, 1439, 1368, 1276, 1137, 1059.

NMR(CDCl$_3$)δ: 1.38(3H,t,J=7Hz), 1.50–1.95(4H,m), 2.80–2.92(2H,m), 3.02–3.13(2H,m), 3.86(3H,s), 4.30(2H,q,J=7Hz), 6.80–7.00(1H,m), 6.94 (2H,s), 7.25–7.37 (2H,m).

Elemental analysis for C$_{19}$H$_{22}$N$_2$O$_4$S:
Calculated: C, 60.94; H, 5.92; N, 7.48.
Found C, 60.86; H, 5.83; N, 7.52.

EXAMPLE 55

2-(2,4-Dimethoxystyryl)-5,6,7,8-tetrahydro-4H-thiazolo-[5,4-b]azepine hydrochloride By using the method of Example 1, the title compound was obtained by reacting 3-(2,4-dimethoxycinnamoyl)amino-ε-caprolactam and phosphorus pentasulfide, purifying and then neutralizing with hydrogen chloride.

Yield 8.5%.

m.p. 165–167° (recrystallized from a mixture of methanol and ethyl ether).

IR(KBr)cm$^{-1}$: 1603, 1542, 1505, 1433, 1289, 1265, 1209, 1158.

NMR(CDCl$_3$)δ: 1.58–1.89(4H,m), 2.86–2.91(2H,m), 3.08–3.13(2H,m), 3.83(3H,s), 3.86 (3H,s), 6.47(1H,dd,J=2Hz,8Hz), 6.52 (1H,d,J=2Hz), 7.09(1H,d,J=16Hz), 7.25 (1H,d,J=16Hz), 7.42(1H,d,J=8Hz).

Elemental analysis for C$_{17}$H$_{21}$N$_2$O$_2$SCl 1.5H$_2$O:
Calculated: C, 53.75; H, 6.37; N, 7.37.
Found C, 54.02; H, 6.10; N, 7.44.

EXAMPLE 56

2-(4-Ethoxycarbonyloxyphenyl)-5,6,7,8-tetrahydro-4H-thiazolo[5,4-b]azepine

The title compound was obtained by reacting 3-(4-ethoxycarbonyloxybenzoyl)amino-ε-caprolactam and phophorus pentasulfide in the method of Example 1.

Yield 21.3%.

m.p. 93–94° (recrystallized from a mixture of ethyl ether and hexane).

IR(KBr)cm$^{-1}$: 1753, 1508, 1370, 1302, 1258, 1207.

NMR(CDCl$_3$)δ: 1.36(3H,t,J=7Hz), 1.50–1.95(4H,m), 2.85–2.97(2H,m), 3.02–3.12(2H,m), 3.85(1H,br), 4.30(2H,q,J=7Hz), 7.16 (2H,d,J=9Hz), 7.75(2H,d,J=9Hz).

Elemental analysis for $C_{16}H_{18}N_2O_3S$:
Calculated: C, 60.36; H, 5.70; N, 8.80; S, 10.07.
Found C, 60.31; H, 5.60; N, 8.74; S, 10.12.

EXAMPLE 57

2-(3-Bromo-4-methoxystyryl)-5,6,7,8-tetrahydro-4H-thiazolo-[5,4-b]azepine

The title compound was obtained by reacting 3-(3-bromo-4-methoxycinnamoyl)amino-ε-caprolactam and phosphorus pentasulfide in the method of Example 1.
Yield 25.0%.
m.p. 158–159° (recrystallized from ethyl acetate).
IR(KBr)cm$^{-1}$: 1546, 1499, 1440, 1352, 1291, 1258.
NMR(CDCl$_3$)δ: 1.61–1.87(4H,m), 2.89(2H,t,J=6Hz), 3.09–3.14(2H,m), 3.91(3H,s), 6.88 (1H,d,J=9Hz), 6.93–6.94(2H,m), 7.37 (1H,dd,J=2Hz,9Hz), 7.66(1H,d,J=2Hz).

Elemental analysis for $C_{16}H_{17}N_2OSBr$:
Calculated: C, 52.61; H, 4.69; N, 7.67; S, 8.78.
Found C, 52.37; H, 4.64; N, 7.60; S, 8.92.

EXAMPLE 58

2-(3,5-Di-tert-butyl-4-hydroxyphenyl)-5,6,7,8-tetrahydro-4H-thiazolo[5,4-b]azepine hydrochloride By the method of Example 1, the title compound was obtained by reacting 3-(3,5-di-tert-butyl-4-hydroxybenzoyl)amino-ε-caprolactam and pentasulfide, purifying and then neutralizing with hydrogen chloride.
Yield 11.8%.
m.p. 194–196° (recrystallized from a mixture of ethanol and ethyl ether).
IR(KBr)cm$^{-1}$: 3486, 3220, 2924, 1608, 1394, 1307, 1226, 1119.
NMR(CDCl$_3$)δ: 1.49(18Hs), 1.61–1.87(4H,m), 3.11–3.16(2H,m), 3.24–3.30(2H,m), 5.82 (1H,s), 7.83(2H,s).

Elemental analysis for $C_{21}H_{31}N_2OSCl$:
Calculated: C, 63.85; H, 7.91; N, 7.09; S, 8.12; Cl, 8.98.
Found C, 64.03; H, 7.99; N, 6.90; S, 8.02; Cl, 8.86.

EXAMPLE 59

2-(2,4-Dimethoxyphenyl)-5,6,7,8-tetrahydro-4H-thiazolo-[5,4-b]azepine hydrochloride By the method of Example 1, the title compound was obtained by reacting 3-(2,4-dimethoxybenzoyl)amino-ε-caprolactam and phosphorus pentasulfide, purifying and then neutralizing with hydrogen chloride.
Yield 56.2%.
m.p. 214–215° (recrystallized from a mixture of ethanol and ethyl ether).
IR(KBr)cm$^{-1}$: 3198, 1610, 1572, 1527, 1321, 1300, 1212.
NMR(d$_6$—DMSO)δ: 1.55–1.81(4H,m), 2.90–2.97(2H,m), 3.02–3.10(2H,m), 3.86(3H,s), 3.99 (3H,s), 6.71–6.79(2H,m), 8.31(1H, d,J=9Hz).

Elemental analysis for $C_{15}H_{19}N_2O_2SCl$:
Calculated: C, 55.12; H, 5.86; N, 8.57; S, 9.81; Cl, 10.85.
Found C, 54.97; H, 5.84; N, 8.64; S, 9.79; Cl, 10.80.

EXAMPLE 60

2-(3,4-Dimethylstyryl)-5,6,7,8-tetrahydro-4H-thiazolo-[5,4-b]azepine

The title compound was obtained by reacting 3-(3,4-dimethylcinnamoyl)amino-ε-caprolactam and phosphorus pentasulfide in the method of Example 1.
Yield 50.4%.
m.p. 165°166° (recrystallized from ethyl acetate).
IR(KBr)cm$^{-1}$: 3258, 2944, 2920, 1544, 1431, 1355.
NMR(CDCl$_3$)δ: 1.52–1.96(4H,m), 2.26(6H,s), 2.80–2.92(2H,m), 3.03–3.14(2H,m), 3.86 (1H,br), 7.00(2H,s), 7.11–7.25(3H,m).

Elemental analysis for $C_{17}H_{20}N_2S$:
Calculated: C, 71.79; H, 7.09; N, 9.85; S, 11.27.
Found C, 71.92; H, 7.03; N, 9.83; S, 11.43.

EXAMPLE 61

2-(2-Methoxy-3-methylstyryl)-5,6,7,8-tetrahydro-4H-thiazolo[5,4-b]azepine

The title compound was obtained by reacting 3-(2-methoxy-3-methylcinnamoyl)amino-ε-caprolactam and phosphorus pentasulfide in the method of Example 1.
Yield 45.3%.
m.p. 114–115° (recrystallized from ethyl ether).
IR(KBr)cm$^{-1}$: 3216, 2920, 1528, 1436, 1368, 1353, 1005.
NMR(d$_6$—DMSO)δ: 1.62–1.89(4H,m), 2.31(3H,s), 2.90 (2H,t,J=6Hz), 3.12(2H,t,J=5Hz), 3.75 (3H,s), 7.02(1H,t,J=8Hz), 7.12(1H,dd, J=2Hz,8Hz), 7.14(1H,d,J=16Hz), 7.28 (1H,d,J=16Hz), 7.39(1H,dd,J=2Hz,8Hz).

Elemental analysis for $C_{17}H_{20}N_2OS$:
Calculated: C, 67.97; H, 6.71; N, 9.32; S, 10.67.
Found C, 67.91; H, 6.69; N, 9.34; S, 10.85.

EXAMPLE 62

2-(3-Methoxyphenyl)-5,6,7,8-tetrahydro-4H-thiazolo-[5,4-b]azepine

The title compound was obtained by reacting 3-(3-methoxybenzoyl)amino-ε-caprolactam and phosphorus pentasulfide in the method described in Example 1.
Yield 40.0%.
m.p. 82–83° (recrystallized from cyclohexane).
IR(KBr)cm$^{-1}$: 3206, 1597, 1495, 1370, 1272, 785.
NMR(CDCl$_3$)δ: 1.61–1.90(4H,m), 2.95(2H,t,J=6Hz), 3.12(2H,t,J=5Hz), 3.86(3H,s), 6.84–6.90(1H,m), 7.22–7.36(3H,m).

Elemental analysis for $C_{14}H_{16}N_2OS$:
Calculated: C, 64.59; H, 6.19; N, 10.76; S, 12.32.
Found C, 64.52; H, 6.03; N, 10.49; S, 12.44.

EXAMPLE 63

2-(α-Methylstyryl)-5,6,7,8-tetrahydro-4H-thiazolo[5,4-b]-azepine

The title compound was obtained by reacting 3-(α-methylcinnamoyl)amino-ε-caprolactam and phosphorus pentasulfide in the method of Example 1.
Yield 16.6%.
m.p. 122–123° (recrystallized from isopropyl ether).
IR(KBr)cm$^{-1}$: 3226, 2922, 1552, 1512, 1432, 1362, 1355, 696.
NMR(CDCl$_3$)δ: 1.61–1.89(4H,m), 2,32(3H,s), 2.92 (2H,t,J=6Hz), 3.11(2H,t,J=5Hz), 3.91 (1H,br.), 7.13–7.39(6H,m).

Elemental analysis for $C_{16}H_{18}N_2S$:

Calculated: C, 71.07; H, 6.71; N, 10.36; S, 11.86.
Found C, 71.0I; H, 6.55; N, 10.28; S, 11.63.

EXAMPLE 64

2-(4-Trifluoromethylphenyl)-5,6,7,8-tetrahydro-4H-thiazolo[5,4-b]azepine

The title compound was obtained by reacting 3-(4-trifluoromethylbenzoyl)amino-ε-caprolactam and phosphorus pentasulfide in the method of Example 1.
Yield 50.4%.
m.p. 158–159° (recrystallized from cyclohexane).
IR(KBr)cm$^{-1}$: 1518, 1330, 1159, 1121, 1069, 837.
NMR(CDCl$_3$)δ: 1.65–1.91(4H,m), 2.94–2.99(2H,m), 3.14(2H,t,J=5Hz), 4.00(1H,br.s),7.61 (2H,d,J=8Hz), 7.86(2H,d,J=8Hz).
Elemental analysis for C$_{14}$H$_{13}$N$_2$SF$_3$:
Calculated: C, 56.36; H, 4.39; N, 9.39; S, 10.75; F, 19.10.
Found C, 56.39; H, 4.33; N, 9.40; S, 10.78; F, 18.92.

EXAMPLE 65

2-(3,4-Methylenedioxyphenyl)-5,6,7,8-tetrahydro-4H-thiazolo-[5,4-b]azepine hydrochloride By the method of Example 1, the title compound was obtained by reacting 3-(3,4-methylenedioxybenzoyl)amino-ε-caprolactam and phosphorus pentasulfide, purifying and neutralizing with hydrogen chloride.
Yield 27.2%.
m.p. 190–192° (recrystallized from a mixture of methanol and ethyl ether).
IR(KBr)cm$^{-1}$: 3196, 1619, 1602, 1506, 1348, 1266.
NMR(CDCl$_3$)δ: 1.68–1.90(4H,m), 3.17–3.28(4H,m), 6.04(2H,s), 6.85(1H,d,J=8Hz), 7.56 (1H,s), 7.65(1H,d,J=8Hz).
Elemental analysis for C$_{14}$H$_{15}$N$_2$O$_2$SCl:
Calculated: C, 54.10; H, 4.86; N, 9.01; S, 10.32; Cl, 11.41.
Found C, 53.72; H, 4.99; N, 8.85; S, 10.26; Cl, 11.13.

EXAMPLE 66

2-(p-Tolyl)-5,6,7,8-tetrahydro-4H-thiazolo[5,4-b]azepine

The title compound was obtained by reacting 3-(p-toluoyl)amino-ε-caprolactam and phosphorus pentasulfide in the method described in Example 1.
Yield 43.4%.
m.p. 128–129° (recrystallized from cyclohexane).
IR(KBr)cm$^{-1}$: 3236, 3018, 2918, 1516, 1460, 1372, 816.
NMR(CDCl$_3$)δ: 1.61–1.89(4H,m), 2.35(3H,s), 2.91–2.97(2H,m), 3.11(2H,t,J=5Hz), 7.11 (2H,d,J=8Hz), 7.65(2H,d,J=8Hz).
Elemental analysis for C$_{14}$H$_{16}$N$_2$S:
Calculated: C, 68.81; H, 6.60; N, 11.46; S, 13.12.
Found C, 68.57; H, 6.60; N, 11.62; S, 13.28.

EXAMPLE 67

2-4-(tert-Butoxycarbonylaminomethyl)phenyl)-5,6,7,8-tetrahydro-4H-thiazolo[5,4-b]azepine The title compound was obtained by reacting 3-[4-(tert-butoxycarbonylaminomethyl)benzoyl]amino-ε-caprolactam and phosphorus pentasulfide in the method described in Example 1.
Yield 19.6%.
m p. 170–171° (recrystallized from ethyl acetate).
IR(KBr)cm$^{-1}$: 3312, 1673, 1524, 1368, 1269, 1167.
NMR(CDCl$_3$)δ: 1.46(9H,s), 1.64–1.90(4H,m), 2.94(2H, t,J=6Hz), 3.11(2H,t,J=5Hz), 4.31(2H,d, J=6Hz), 7.27(2H,d,J=8Hz), 7.72(2H,d,J=8Hz).
Elemental analysis for C$_{19}$H$_{25}$N$_3$O$_2$S:
Calculated: C, 63.48; H, 7.01; N, 11.69; S, 8.92.
Found: C, 63.47; H, 7.07; N, 11.78; S, 8.86.

EXAMPLE 68

2,3,4-Trimethoxyphenyl)-5,6,7,8-tetrahydro-4H-thiazolo-[5,4-b]azepine

The title compound was obtained by reacting 3-(2,3,4-trimethoxybenzoyl)amino-ε-caprolactam and phosphorus pentasulfide in the method described in Example 1.
Yield 18.9%.
m.p. 133–134° (recrystallized from ethanol).
IR(KBr)cm$^{-1}$: 2934, 1553, 1498, 1437, 1290, 1092.
NMR(CDCl$_3$)δ: 1.60–1.90(4H,m), 2.95(2H,t,J=6Hz), 3.11(2H,t,J=5Hz), 3.89(6H,s), 3.96 (3H,s), 6.74(1H,d,J=9Hz), 7.89(1H,d, J=9Hz).
Elemental analysis for C$_{16}$H$_{20}$N$_2$O$_3$S:
Calculated: C, 59.98; H, 6.29; n, 8.74; S, 10.01.
Found C, 59.94; H, 6.36; n, 8.63; S, 9.95.

EXAMPLE 69

2-(3-Trifluoromethylstyryl)-5,6,7,8-tetrahydro-4H-thiazolo[5,4-b]azepine

The title compound was obtained by reacting 3-(3-trifluoromethylcinnamoyl)amino-ε-caprolactam and phosphorus pentasulfide in the method described in Example 1.
Yield 51.0%.
m.p. 151–152° (recrystallized from cyclohexane).
IR(KBr)cm$^{-1}$: 3260, 1546, 1517, 1334, 1160, 1124.
NMR(CDCl$_3$)δ: 1.63–1.89(4H,m), 2.88–2.94(2H,m), 3.13(2H,t,J=5Hz), 4.02(1H,br.s),7.01 (1H,d,J=16Hz), 7.15(1H,d,J=16Hz), 7.43–7.68(4H,m).
Elemental analysis for C$_{16}$H$_{15}$N$_2$SF$_3$:
Calculated: C, 59.25; H, 4.66; N, 8.64; S, 9.89; F, 17.57.
Found: C, 59.20; H, 4.63; N, 8.53; S, 9.67; F, 17.39.

EXAMPLE 70

2-[2-(tert-Butoxycarbonylamino)ethyl]-5,6,7,8-tetrahydro-4H-thiazolo[5,4-b]azepine The title compound was obtained by reacting 3-(N-tert-butoxycarbonyl-β-alanyl)amino-ε-caprolactam and phosphorus pentasulfide in the method described in Example 1.
Yield 27.2%.
m.p. 152–153° (recrystallized from ethyl acetate).
IR(KBr)cm$^{-1}$: 2924, 1688, 1547, 1282, 1262, 1161.
NMR(d$_6$—DMSO)δ: 1.44(9H,s), 1.56–1.87(4H,m), 2.81–2.87(2H,m), 2.94(2H,t,J=6Hz), 3.05 (2H,t,J=5Hz), 3.41–3.52(2H,m).
Elemental analysis for C$_{14}$H$_{23}$N$_3$O$_2$S:
Calculated: C, 56.54; H, 7.79; N, 14.13; S, 10.78.
Found: C, 56.51; H, 7.91; N, 14.17; S, 10.79.

EXAMPLE 71

2-(4-Methoxycarbonylphenyl)-5,6,7,8-tetrahydro-4H-thiazolo [5,4-b]azepine

The title compound was obtained by reacting 3-(4-methoxycarbonylbenzoyl)amino-ε-caprolactam and phosphorus pentasulfide in the method described in Example 1.

Yield 56.6%.

m.p. 168-170° (recrystallized from methanol).

IR(KBr)cm$^{-1}$: 1730, 1510, 1441, 1274, 1175, 1114.

NMR(CDCl$_3$)δ: 1.45-1.98(4H,m), 2.90-3.02(2H,m), 3.07-3.18(2H,m), 3.92(3H,s), 7.78 (2H,d,J=9Hz), 8.01(2H,d,J=9Hz).

Elemental analysis for C$_{15}$H$_{16}$N$_2$O$_2$S:

Calculated: C, 62.48; H, 5.59; N, 9.71; S, 11:12.

Found C, 62.39; H, 5.59; N, 9.87; S, 11.11.

EXAMPLE 72

2-(4-Ethoxycarbonylstyryl)-5,6,7,8-tetrahydro-4H-thiazolo [5,4-b]azepine

The title compound was obtained by reacting 3-(4-ethoxycarbonylcinnamoyl)amino-ε-caprolactam and phosphorus pentasulfide in the method described in Example 1.

Yield 8.7%.

m.p. 149-150° (recrystallized from ethyl acetate).

IR(KBr)cm$^{-1}$: 1715, 1522, 1356, 1275, 1252, 1104.

NMR(CDCl$_3$)δ: 1.39(3H,t,J=7Hz), 1.60-1.86(4H,m), 2.88-2.94(2H,m), 3.11-3.15(2H,m), 4.38(2H,q,J=7Hz), 7.01(1H,d,J=16Hz), 7.18(1H,d,J=16Hz), 7.50(2H,d,J=8Hz), 8.01(2H,d,J=8Hz).

Elemental analysis for C$_{18}$H$_{20}$N$_2$O$_2$S:

Calculated: C, 65.83; H, 6.14; N, 8.53; S, 9.76.

Found C, 65.87; H, 6.10; N, 8.62; S, 9.62.

EXAMPLE 73

2-[1-(tert-Butoxycarbonylamino)ethyl]-5,6,7,8-tetrahydro-4H-thiazolo[5,4-b]azepine The title compound was obtained by reacting N-tert-butoxycarbonylalanine, 3-amino-ε-caprolactam and phosphorus pentasulfide in the method described in Example 18.

Yield 8.3%.

m.p. 180-182° (recrystallized from ethyl acetate).

IR(KBr)cm$^{-1}$: 3244, 1694, 1513, 1368, 1248, 1171.

NMR(CDCl$_3$)δ: 1.45(9H,s), 1.52(3H,d,J=7Hz), 1.56-1.86(4H,m), 2.84(2H,t,J=6Hz), 3.05 (2H,m), 4.78-4.90(1H,m).

Elemental analysis for C$_{14}$H$_{23}$N$_3$O$_2$S:

Calculated C, 56.54; H, 7.79; N, 14.13; S, 10.78.

Found C, 56.70; H, 7.81; N, 14.11; S, 10.78.

EXAMPLE 74

2-(4-Pyridyl)-5,6,7,8-tetrahydro-4H-thiazolo5,4-b]azepine

The title compound was obtained by reacting isonicotinic acid, 3-amino-ε-caprolactam and phosphorus pentasulfide in the method described in Example 18.

Yield 42.0%.

m.p. 169-170° (recrystallized from cyclohexane).

IR(KBr)cm$^{-1}$: 1597, 1528, 1498, 1439, 1372, 1360.

NMR(CDCl$_3$)δ: 1.60-1.98(4H,m), 2.90-3.00(2H,m), 3.06-3.18(2H,m), 4.11(1H,br.s), 7.60 (2H,d,J=6Hz), 8.56(2H,d,J=6Hz).

Elemental analysis for C$_{12}$H$_{13}$N$_3$S:

Calculated: C, 62.31; H, 5.66; N, 18.17; S, 13.86.

Found C, 62.45; H, 5.64; N, 18.07; S, 13.82.

EXAMPLE 75

2-(3-Hydroxy-4-methoxystyryl)-5,6,7,8-tetrahydro-4H-thiazolo-[5,4-b]azepine hydrochloride 2-(3-Ethoxycarbonyloxy-4-methoxystyryl)-5,6,7,8-tetrahydro-4H-thiazolo[5,4-b]azepine (13.2 g) was added to a solution of 1N ammonia in methanol (600 ml), and and the whole was stirred for 3 hrs. at room temperature. The solvent was distilled off under reduced pressure and the residue was purified by a column chromatography on silica gel to give 2-(3-hydroxy-4-methoxystyryl)-5,6,7, 8-tetrahydro-4H-thiazolo [5,4-b]azepine (yield 8.74 g, 81.9%). The product (1.50 g) was converted into its hydrochloride which was recrystallized from a mixture of methanol and ethyl ether to give the title compound (0.49 g, 29.0 %). m.p. 210-211°.

IR(KBr)cm$^{-1}$: 2530, 1601, 1504, 1279, 947.

NMR(d$_6$—DMSO)δ: 1.56-1.79(4H,m), 2.76-2.87(2H,m), 3.02-3.10(2H,m), 3.81(3H,s), 6.94-7.12(4H,m), 7.31(1H,d,J=16Hz).

Elemental analysis for C$_{16}$H$_{19}$N$_2$O$_2$SCl:

Calculated: C, 56.71; H, 5.65; N, 8.27; S, 9.46.

Found C, 56.72; H, 5.63; N, 8.30; S, 9.60.

EXAMPLE 76

2-(4-Hydroxyphenyl)-5,6,7,8-tetrahydro-4H-thiazolo[5,4-b]-azepine hydrochloride

The title compound was obtained by treating 2-(4-ethoxycarbonyloxyphenyl)-5,6,7,8-tetrahydro-4H-thiazolo [5,4-b]azepine in the method described in Example 75.

Yield 32.5%.

m.p. 215-216° (recrystallized from a mixture of ethanol and ethyl ether).

IR(KBr)cm$^{-1}$: 3378, 2926, 1607, 1560, 1519, 1279, 1238.

NMR(d$_6$—DMSO)δ: 1.56-1.82(4H,m), 2.83-2.93(2H,m), 3.00-3.11(2H,m), 6.89(2H,d,J=8Hz), 7.73(2H,d,J=8Hz).

Elemental analysis for C$_{13}$H$_{15}$N$_2$OSCl:

Calculated: C, 55.21; H, 5.35; N, 9.91; S, 11.34; Cl, 12.54.

Found C, 55.19; H, 5.41; N, 9.74; S, 11.10; Cl, 12.50.

EXAMPLE 77

2-(2-Aminoethyl)-5,6,7,8-tetrahydro-4H-thiazolo[5,4-b]-azepine dihydrochloride

A solution (3 ml) of 4.75N hydrochloric acid in methanol was added to a solution (10 ml) of 2-[2-(tert-butoxycarbonyl- amino)ethyl]-5,6,7,8-tetrahydro-4H-thiazolo -[5,4-b]azepine (1.00 g) in methanol, and the whole was stirred for 5 hrs. at room temperature. The solvent was distilled off under reduced pressure. The residue was washed with ethyl ether, and recrystallized from a mixture of methanol and ethyl ether to give the title compound (0.64 g, 70.5%).

m.p. 206-208°.

IR(KBr)cm$^{-1}$: 3254, 2938, 2844, 2796, 1616, 1531, 1500.

NMR(d$_6$—DMSO)δ: 1.52-1.85(4H,m), 2.79-2.84(2H,m), 2.99-3.05(2H,m), 3.19-3.28(4H,m).

Elemental analysis for C$_9$H$_{17}$N$_3$SCl$_2$:

Calculated: C, 40.00; H, 6.34; N, 15.55; S, 11.87.

Found: C, 39.89; H, 6.29; N, 15.24; S, 11.87.

EXAMPLE 78

2-(4-Aminomethylphenyl)-5,6,7,8-tetrahydro-4H-thiazolo [5,4-b]azepine dihydrochloride

The title compound was obtained by treating 2-[4-(tert-butoxycarbonylaminomethyl)phenyl]-5,6,7,8-tetra-hydro -4H-thiazolo[5,4-b]azepine in the method of Example 77.

Yield 65.4%.

m.p. 263-265° (recrystallized from methanol).

IR(KBr)cm$^{-1}$: 3224, 2930, 1606, 1531, 1467, 1372, 1125.

NMR(d$_6$—DMSO)δ: 1.56-1.86(4H,m), 2.87-2.93(2H,m), 3.02-3.08(2H,m), 4.01-4.07(2H,m), 7.57(2H,d,J=8Hz), 7.85(2H,d,J=8Hz).

Elemental analysis for $C_{14}H_{19}N_3SCl_2$:

Calculated: C, 50.60; H, 5.76; N, 12.65; S, 9.65; Cl, 21.34.

Found: C, 50.77; H, 5.73; N, 12.63; S, 9.56; Cl, 21.26.

EXAMPLE 79

2-(4-Methoxy-3-pentyloxystyryl)-5,6,7,8-tetrahydro-4H-thiazolo[5,4-b]azepine

Amyl bromide (0.49 ml) and potassium carbonate (0.46 g) were added to a solution (20 ml) of 2-(3-hydroxy-4-methoxy-styryl)-5,6,7,8-tetrahydro-4H-thiazolo[5,4-b]azepine (1.00 g) in dimethylformamide, and the whole was stirred for 1 hr. at 100°. After cooling, the reaction mixture was washed with water, dried and concentrated under reduced pressure. The residue was purified by a column chromatography on silica gel, and recrystallized from isopropyl ether to give the title compound (0.19 g, 15.4%). m.p. 124-125°.

IR(KBr)cm$^{-1}$: 3240, 2930, 1515, 1451, 1263, 1236, 1022.

NMR(CDCl$_3$)δ: 0.94(3H,t,J=7Hz), 1.36-1.93(10H,m), 2.89(2H,t,J=5Hz), 3.12(2H,t), 3.88(3H,s), 4.03(2H,q,J=7Hz), 6.84(1H,d,J=8Hz), 6.96-7.04(4H,m).

Elemental analysis for $C_{21}H_{28}N_2O_2S$:

Calculated: C, 67.71; H, 7.58; N, 7.52.

Found C, 67.49; H, 7.43; N, 7.39.

EXAMPLE 80

4-Methyl-2-phenyl-5,6,7,8-tetrahydro-4H-thiazolo[5,4-b]-azepine hydrochloride

Methyl iodide (0.45 ml) and potassium carbonate (0.75 g) were added to a solution of 2-phenyl-5,6,7,8-tetrahydro-4H-thiazolo[5,4-b]azepine (0.83 g) in dimethylformamide (30 ml), and the whole was stirred for 4.5 hrs. at 90°. After cooling, the reaction mixture was filtered, and the filtrate was dissolved in ethyl ether. The solution was washed with water, dried and concentrated under reduced pressure. The residue was purified by a column chromatography on silica gel, neutralized with hydrogen chloride and recrystallized from a mixture of ethanol and ethyl ether to give the title compound (0.53 g, 52.4%). m.p. 139-140°.

IR(KBr)cm$^{-1}$: 3218, 2928, 2564, 1591, 1524, 1425, 1319, 767.

NMR(d$_6$—DMSO)δ: 1.43-2.00(4H,m), 2.76-3.16(7H,m), 7.30-7.52(3H,m), 7.70-7.93(2H,m).

Elemental analysis for $C_{14}H_{17}N_2SCl$:

Calculated: C, 59.88; H, 6.10; N, 9.98; S, 11.43.

Found C, 59.70; H, 6.00; N, 9.86; S, 11.51.

EXAMPLE 81

4-Allyl-2-(4-methoxy-3-methylstyryl)-5,6,7,8-tetrahydro-4H-thiazolo[5,4-b]azepine hydrochloride

By using the method of Example 80, the title compound was obtained by reacting 2-(4-methoxy-3-methyl-styryl)-5,6,7,8-tetrahydro-4H-thiazolo5,4-b]azepine, allyl bromide and potassium carbonate, purifying and neutarlizing with hydrogen chloride.

Yield 56.4%.

m.p 162-163° (recrystallized from a mixture of ethanol and ethyl ether).

IR(KBr)cm$^{-1}$: 2934, 2346, 1589, 1501, 1439, 1254, 1132.

NMR(d$_6$—DMSO)δ: 1.54-1.68(2H,m), 1.73-1.88(2H,m), 2.17(3H,s), 2.81-2.90(2H,m), 3.09-3.18(2H,m), 3.74-3.89(5H,m), 5.26-5.40(2H,m), 5.83-6.02(1H,m), 6.97 (1H,d,J=9Hz), 7.14(1H,d,J=16Hz), 7.30 (1H,d,J=16Hz), 7.41-7.45(2H,m).

Elemental analysis for $C_{20}H_{25}N_2OSCl$:

Calculated: C, 63.73; H, 6.68; N, 7.43; S, 8.51; Cl, 9.41.

Found: C, 63.79; H, 6.60; N, 7.41; S, 8.51; Cl, 9.49

EXAMPLE 82

2-(2,6-Difluorophenyl)-4-methyl-5,6,7,8-tetrahydro-4H-thiazolo[5,4-b]azepine hydrochloride

By using the method of Example 80, the title compound was obtained by reacting 2-(2,6-difluorophenyl)-5,6,7,8-tetrahydro-4H-thiazolo[5,4-b]azepine, methyl iodide, purifying and neutralizing with hydrogen chloride.

Yield 44.3%.

m.p. 132-133° (recrystallized from a mixture of methanol and ethyl ether).

IR(KBr)cm$^{-1}$: 2396, 1622, 1585, 1530, 1470, 1011, 806.

NMR(CDCl$_3$)δ: 1.70-1.82(2H,m), 1.91-2.04(2H,m), 3.09(3H,s), 3.20(2H,t,J=5Hz), 3.37(2H, t,J=6Hz), 7.12(2H,t,J=8Hz), 7.45-7.60 (1H,m).

Elemental analysis for $C_{14}H_{15}N_2SF_2Cl$:

Calculated: C, 53.08; H, 4.77; N, 8.84; S, 10.12; F, 11.99; Cl, 11.19.

Found: C, 53.16; H, 4.71; N, 8.86; S, 10.26; F, 12.10; Cl, 11.15.

EXAMPLE 83

2-(2,6-Difluorophenyl)-4-ethyl-5,6,7,8-tetrahydro-4H-thiazolo[5,4-b]azepine

The title compound was obtained by reacting 2-(2,6-difluorophenyl)-5,6,7,8-tetrahydro-4H-thiazolo[5,4-b]azepine, ethyl bromide and potassium carbonate in the method described in Example 80.

Yield 4.2%.

m.p. 51-52° (recrystallized from mixture of methanol and water).

IR(KBr)cm$^{-1}$: 1524, 1498, 1461, 1432, 1371, 992, 796.

NMR(CDCl$_3$)δ: 1.25(3H,t,J=8Hz), 1.50-1.98(4H,m), 2.92-3.09(4H,m), 3.24(2H,q,J=8Hz), 6.95-7.40(3H,m).

Elemental analysis for $C_{15}H_{16}N_2SF_2$:

Calculated: C, 61.20; H, 5.48; N, 9.52; S, 10.89; F, 12.91

Found: C, 61.04; H, 5.40; N, 9.58; S, 10.63; F, 13.06

EXAMPLE 84

4-Allyl-2-(2,6-Difluorophenyl)-5,6,7,8-tetrahydro-4H-thiazolo[5,4-b]azepine

The title compound was obtained by reacting 2-(2,6-difluorophenyl)-5,6,7,8-tetrahydro-4H-thiazolo5,4-b]-azepine, allyl bromide and potassium carbonate in the method described in Example 80.

Yield 44.3%.

m.p. 68° (recrystallized from petroleum ether).

IR(KBr)cm$^{-1}$: 1531, 1467, 1412, 1352, 1243, 1008.

NMR(CDCl$_3$)δ: 1.62–1.90(4H,m), 2.99–3.09(4H,m), 3.78–3.82(2H,m), 5.25(1H,dd,J=2Hz, 10Hz), 5.32(1H,dd,J=2Hz, 10Hz), 5.84–6.04(1H,m), 6.93–7.02(2H,m), 7.19–7.28(1H,m).

Elemental analysis for C$_{16}$H$_{16}$N$_2$SF$_2$:

Calculated: C, 62.72; H, 5.26; N, 9.14; S, 10.47; F, 12.40.

Found: C, 62.87; H, 5.24; N, 9.14; S, 10.48; F, 12.30.

EXAMPLE 85

4-(Ethoxycarbonylmethyl)-2-(4-methoxyphenyl)-5,6,7,8-tetrahydro-4H-thiazolo[5,4-b]azepine hydrochloride By the method of Example 80, the title compound was obtained by reacting 2-(4-methoxyphenyl)-5,6,7,8-tetrahydro-4H-thiazolo[5,4-b]azepine hydrochloride, ethyl bromoacetate and potassium carbonate, purifying and neutralizing with hydrogen chloride.

Yield 20.1% m.p. 110–111° (recrystallized from a mixture of methanol and ethyl ether).

IR(KBr)cm$^{-1}$: 1733, 1596, 1531, 1271, 1260, 1188.

NMR(d$_6$—DMSO)δ: 1.34(3H,t,J=7Hz), 1.69–1.96(4H,m), 3.25–3.30(2H,m), 3.35–3.40(2H,m), 3.87 (3H,s), 4.01(2H,s), 4.30(2H,q,J=7Hz), 7.02(2H,d,J=9Hz), 8.22(2H,d,J=9Hz).

Elemental analysis for C18H$_{23}$N$_2$O$_3$SCl:

Calculated : C, 56.46; H, 6.05; N, 7.32; S, 8.37; Cl, 9.26.

Found: C, 56.61; H, 5.83; N, 7.38; S, 8.40; Cl, 9.19.

EXAMPLE 86

4-Acetyl-2-(3,5-di-tert-butyl-4-hydroxyphenyl)-5,6,7,8-tetrahydro-4H-thiazolo[5,4-b]azepine The title compound was obtained by reacting 2-(3,5-di-t-butyl-4-hydroxyphenyl)-5,6,7,8-tetrahydro-4H-thiazolo [5,4-b]azepine, triethylamine and acetic anhydride in the method described in Example 40.

Yield 56.0%.

m.p. 198–199°.

IR(KBr)cm$^{-1}$: 3542, 2954, 2924, 1666, 1406, 1385, 1107.

NMR(CDCl$_3$)δ: 1.48(18H,s), 1.58–2.02(4H,m), 2.13(3H,s), 2.93(2H,t), 3.68(2H,t), 5.45(1H,s), 7.68(2H,s).

Elemental analysis for C$_{23}$H$_{32}$N$_2$SO$_2$:

Calculated: C, 68.96; H, 8.05; N, 6.99; S, 8.00.

Found C, 68.76; H, 7.99; N, 6.70; S, 8.00.

EXAMPLE 87

2-(3-Methoxy-4-methylthiomethoxystyryl)-5,6,7,8-tetrahydro-4H-thiazolo[5,4-b]azepine The title compound was obtained by reacting 3-methoxy-4-methylthiomethoxycinnamic acid, 3-amino-ε-caprolactam and phosphorus pentasulfide in the method described in Example 18.

Yield 10.7%.

m.p 11714 119°.

IR(KBr)cm$^{-1}$: 1533, 1509, 1445, 1370, 1256.

NMR(CDCl$_3$)δ: 1.67(2H,m), 1.82(2H,m), 2.27(3H,s), 2.89(2H,t), 3.12(2H,t), 3.90(3H,s), 5.26(2H,s), 6.99(5H,m).

Elemental analysis for C$_{18}$H$_{22}$N$_2$S$_2$O$_2$:

Calculated: C, 59.64; H, 6.12; N, 7.73; S, 17.69.

Found: C, 59.57; H, 6.22; N, 7.55; S, 17.62.

EXAMPLE 88

2-(4-Hydroxy-3-methoxystyryl)-5,6,7,8-tetrahydro-4H-thiazolo[5,4-b]azepine 2-(3-Methoxy-4-methylthiomethoxystyryl)-5,6,7,8-tetrahydro-4H-thiazolo[5,4-b]azepine (1.88 g) obtained in Example 87, was dissolved in a mixture of dimethylformamide, acetonitrile and water, following by addition of mercuric chloride (2.11 g). The mixture was refluxed for 15 hrs. After completing the reaction, an aqueous sodium hydrogen carbonate was added to the mixture. The mixture was extracted with a mixture of chloroform and methanol, dried over anhydrous magnesium sulfate and distilled under reduced pressure to remove the solvent. The residue was subjected to a column chromatography on silica gel eluting a mixture of chloroform and methanol (98:2, v/v) to give the title compound (yield 318 mg).

m.p. 175–178°.

IR(KBr)cm$^{-1}$: 3394, 1549, 1515, 1462, 1369, 1263, 1036.

NMR(CDCl$_3$)δ: 1.67(2H,m). 1.83(2H,m), 2.90(2H,t), 3.12(2H,t), 3.90(1H,s), 3.91(3H,s), 6.85–7.05(5H,m).

Elemental analysis for C$_{16}$H$_{18}$N$_2$SO$_2$·0.5H$_2$O:

Calculated: C, 61.71; H, 6.15; N, 9.00; S, 10.30.

Found: C, 62.12; H, 5.90; N, 8.91; S, 10.45.

EXAMPLE 89

2-(2-Pyradinyl)-5,6,7,8-tetrahydro-4H-thiazolo[5,4-b]azepine

The title compound was obtained by reacting 2-pyradinecarboxylic acid, 3-amino-ε-caprolactam and phosphorus pentasulfide in the method described in Example 18.

Yield 34.9%.

m.p. 196–198° (recrystallized from ethyl acetate).

IR(KBr)cm$^{-1}$: 3298, 1485, 1353, 1291, 1146, 753.

NMR(CDCl$_3$)6: 1.73(2H,m), 1.86(2H,m), 2.98(2H,t), 3.17(2H,t), 4.29(1H,brs), 8.43(2H,s), 9.26(1H,s).

Elemental analysis for C$_{11}$H$_{12}$N$_2$S:

Calculated: C, 56.87; H, 5.21; N, 24.12; S, 13.80.

Found: C, 56.97; H, 5.23; N, 24.03; S, 13.86.

EXAMPLE 90

2-(2-Indolyl)-5,6,7,8-tetrahydro-4H-thiazolo[5,4-b]azepine

The title compound was obtained by reacting indole-2-carboxylic acid, 3-amino-ε-caprolactam and phosphorus pentasulfide in the method described in Example 18.

Yield 35.3%.

m.p. 198–200°.

IR(KBr)cm$^{-1}$: 3226, 1551, 1503, 1456, 1366, 1353, 1298, 1257, 1142.

NMR(d₆—DMSO)δ: 1.63(2H,m), 1.74(2H,m), 2.84(2H,t), 3.01(2H,t), 6.63(1H,s), 6.91–7.14 (2H,m), 7.38(1H,d,J=7.65Hz) 7.47(1H,d), 11.46(1H,br.s).
Elemental analysis for $C_{15}H_{15}N_3S$
Calculated: C, 66.88; H, 5.61; N, 15.60; S, 11.90.
Found: C, 66.91; H, 5.53; N, 15.40; S, 11.92.

EXAMPLE 91

2-(4-Dimethylaminophenyl)-5,6,7,8-tetrahydro-4H-thiazolo[5,4-b]azepine

The title compound was obtained by reacting 4-dimethylaminobenzoic acid, 3-amino-ε-caprolactam and phosphorus pentasulfide in the method described in Example 18.
Yield 11.5%.
m.p. 152–154° (recrystallized from ethyl acetate).
IR(KBr)cm⁻¹: 3252, 1609, 1557, 1524, 1483, 1467, 1444, 1358, 1269, 1170.
NMR(CDCl₃)δ: 1.68(2H,m), 1.81(2H,m), 2.92(2H,t), 3.08(2H,t), 2.98(6H,s), 6.68(2H,d, J=9.0Hz), 7.64(2H,d).
Elemental analysis for $C_{15}H_{19}N_3S$:
Calculated: C, 65.90; H, 7.00; N, 15.37; S, 11.73.
Found: C, 65.90; H, 6.89; N, 15.25; S, 12.03.

EXAMPLE 92

2-(4-Methylthiostyryl)-5,6,7,8-tetrahydro-4H-thiazolo[5,4-b]azepine

The title compound was obtained by reacting 4-methylthio-cinnamic acid, 3-amino-ε-caprolactam and phosphorus pentasulfide in the method described in Example 18.
Yield 57.5%.
m.p. 157–159°.
IR(KBr)cm⁻¹: 3260, 1621, 1545, 1430, 1353, 1091, 949.
NMR(CDCl₃)δ: 1.67(2H,m), 1.82(2H,m), 2.49(3H,s), 2.89(2H,t), 3.11(2H,t), 7.01(2H,q), 7.21(2H,d,J=8.5Hz), 7.38(2H,d).
Elemental analysis for $C_{16}H_{18}N_2S_2$:
Calculated: C, 63.54; H, 6.00; N, 9.26; S, 21.20.
Found: C, 63.31; H, 5.92; N, 9.27; S, 21.36.

EXAMPLE 93

2-[2-(2-Furyl)ethenyl]-5,6,7,8-tetrahydro-4H-thiazolo[5,4-b]azepine

The title compound was obtained by reacting 8-(2-furyl)-acrylic acid, 3-amino-ε-caprolactam and phosphorus pentasulfide in the method described in Example 18.
Yield 14.0%.
m.p. 125–128°.
IR(KBr)cm⁻¹: 3260, 1547, 1422, 1351, 944, 736.
NMR(CDCl₃)δ: 1.68(2H,m), 1.81(2H,m), 2.89(2H,t), 3.11(2H,t), 6.40(2H,m), 6.91(2H,q), 7.40(1H,d).
Elemental analysis for $C_{13}H_{14}N_2SO$:
Calculated: C, 63.39; H, 5.73; N, 11.37; S, 13.02.
Found: C, 62.87; H, 5.58; N, 11.17; S, 13.46.

EXAMPLE 94

2-[2-(4-Methoxyphenyl)ethyl]-5,6,7,8-tetrahydro-4H-thiazolo[5,4-b]azepine

The title compound was obtained by reacting 4-methoxyphenylpropionic acid, 3-amino-ε-caprolactam and phosphorus pentasulfide in the method described in Example 18.
Yield 26.0%.
m.p. 80–83°.
IR(KBr)cm⁻¹: 161, 1584, 1513, 1486, 1437, 1247, 1178, 1037.
NMR(CDCl₃)δ: 1.64(2H,m), 1.79(2H,m), 2.83–3.10 (8H ,m), 3.79(3H,s), 6.84(2H,d,J=8.6Hz), 7.14(2H,d).
Elemental analysis for $C_{16}H_{20}N_2SO \cdot 0.5H_2O$:
Calculated: C, 64.61; H, 7.12; N, 9.42; S, 10.78.
Found: C, 64.86; H, 6.87; N, 9.48; S, 11.02.

EXAMPLE 95

2-(4-Biphenylyl)-5,6,7,8-tetrahydro-4H-thiazolo[5,4-b]azepine

The title compound was obtained by reacting 4-phenylbenzoic acid, 3-amino-ε-caprolactam and phosphorus pentasulfide in the method described in Example 18.
Yield 60.0%.
m.p. 180–183°.
IR(KBr)cm⁻¹: 3232, 1520, 1490, 1445, 1371, 765, 692.
NMR(CDCl₃)δ: 1.71(2H,m), 1.84(2H,m), 2.97(2H,t, 3.13(2H,t), 7.30–7.50(3H,m), 7.61 (4H,m), 7.84(2H,d).
Elemental analysis for $C_{19}H_{18}N_2S$:
Calculated: C, 74.47; H, 5.92; N, 9.14; S, 10.46.
Found: C, 74.04; H, 5.78; N, 8.86; S, 10.66.

EXAMPLE 96

2-(4-Dimethylaminostyryl)-5,6,7,8-tetrahydro-4H-thiazolo-[5,4-b]azepine

The title compound was obtained by reacting 4-dimethylaminocinnamic acid, 3-amino-ε-caprolactam and phosphorus pentasulfide in the method described in Example 18.
Yield 16.3%
m.p. 207–210° (recrystallized from ethyl acetate).
IR(KBr)cm⁻¹: 3274, 1604, 1548, 1525, 1443, 1365, 1165.
NMR(CDCl₃)δ: 1.67(2H,m). 1.81(2H,m), 2.88(2H,t), 3.09(2H,t), 2.98(6H,s), 6.68(2H,d, J=8.91Hz), 6.93(2H,d), 7.36(2H,d).
Elemental analysis for $C_{17}H_{21}N_3S \cdot 0.4H_2O$:
Calculated: C, 66.59; H, 7.17; N, 13.70; S, 10.46.
Found: C, 66.77; H, 6.93; N, 13.62; S, 10.85.

EXAMPLE 97

2-(3-Dimethylaminophenyl)-5,6,7,8-tetrahydro-4H-thiazolo[5,4-b]azepine

The title compound was obtained by reacting 2-dimethylaminobenzoic acid, 3-amino-ε-caprolactam and phosphorus pentasulfide in the method described in Example 18.
Yield 34.9%
m.p 164–166° (recrystallized from ethyl acetate).
IR(KBr)cm⁻¹: 3228, 1599, 1557, 1502, 1436, 1371, 1356, 1267.
NMR(CDCl₃)δ: 1.69(2H,m), 1.83(2H,m), 2.95(2H,t), 3.10(2H,t), 2.99(6H,s), 6.71(1H,d), 7.04–7.29(3H,m).
Elemental analysis for $C_{15}H_{19}N_3S$:
Calculated: C, 65.90; H, 7.00; N, 15.37; S, 11.73.
Found: C, 66.06; H, 6.99; N, 15.32; S, 11.86.

EXAMPLE 98

2-[3-(2-Methylthio)pyridyl]-5,6,7,8-tetrahydro-4H-thiazolo[5,4-b]azepine dihydrochloride By using the method of Example 18, the title compound was obtained by reacting 2-(methylthio)nicotinic acid, 3-amino-ε-caprolactam and phosphorus pentasulfide, purifying and neutralizing with hydrogen chloride.
Yield 61.3%
m.p. 142-145°
IR(KBr)cm$^{-1}$: 3424, 1601, 1519, 1466, 1434, 1371, 1248.
NMR(d$_6$—DMSO)δ: 1.70(2H,m), 1.91(2H,m), 2.58(3H,s), 2.98(2H,t), 3.18(2H,t), 7.28(1H,dd), 8.16(1H,d,J=7.73Hz), 8.55(1H,d,J=4.76Hz).
Elemental analysis for C$_{13}$H$_{17}$N$_3$S$_2$Cl:
Calculated: C, 44.57; H, 4.89; N, 11.99; S, 18.31; Cl, 20.24.
Found: C, 44.25; H, 5.03; N, 11.55; S, 17.96; Cl, 19.60.

EXAMPLE 99

2-(4-Diethylaminostyryl)-5,6,7,8-tetrahydro-4H-thiazolo[5,4-b]azepine

The title compound was obtained by reacting 4-diethylaminocinnamic acid, 3-amino-ε-caprolactam and phosphorus pentasulfide in the method described in Example 18.
Yield 23.0%
m.p. 173-175° (recrystallized from ethanol)
IR(KBr)cm$^{-1}$: 3280, 1601, 1547, 1524, 1354, 1272, 1254, 1181, 1158, 962.
NMR(CDCl$_3$)δ: 1.17(6H,t), 1.65(2H,m), 1.81(2H,m), 2.87(2H,t), 3.09(2H,t), 3.37(4H,q), 6.64(2H,d,J=8.61Hz), 6.91(2H,d), 7.33(2H,d).
Elemental analysis for C$_{19}$H$_{25}$N$_3$S:
Calculated: C, 69.68; H, 7.69; N, 12.83; S, 9.79.
Found : C, 69.75; H, 7.76; N, 12.69; S, 9.72.

EXAMPLE 100

2-(4-Methylaminophenyl)-5,6,7,8-tetrahydro-4H-thiazolo[5,4-b]azepine dihydrochloride By the method of Example 18, the title compound was obtained by reacting 4-methylaminobenzoic acid, 3-amino-ε-caprolactam and phosphorus pentasulfide, purifying and neutralizing with hydrogen chloride.
Yield 35.5%.
m.p. 222-225°.
IR(KBr)cm$^{-1}$: 3198, 1600, 1527, 1499.
NMR(CDCl$_3$)δ: 1.64(2H,m), 1.75(2H,m), 2.78(3H,s), 2.95(2H,t), 3.06(2H,t), 6.78(2H,d, J=7.25Hz), 7.86(2H,d).
Elemental analysis for C$_{14}$H$_{19}$N$_3$SCl$_2$:
Calculated: C, 50.60; H, 5.76; N, 12.65.
Found: C, 50.80; H, 5.78; N, 12.54.

EXAMPLE 101

2-(2-Methoxy-cis-styryl)-5,6,7,8-tetrahydro-4H-thiazolo-[5,4-b]azepine

The title compound was obtained by reacting cis-2-methoxycinnamic acid, 3-amino-ε-caprolactam and phosphorus pentasulfide in the method described in Example 18.
Yield 32.1%.
m.p. 167-170° (recrystallized from ethyl acetate).
IR(KBr)cm$^{-1}$: 3278, 1616, 1596, 1539, 1492, 1464, 1431, 1366, 1246, 1105, 1024.
NMR(CDCl$_3$)δ: 1.68(2H,m), 1.80(2H,m), 2.89(2H,t), 3.11(2H,t), 3.88(3H,s), 6.86-7.53(6H,m).
Elemental analysis for C$_{16}$H$_{18}$N$_2$SO:
Calculated: C, 67.10; H, 6.33; N, 9.78; S, 11.20.
Found: C, 66.91; H, 6.30; N, 9.64; S, 11.38.

EXAMPLE 102

2-(2-Amino-5-methylphenyl)-5,6,7,8-tetrahydro-4H-thiazolo[5,4-b]azepine

The title compound was obtained by reacting 2-amino-5-methylbenzoic acid, 3-amino-ε-caprolactam and phosphorus pentasulfide in the method described in Example 18.
Yield 12.6%
m.p. 113-115° (recrystallized from ethyl acetate).
IR(KBr)cm$^{-1}$: 3404, 3350, 3296, 1623, 1558, 1506, 1466, 1365, 1258, 1161.
NMR(CDCl$_3$)δ: 1.68(2H,m), 1.82(2H,m), 2.24(3H,s), 2.90(2H,t), 3.10(2H,t), 6.63(1H,d, J=8.1Hz), 6.89(1H,dd), 7.16(1H,d, J=1.49Hz).
Elemental analysis for C$_{14}$H$_{17}$N$_3$S:
Calculated: C, 64.83; H, 6.61; N, 16.20; S, 12.36.
Found: C, 64.86; H, 6.59; N, 16.43; S, 12.36.

EXAMPLE 103

2-(3-Amino-4-methylphenyl)-5,6,7,8-tetrahydro-4H-thiazolo[5,4-b]azepine

The title compound was obtained by reacting 3-amino-4-methylbenzoic acid, 3-amino-ε-caprolactam and phosphorus pentasulfide in the method described in Example 18.
Yield 32.8%
m.p. 135-137°
IR(KBr)cm$^{-1}$: 3436, 3332, 3226, 1634, 1561, 1500, 1460, 1441, 1368, 1258.
NMR(CDCl$_3$)δ: 1.68(2H,m), 1.82(2H,m), 2.17(3H,s), 2.93(2H,t), 3.10(2H,t), 3.60(2H,brs), 7.04(1H,s), 7.10(2H,d).
Elemental analysis for C$_{14}$H$_{17}$N$_3$S:
Calculated: C, 64.83; H, 6.61; N, 16.20; S, 12.36.
Found: C, 64.58; H, 6.60; N, 16.04; S, 12.12.

EXAMPLE 104

2-(2-Amino-4-chlorophenyl)-5,6,7,8-tetrahydro-4H-thiazolo[5,4-b]azepine

The title compound was obtained by reacting 2-amino-4-chlorobenzoic acid, 3-amino-ε-caprolactam and phosphorus pentasulfide in the method described in Example 18.
Yield 6.7%
m.p. 154-157°
IR(KBr)cm$^{-1}$: 3450, 3384, 1610, 1557, 1491, 1465, 1371, 1264, 1148, 1064.
NMR(CDCl$_3$)δ: 1.68(2H,m), 1.82(2H,m), 2.89(2H,t), 3.10(2H,t), 3.95(1H,brs), 6.12(2H,brs), 6.60(1H,dd), 6.69(1H,d,J=1.91Hz), 7.26 (1H,d,J=8.43Hz).
Elemental analysis for C$_{13}$H$_{14}$N$_3$SCl:
Calculated: C, 55.81; H, 5.04; N, 15.02; S, 11.46; Cl, 12.67.
Found: C, 55.70; H, 5.02; N, 14.87; S, 11.49; Cl, 12.65.

EXAMPLE 105

2-(4-Thioacetaminophenyl)-5,6,7,8-tetrahydro-4H-thiazolo-[5,4-b]azepine

The title compound was obtained by reacting 4-acetaminobenzoic acid, 3-amino-ε-caprolactam and phosphorus pentasulfide in the method described in Example 18.
Yield 10.3%.
m.p. 239-242°.
IR(KBr)cm$^{-1}$: 3434, 1551, 1515, 1496, 1454, 1370.

NMR(d₆—DMSO)δ: 1.59(2H,m), 1.72(2H,m), 2.62(3H,s), 2.80(2H,br.s), 2.98(2H,br.s), 6.25 (1H,br.s), 7.70(2H,d,J=8.65Hz), 7.89 (2H,d), 11.65(1H,br.s).
Elemental analysis for $C_{15}H_{17}N_3S_2$:
Calculated: C, 59.37; H, 5.65; N, 13.85; S, 21.13.
Found: C, 58.92; H, 5.66; N, 13.55; S, 21.23.

EXAMPLE 106

2-(3-Amino-4-methylphenyl)-5,6,7,8-tetrahydro-4H-thiazolo-[5,4-b]azepine dihydrochloride By the method of Example 18, the title compound was obtained by reacting 3-amino-4-methylbenzoic acid, 3-amino-ε-caprolactam and phosphorus pentasulfide, purifying and neutralizing with hydrogen chloride.
Yield 36.4%.
m.p. 170–173°.
IR(KBr)cm⁻¹: 1604, 1561, 1528, 1453, 1371.
NMR(d₆—DMSO)δ: 1.66(2H,m), 1.83(2H,m), 2.41(3H,s), 2.92(2H,t), 3.10(2H,t), 6.35(2H,br.s), 7.37(1H,d,J=8.05Hz), 7.72(2H,m), 7.90(1H,s).
Elemental analysis for $C_{14}H_{19}N_3SCl_2 \cdot 0.5H_2O$:
Calculated: C, 49.27; H, 5.91; N, 12.31; S, 9.40; Cl, 20.77.
Found: C, 49.20; H, 5.57; N, 12.36; S, 9.53; Cl, 20.86.

EXAMPLE 107

2-(2-Pyrrolyl)-5,6,7,8-tetrahydro-4H-thiazolo[5,4-b]azepine dihydrochloride

By the method of Example 18, the title compound was obtained by reacting pyrrole-2-carboxylic acid, 3-amino-ε-caprolactam and phosphorus pentasulfide, purifying and neutralizing with hydrogen chloride.
Yield 18.6%.
m.p. 110–113° (recrystallized from methanol).
IR(KBr)cm⁻¹: 3430, 1631, 1611, 1454, 1372, 1055.
NMR(CDCl₃)δ: 1.67(2H,m), 1.74(2H,m), 2.84(2H,t), 3.08(2H,t), 6.33(1H,dd), 7.10(1H,dd), 7.20(1H,br.s).
Elemental analysis for $C_{11}H_{15}N_3SCl_2$:
Calculated: C, 45.21; H, 5.17; N, 14.38; S, 10.97.
Found: C, 45.46; H, 5.13; N, 14.47; S, 10.94.

EXAMPLE 108

2-(3-Amino-4-methoxyphenyl)-5,6,7,8-tetrahydro-4H-thiazolo [5,4-b]azepine dihydrochloride By the method of Example 18, the title compound was obtained by reacting 3-amino-4-methoxybenzoic acid and phosphorus pentasulfide, purifying and neutralizing with hydrogen chloride.
Yield 13.0%.
m.p. 194–197° (recrystallized from methanol).
IR(KBr)cm⁻¹: 3318, 1603, 1591, 1536, 1485, 1371, 1352, 1289, 1245, 1165, 1035.
NMR(d₆—DMSO)δ: 1.63(2H,m), 1.81(2H,m), 2.90(2H,t), 3.08(2H,t), 3.94(3H,s), 6.05(2H,br.s), 7.27(1H,d,J=8.67Hz), 7.81(1H,dd), 7.88(1H,d,J=2.12Hz).
Elemental analysis for $C_{14}H_{19}N_3SCl_2O$:
Calculated: C, 48.28; H, 5.50; N, 12.06; S, 9.21; Cl, 20.36.
Found: C, 47.80; H, 5.57; N, 11.82; S, 9.23; Cl, 20.17.

EXAMPLE 109

2-(4-Amino-3-methylphenyl)-5,6,7,8-tetrahydro-4H-thiazolo[5,4-b]azepine dihydrochloride By the method of Example 18, the title compound was obtained by reacting 4-amino-3-methylbenzoic acid, 3-amino-ε-caprolactam and phosphorus pentasulfide, purifying the reaction mixture and neutralizing with hydrogen chloride.
Yield 11.3%.
m.p. 240–243° (recrystallized from methanol).
IR(KBr)cm⁻¹: 3246, 2582, 1607, 1521, 1495, 1452, 1374, 1359, 818.
NMR(d₆—DMSO)δ: 1.63(2H,m), 1.76(2H,m), 2.29(3H,s), 2.92(2H,br.s), 3.06(2H,br.s), 6.20 (2H,br.s), 7.18(1H,d,J=8.05Hz), 7.71 (1H,dd,J=1.87Hz), 7.73(1H,br.s).
Elemental analysis for $C_{14}H_{19}N_3SCl_2$:
Calculated: C, 50.60; H, 5.76; N, 12.65; S, 9.65; Cl, 21.34.
Found: C, 50.64; H, 5.85; N, 12.61; S, 9.81; Cl, 21.12.

EXAMPLE 110

2-(2-Amino-6-methylphenyl)-5,6,7,8-tetrahydro-4H-thiazolo[5,4-b]azepine dihydrochloride By the method of Example 18, the title compound was obtained by reacting 2-amino-6-methylbenzoic acid, 3-amino-ε-caprolactam and phosphorus pentasulfide, purifying and neutralizing with hydrogen chloride.
Yield 16.0%
m.p. 189–192° (recrystallized from methanol).
IR(KBr)cm⁻¹: 3256, 2804, 1482, 1603, 1561, 1531, 1468, 1446, 1370, 1355, 1282, 1250.
NMR(d₆-DMSO)δ: 1.68(2H,brs), 1.78(2H,bns), 2.22 (3H,s), 2.89(2H,t), 3.11(2H,t), 5.40(2H,brs), 6.96(1H,d), 7.05(1H,d), 7.30(1H,t).
Elemental analysis for $C_{14}H_{19}N_3SCl_2$:
Calculated: C, 50.60; H, 5.76; N, 12.65; S, 9.65; Cl, 21.34.
Found: C, 50.42; H, 5.93; N, 12.43; S, 9.66; Cl, 21.22.

EXAMPLE 111

2-Methoxycarbonyl-5,6,7,8-tetrahydro-4H-thiazolo[5,4-b]azepine

The title compound was obtained by reacting methyloxalyl chloride, 3-amino-ε-caprolactam and phosphorus pentasulfide in the method described in Example 23.
Yield 19.9%.
m.p. 166–168° (recrystallized from ethyl acetate).
IR(KBr)cm⁻¹: 3412, 3314, 3264, 1716, 1441, 1381, 1241.
NMR(d₆—DMSO)δ: 1.69(2H,m), 1.84(2H,m), 2.98(2H,t), 3.17(2H,t), 3.93(3H,s), 4.46(1H,brs).
Elemental analysis for $C_9H_{12}N_2O_2S$:
Calculated: C, 50.92; H, 5.70; N, 13.20; S, 15.11.
Found: C, 50.98; H, 5.71; N, 13.22; S, 15.25.

EXAMPLE 112

2-(2-Amino-3-methylphenyl)-5,6,7,8-tetrahydro-4H-thiazolo [5,4-b]azepine dihydrochloride By the method of Example 18, the title compound was obtained by reacting 2-amino-3-methylbenzoic acid, 3-amino-ε-caprolactam and phosphorus pentasulfide, purifying and neutralizing with hydrogen chloride.
Yield 38.2%.
m.p 208–211° (recrystallized from methanol).
IR(KBr)cm⁻¹: 3428, 1578, 1542, 1513, 1468, 1308, 1273.
NMR(d₆—DMSO)δ: 1.66(2H,m), 1.81(2H,m), 2.35(3H,s), 2.90(2H,t), 3.08(2H,t), 6.29(2H,brs), 7.07(1H,t), 7.22(1H,d), 7.42(1H,d).
Elemental analysis for $C_{14}H_{19}N_3SCl_2$:

Calculated: C, 50.60; H, 5.76; N, 12.65; S, 9.65; Cl, 21.34.
Found: C, 50.69; H, 5.73; N, 12.58; S, 9.64; Cl, 21.41.

EXAMPLE 113

2-(2-Amino-4,5-dimethoxyphenyl)-5,6,7,8-tetrahydro-4H-thiazolo[5,4-b]azepine dehydrochloride By the method of Example 18, the title compound was obtained by reacting 2-amino-4,5-dimethoxybenzoic acid, 3-amino-ϵ-caprolactam and phosphorus pentasulfide, purifying and neutralizing with hydrogen chloride.

Yield 3.9%.

m.p. 194–197° (recrystallized from methanol).

IR(KBr)cm$^{-1}$: 3444, 1604, 1531, 1462, 1447, 1396, 1362, 1300, 1278, 1262, 1212, 1140, 1079.

NMR(d$_6$—DMSO)δ: 1.63(2H,m), 1.82(2H,m), 2.92(2H,brs), 3.07(2H,brs), 3.81(3H,s), 3.85(3H,s), 7.06(1H,s), 7.10(1H,s), 7.10(2H,brs).

Elemental analysis for C$_{15}$H$_{21}$N$_3$SO$_2$Cl$_2$:

Calculated: C, 47.62; H, 5.59; N, 11.11; S, 8.48; Cl, 18.74.
Found: C, 47.54; H, 5.74; N, 10.98; S, 8.19; Cl, 18.54.

EXAMPLE 114

2-(3-Amino-4-methylstyryl)-5,6,7,8-tetrahydro-4H-thiazolo [5,4-b]azepine dihydrochloride By the method of Example 18, the title compound was obtained by reacting 3-amino-4-methylcinnamic acid, 3-amino-ϵ-caprolactam and phosphorus pentasulfide, purifying and neutralizing with hydrogen chloride.

Yield 11.8%.

m.p. 244–247° (recrystallized from methanol).

IR(KBr)cm$^{-1}$: 3446, 3248, 1604, 1518, 1502, 1445, 1372, 1356, 1309, 956, 883, 818.

NMR(d$_6$—DMSO-D$_2$O)δ: 1.69(4H,m), 2.37(3H,s), 2.82(2H, brs), 3.08(2H,brs), 7.32(2H,d), 7.39(1H,d,J=8.06Hz), 7.60(1H,d), 7.63(1H,s).

Elemental analysis for C$_{16}$H$_{21}$N$_3$SCl$_2$:

Calculated: C, 53.63; H, 5.91; N, 11.73; S, 8.95; Cl, 19.79.
Found: C, 53.47; H, 5.79; N, 11.73; S, 8.95; Cl, 19.54.

EXAMPLE 115

2-[2-(6-Methyl)pyridyl]-5,6,7,8-tetrahydro-4H-thiazolo [5,4-b]azepine hydrochloride By the method of Example 18, the title compound was obtained by reacting 6-methylpicolinic acid, 3-amino-ϵ-caprolactam and phosphorus pentasulfide, purifying and neutralizing with hydrogen chloride.

Yield 40.8%.

m.p 185–188° (recrystallized from methanol).

IR(KBr)cm$^{-1}$: 3444, 3212, 1582, 1567, 1533, 1456, 1370, 1350.

NMR(d$_6$—DMSO-D$_2$O)δ: 1.68(2H,m), 1.80(2H,m), 2.61(3H, s), 2.93(2H,t), 3.12(2H,t), 7.39 (1H,d,J=7.36Hz), 7.87(1H,d,J=7.77Hz), 8.00(1H,t).

Elemental analysis for C$_{13}$H$_{16}$N$_3$SCl:

Calculated: C, 55.41; H, 5.72; N, 14.91; S, 11.38; Cl, 12.58.
Found: C, 55.30; H, 5.64; N, 14.82; S, 11.46; Cl, 12.18.

EXAMPLE 116

2-(3-Cyanophenyl)-5,6,7,8-tetrahydro-4H-thiazolo[5,4-b]azepine

The title compound was obtained by reacting 3-(3-cyanobenzoyl)amino-ϵ-caprolactam and phosphorus pentasulfide in the method described in Example 1.

Yield 41.5%.

m.p. 174° (recrystallized from ethyl acetate).

IR(KBr)cm$^{-1}$: 2914, 2228, 1523, 1483, 1461, 1370, 802.

NMR(CDCl$_3$)δ: 1.67–1.91(4H,m), 2.92–2.98(2H,m), 3.14(2H,t,J=5Hz), 7.45(1H,t,J=7Hz), 7.55(1H,m), 7.96(1H,m), 8.04–8.06 (1H,m).

Elemental analysis for C$_{14}$H$_{13}$N$_3$S:

Calculated: C, 65.85; H, 5.13; N, 16.46; S, 12.56.
Found: C, 65.91; H, 5.05; N, 16.65; S, 12.53.

EXAMPLE 117

2-(4-Cyanophenyl)-5,6,7,8-tetrahydro-4H-thiazolo[5,4-b]azepine

The title compound was obtained by reacting 3-(4-cyanobenzolyamino-ϵ-caprolactam and phosphorus pentasulfide in the method described in Example 1.

Yield 57.3%.

m.p. 163–164° (recrystallized from ethyl acetate).

IR(KBr)cm$^{-1}$: 2222, 1507, 1439, 1373, 1356, 834.

NMR(CDCl$_3$)δ: 1.60–1.91(4H,m), 2.96(2H,t,J=6Hz), 3.15(2H,t,J=5Hz), 4.10(1H,brs),7.63(2H, d,J=8Hz), 7.84(2H,d,J=8Hz).

Elemental analysis for C$_{14}$H$_{13}$N$_3$S:

Calculated: C, 65.85; H, 5.13; N, 16.46; S, 12.56.
Found : C, 66.15; H; 4.93; N, 16.52; S, 12.48.

EXAMPLE 118

2-[2-(4-Imidazolyl)ethenyl]-5,6,7,8-tetrahydro-4H-thiazolo [5,4-b]azepine dihydrochloride The title compound was obtained by reacting imidazole-4-acrylic acid, 3-amino-ϵ-caprolactam and phosphorus pentasulfide in the method described in Example 118.

Yield 12.2%.

m.p. 170–173° (recrystallized from methanol).

IR(KBr)cm$^{-1}$: 3326, 2746, 1597, 1513, 1450, 1375, 1348.

NMR(d$_6$—DMSO—D$_2$O)δ: 1.57–1.92(4H,m), 2.86(2H,m), 3.11(2H,m), 7.25(1H,d,J=16.7Hz), 7.49(1H,d,J=16.7Hz), 7.88(1H,s), 9.17(1H,s).

Elemental analysis for C$_{12}$H$_{16}$N$_4$SCl$_2$·0.5H$_2$O:

Calculated: C, 43.91; H, 5.22; N, 17.07; S, 9.77; Cl, 21.60.
Found: C, 44.08; H, 5.54; N, 17.24; S, 9.66; Cl, 21.23.

EXAMPLE 119

2-(4-Ethoxyformimidoylphenyl)-5,6,7,8-tetrahydro-4H-thiazolo[5,4-b]azepine dihydrochloride A solution (700 ml) of 2-(4-cyanophenyl)-5,6,7,8-tetrahydro-4H-thiazolo[5,4-b]azepine (8.00 g) in ethanol was saturated with hydrogen chloride, and allowed to stand overnight. It was concentrated under reduced pressure, and the residue was washed with ethyl ether and dried to give the title compound as a powder.

Yield 10.9 g, 93%.

m.p. 146° (decomp.).

IR(KBr)cm$^{-1}$: 1592, 1529, 1495, 1443, 1352, 1072.

NMR(d₆—DMSO)δ: 1.40(3H,t,J=7Hz), 1.50–1.90(4H,m), 2.82–2.94(2H,m), 3.01–3.12(2H,m), 4.66(2H,q,J=7Hz), 7.92(2H,d,J=9Hz), 8.18(2H,d,J=9Hz).

EXAMPLE 120

2-(4-Ethoxyformimidoylphenyl)-5,6,7,8-tetrahydro-4H-thiazolo[5,4-b]azepine 2-(4-Ethoxyformimidoylphenyl)-5,6,7,8-tetrahydro-4H-thiazolo[5,4-b]azepine dihydrochloride (1.5 g) was neutralized with an aqueous sodium hydrogen carbonate, and extracted with chloroform. The extract was washed with water, dried and distilled under reduced pressure to remove the solvent. The residue was purified by a column chromatography on silica gel to give the title compound as a powder (yield 1.1 g, 87%).

m.p. 141–143°.

IR(KBr)cm⁻¹: 1625, 1513, 1411, 1370, 1328, 1090.

NMR(CDCl₃)δ: 1.41(3H,t,J=7Hz), 1.57–1.97(4H,m), 2.89–3.01(2H,m), 3.06–3.17(2H,m), 4.32(2H,q,J=7Hz), 7.76(4H,s).

EXAMPLE 121

2-(4-Amidinophenyl)-5,6,7,8-tetrahydro-4H-thiazolo[5,4-b]azepine dihydrochloride A solution (150 ml) of 2-(4-ethoxyformimidoylphenyl)-5,6,7,8-tetrahydro-4H-thiazolo[5,4-b]azepine dihydrochloride (1.3 g) in ethanol was saturated with ammonia and allowed to stand overnight. The resultant precipitate was removed by filtration, and the filtrate was neutralized with hydrogen chloride to give the title compound (yield 0.5 g, 42%).

m.p. 218–220° (recrystallized from a mixture of methanol and ethyl ether).

IR(KBr)cm⁻¹: 3188, 1671, 1596, 1502, 1369, 1450, 1438.

NMR(d₆—DMSO)δ: 1.56–1.83(4H,m), 2.81–2.90(2H,m), 3.01–3.11(2H,m), 7.87(2H,d,J=9Hz), 7.93(2H,d,J=9Hz).

Elemental analysis for $C_{14}H_{16}N_4S \cdot 2HCl$:

Calculated: C, 48.70; H, 5.25; N, 16.23; S, 9.29; Cl, 20.53.

Found : C, 48.34; H, 5.31; N, 16.09; S, 9.05; Cl, 20.31.

EXAMPLE 122

2-(4-N,N-Dimethylamidinophenyl)-5,6,7,8-tetrahydro-4H-thiazolo[5,4-b]azepine trihydrochloride A solution (1.6 ml) of 3.8M dimethylamine in toluene was added to a solution (70 ml) of 2-(4-ethoxyformimidoylphenyl)-5,6,7,8-tetrahydro-4H-thiazolo[5,4-b]azepine (1.6 g) in ethanol, and the whole was stirred for a day at room temperature. The reaction mixture was concentrated, and the residue was washed with ethyl ether and then neutralized with hydrogen chloride to give the title compound (yield 1.4 g, 63%).

m.p. 193–196° (recrystallized from a mixture of methanol and ethyl ether).

IR(KBr)cm⁻¹: 3100, 2464, 2238, 1664, 1625, 1533, 1437.

NMR(d₆—DMSO)δ: 1.49–1.96(4H,m), 2.88–2.97(2H,m), 3.01–3.26(8H,m), 7.69(2H,d,J=8Hz), 8.00(2H,d,J=8Hz).

Elemental analysis for $C_{16}H_{20}N_4S \cdot 3HCl$:

Calculated: C, 46.89; H, 5.66; N, 13.67; S, 7.82; Cl, 25.95.

Found : C, 46.71; H, 5.77; N, 13.36; S, 8.02; Cl, 25.16.

EXAMPLE 123

2-(4-N-Benzylamidinophenyl)-5,6,7,8-tetrahydro-4H-thiazolo[5,4-b]azepine dihydrochloride By the method of Example 122, the title compound was obtained by reacting 2-(4-ethoxyformimidoylphenyl)-5,6,7,8-tetrahydro-4H-thiazolo[5,4-b]azepine and benzylamine, and neutralizing with hydrogen chloride to give the title compound (yield 38%).

m.p. 249–251° (recrystallized from a mixture of methanol and ethyl ether).

IR(KBr)cm⁻¹: 2998, 1667, 1599, 1520, 1497, 1369, 747.

NMR(d₆—DMSO)δ: 1.55–1.90(4H,m), 2.81–2.92(2H,m), 3.01–3.26(2H,m), 4.73(2H,d,J=6Hz), 7.38–7.46(5H,m), 7.88(4H,m).

Elemental analysis for $C_{21}H_{22}N_4S \cdot 2HCl$:

Calculated: C, 57.93; H, 5.56; N, 12.87; S, 7.36; Cl, 16.28.

Found: C, 57.48; H, 5.55; N, 12.76; S, 7.48; Cl, 16.41.

EXAMPLE 124

2-(4-N-Methylamidinophenyl)-5,6,7,8-tetrahydro-4H-thiazolo[5,4-b]azepine dihydrochloride By the method of Example 122, the title compound was obtained by reacting 2-(4-ethoxyformimidoylphenyl)-5,6,7,8-tetrahydro-4H-thiazolo[5,4-b]azepine and a solution of methylamine in methanol, and then neutralized with hydrogen chloride.

Yield 17%.

m.p. 184–186° (recrystallized from a mixture of methanol and ethyl ether).

IR(KBr)cm⁻¹: 3086, 1673, 1631, 1597, 1518, 1372, 1355, 1125.

NMR(d₆—DMSO)δ: 1.50–1.91(4H,m), 2.86–2.97(2H,m), 3.00–3.13(5H,m), 7.88(4H,s).

Elemental analysis for $C_{15}H_{18}N_4S \cdot 2HCl \cdot 0.5H_2O$.

Calculated : C, 48.91; H, 5.75; N, 15.21; S, 8.71; Cl, 19.25.

Found: C, 48.83; H, 5.58; N, 15.29; S, 8.96; Cl, 19.09.

EXAMPLE 125

2-(3-Ethoxyformimidoylphenyl)-5,6,7,8-tetrahydro-4H-thiazolo[5,4-b]azepine

The title compound was obtained from 2-(3-cyanophenyl)-5,6,7,8-tetrahydro-4H-thiazolo[5,4-b]azepine in the method described in Example 119 and Example 120.

Yield 83.1%.

m.p. 141–143°.

IR(KBr)cm⁻¹: 3218, 2928, 1634, 1524, 1370, 1323, 1071.

NMR(CDCl₃)δ: 1.43(3H,t,J=7Hz). 1.51–1.97(4H,m), 2.86–3.19(4H,m), 3.97(1H,br), 4.34(2H, q,J=7Hz), 7.39(1H,t,J=8Hz), 7.68(1H,dt, J=1Hz,8Hz), 7.82(1H,dt,J=1Hz,8Hz), 8.10–8.14(1H,m).

EXAMPLE 126

2-(3-N,N-Dimethylamidinophenyl)-5,6,7,8-tetrahydro-4H-thiazolo[5,4-b]azepine dihydrochloride By the method of Example 122, the title compound was obtained by reacting 2-(3-ethoxyformimidoyl-phenyl)-5,6,7,8-tetrahydro-4H-thiazolo[5,4-b]azepine and a solution of dimethylamine in toluene, and neutralizing the resultant product with hydrogen chloride.

Yield 70%.

m.p. 203–205° (recrystallized from a mixture of methanol and ethyl ether).

IR(KBr)cm$^{-1}$: 3022, 1663, 1631, 1601, 1517, 1373.

NMR(d$_6$—DMSO)δ: 1.56–1.85(4H,m), 2.83–2.91(2H,m), 2.96–3.08(2H,m), 2.99(3H,s), 3.25 (3H,s), 7.52–7.69(2H,m), 7.95–7.99 (2H,m).

Elemental analysis for C$_{16}$H$_{20}$N$_4$S·2HCl·0.5H$_2$O:

Calculated: C, 50.25; H, 6.06; N, 14.65; S, 8.39; Cl, 18.54.

Found: C, 50.59; H, 6.36; N, 14.60; S, 8.46; Cl, 18.43.

EXAMPLE 127

2-(3-N-Methylamidinophenyl)-5,6,7,8-tetrahydro-4H-thiazolo[5,4-b]azepine dihydrochloride By the method of Example 122, the title compound was obtained by reacting 2-(3-ethoxyformimidoylphenyl)-5,6,7,8-tetrahydro-4H-thiazolo[5,4-b]azepine and a solution of methylamine in methanol, and neutralizing with hydrogen chloride.

Yield 54%.

m.p. 205–207° (recrystallized from a mixture of methanol and ethyl ether).

IR(KBr)cm$^{-1}$: 3192, 3054, 1678, 1602, 1515, 1371.

NMR(d$_6$—DMSO)δ: 1.58–1.85(4H,m), 2.84–2.95(2H,m), 3.00–3.10(5H,m), 7.64(1H,t,J=8Hz), 7.73–7.76(1H,m), 8.03–8.11(2H,m).

Elemental analysis for C$_{15}$H$_{18}$N$_4$S·2HCl·0.5H$_2$O:

Calculated: C, 48.91; H, 5.75; N, 15.21; S, 8.71; Cl, 19.25.

Found: C, 48.55; H, 5.66; N, 15.11; S, 8.65; Cl, 19.15.

EXAMPLE 128

2-(5-Benzimidazolyl)-5,6,7,8-tetrahydro-4H-thiazolo[5,4-b]azepine dihydrochloride By the method of Example 1, the title compound was obtained by reacting 3-(5-benzimidazolecarbonyl-)amino-ε-caprolactam and phosphorus pentasulfide, purifying and neutralizing with hydrogen chloride.

Yield 14% m.p. 208–210° (recrystallized from a mixture of methanol and ethyl ether).

IR(KBr)cm$^{-1}$: 2928, 2726, 1605, 1514, 1375, 818.

NMR(d$_6$—DMSO)δ: 1.56–1.86(4H,m), 2.86–2.93(2H,m), 3.02–3.07(2H,m), 7.89(1H,d,J=9Hz), 7.97(1H,dd,J=2Hz,9Hz), 8.18(1H,br.s), 9.66(1H,s).

Elemental analysis for C$_{14}$H$_{14}$N$_4$S·2HCl·H$_2$O:

Calculated: C, 46.54; H, 4.74; N, 15.51; S, 8.88; Cl, 19.63.

Found: C, 46.72; H, 4.92; N, 15.20; S, 8.95; Cl, 19.93.

EXAMPLE 129

2-(3-Pyridyl)-5,6,7,8-tetrahydro-4H-thiazolo[5,4-b]azepine dihydrochloride

By the method of Example 1, the title compound was obtained by reacting 3-nicotinoylamino-ε-caprolactam and phosphorus pentasulfide, purifying and neutralizing with hydrogen chloride.

Yield 66.0%.

m.p. 199–200° (recrystallized from methanol and ethyl ether).

IR(KBr)cm$^{-1}$: 3202, 2730, 2478, 1552, 1499, 1370.

NMR(d$_6$—DMSO)δ: 1.56–1.84(4H,m), 2.84–2.91(2H,m), 3.03–3.08(2H,m), 7.99(1H,dd,J=5Hz, 8Hz), 8.70(1H,dt,J=2Hz,8Hz), 8.76(1H, dd,J=2Hz,5Hz), 9.09(1H,d,J=2Hz).

Elemental analysis for C$_{12}$H$_{13}$N$_3$S·2HCl:

Calculated: C, 47.37; H, 4.97; N, 13.81; S, 10.54; Cl, 23.31.

Found: C, 47.43; H, 4.99; N, 13.95; S, 10.24; Cl, 22.91.

EXAMPLE 130

2-(3-Aminomethyl-4-methylphenyl)-5,6,7,8-tetrahydro-4H-thiazolo[5,4-b]azepine dihydrochloride By the method of Example 18, 3-cyano-4-methylbenzoic acid was reacted with 3-amino-ε-caprolactam and phosphorus pentasulfide to give 2-(3-cyano-4-methylphenyl)-5,6,7,8-tetrahydro-4H-thiazolo[5,4-b]azepine (yield 74.7%).

NMR(CDCl$_3$)δ: 1.71(2H,m), 1.84(2H,m), 2.55(3H,s), 2.94(2H,t), 3.13(2H,t), 7.31(1H,d, J=8.42Hz), 7.84(1H,dd,J=1.93Hz, 8.42Hz), 7.98(1H,d,J=1.93Hz).

Then, a solution of 2-(3-cyano-4-methylphenyl)5,6,7,8-tetrahydro-4H-thiazolo[5,4-b]azepine (6.12 g) and cobalt chloride hexahydrate (10.8 g) in a mixture of methanol (30 ml) and tetrahydrofuran (20 ml) was ice-cooled, followed by adding a powder of sodium borohydride (8.6 g) gradually, and further stirred for 1 hr. at the same temperature. After acidifying with an aqueous 4N-hydrochloric acid, the reaction mixture was extracted with diethyl ether, the aqueous layer was alkalified with an aqueous ammonia and extracted with chloroform. The extract was dried over anhydrous magnesium sulfate and distilled under reduced pressure to remove the solvent. The residue was purified by a column chromatography on silica gel, and neutralized with hydrogen chloride to give the title compound (yield 22.7 %).

m.p. 245–248° (recrystallized from methanol).

IR(KBr)cm$^{-1}$: 3232, 2932, 1608, 1530, 1499, 1447, 1372.

NMR(DMSO)δ: 1.66(2H,m), 1.82(2H,m), 2.40(3H,s), 2.92(2H,brs), 3.09(2H,brs), 4.08 (2H,brs), 5.59(2H,brs), 7.34(1H,d,J=8.06Hz), 7.80(1H,d,J=8.06Hz), 7.89 (1H,s), 8.56(1H,brs).

Elemental analysis for C$_{15}$H$_{21}$N$_3$SCl$_2$·0.5H$_2$O

Calculated: C, 50.70; H, 6.24; N, 11.83; S, 9.02; Cl, 19.95.

Found: C, 50.33; H, 6.02; N, 11.74; S, 9.04; Cl, 19.62.

EXAMPLE 131

2-(4-Cyano-3-methylphenyl)-5,6,7,8-tetrahydro-4H-thiazolo[5,4-b]azepine hydrochloride By the method of Example 18, the title compound was obtained by reacting 4-cyano-3-methylbenzoic acid, 3-amino-ε-caprolactam and phosphorus pentasulfide, purifying and neutralizing with hydrogen chloride, Yield 57.4%.

m.p. 184–186° (recrystallized from methanol).

IR(KBr)cm$^{-1}$: 3208, 2514, 2224, 1593, 1514, 1486, 1459, 1371.

NMR(d$_6$—DMSO)δ: 1.63(2H,m), 1.75(2H,m), 2.51(3H,s), 3.05(2H,t), 5.82(1H,brs), 7.68(1H, dd,J=1.44Hz, 8.16Hz), 7.76(1H,d,J=8Hz), 7.78(1H,s).

Elemental analysis for C$_{15}$H$_{16}$N$_3$SCl:

Calculated: C, 58,91; H, 5,27, N, 13.74; S, 10.48; Cl, 11.59.

Found: C, 58.58; H, 5.22; N, 13.59; S, 10.20; Cl, 11.42.

EXAMPLE 132

2-(4-Aminomethyl-3-methylphenyl)-5,6,7,8-tetrahydro-4H-thiazolo[5,4-b]azepine dihydrochloride A solution of 2-(4-cyano-3-methylphenyl)-5,6,7,8-tetrahydro-4H-thiazolo[5,4-b]azepine (20 g) and cobalt chloride hexahydrate (35.3 g) in a mixture of methanol (90 ml) and tetrahydrofuran (60 ml) was ice-cooled, followed by addition of a powder of sodium borohydride (33.1 g) gradually, and further stirred for 20 hrs. at room temperature. After acidifying with an aqueous 4N-hydrochloric acid, the reaction mixture was extracted with diethyl ether. The aqueous layer was alkalified with an aqueous ammonia and extracted with chloroform. The extract was dried over anhydrous magnesium sulfate, and distilled under reduced pressure The residue was purified by a column chromatogarphy on silica gel, and neutralized with hydrogen chloride to give the title compound (yield 20.1%).

m.p 246-150° (recrystallized from methanol).

IR(KBr)cm$^{-1}$: 3438, 3210, 2936, 1598, 1523, 1493, 1445, 1372.

NMR($d_6$—DMSO): 1.63(2H,m), 1.80(2H,m), 2.41(3H,s), 2.92(2H,br.s), 3.08(2H,br.s), 4.03 (2H,m), 5.60(2H,br.s), 7.51(1H,d, J=8.36Hz), 7.72(2H,m), 8.56(1H,br.s).

Elemental analysis for $C_{15}H_{21}N_3SCl_2$:

Calculated: C, 52.02; H, 6.11; N, 12.13; S, 9.26; Cl, 20.47.

Found: C, 51.93; H, 6.34; N, 11.74; S, 8.98; Cl, 20.25.

EXAMPLE 133

2-(2-Pyridyl)-5,6,7,8-tetrahydro-4H-thiazolo[5,4-b]azepine dihydrochloride

By the method of Example 1, the title compound was obtained by reacting 3-picolinoylamino-ε-caprolactam and phosphorus pentasulfide, purifying and neutralizing with hydrogen chloride.

Yield 57.4% m.p. 181-183° (recrystallized from a mixture of methanol and ethyl ether).

IR(KBr)cm$^{-1}$: 2508, 2356, 1624, 1532, 1464, 777.

NMR($d_6$—DMSO)δ: 1.60-1.89(4H,m), 2.94(2H,t,J=6Hz), 3.09-3.14(2H,m), 7.45-7.52 (1H,m), 8.03(1H, t,J=8Hz), 8.14(1H,d,J=8Hz), 8.56(1H,d,J=5Hz).

Elemental analysis for $C_{12}H_{13}N_3S\cdot 2HCl$:

Calculated: C, 47.37; H, 4.97; N, 13.81; S, 10.54.

Found : C, 47.28; H, 4.93; N, 13.95; S, 10.32.

EXAMPLE 134

2-[4-(4-Methylpiperazinyl)phenyl]-5,6,7,8-tetrahydro-4H-thiazolo[5,4-b]azepine trihydrochloride By the method of Example 1, the title compound was obtained by reacting 3-[4-(4-methylpiperazinyl) benzoyl]amino-ε-caprolactam and phosphorus pentasulfide, purifying and neutralizing with hydrogen chloride.

Yield 17.5% m.p. 176-177° (recrystallized from a mixture of methanol and ethyl ether).

IR(KBr)cm$^{-1}$: 3410, 2698, 1601, 1537, 1398, 1251.

NMR($d_6$—DMSO)δ: 1.57-1.94(4H,m), 2.79(3H,d,J=4Hz), 2.93-2.99(2H,m), 3.03-4.11(10H,m), 7.11(2H,d,J=9Hz), 7.89(2H,d,J=9Hz).

Elemental analysis for $C_{18}H_{24}N_4S\cdot 3HCl\cdot 1.5H_2O$:

Calculated: C, 46.51; H, 6.50; N, 12.05; S, 6.90.

Found : C, 46.76; H, 6.48; N, 12.25; S, 6.72.

EXAMPLE 135

2-(1-Methyl-1H-1,2,3-triazol-4-yl)-5,6,7,8-tetrahydro-4H-thiazolo[5,4-b]azepine hydrochloride By the method of Example 1, the title compound was obtained by reacting 3-(1-methyl-1H-1,2,3-triazolo-4-carbonyl)amino-ε-caprolactam and phosphorus pentasulfide, purifying and neutralizing with hydrogen chloride.

Yield 45.5% m.p. 199-201° (recrystallized from methanol).

IR(KBr)cm$^{-1}$: 3216, 1610 , 1567, 1521, 1495, 1353, 1232.

NMR($d_6$—DMSO)δ: 1.55-1.85(4H,m), 2.81-2.87(2H,m), 3.04-3.11(2H,m), 4.12(3H,s), 9.61 (1H,s).

Elemental analysis for $C_{10}H_{13}N_5S\cdot HCl$:

Calculated: C, 44.19; H, 5.19; N, 25.77; S, 11.80; Cl, 13.05.

Found : C, 44.20; H, 5.12; N, 25.61; S, 11.56; Cl, 12.82.

EXAMPLE 136

2-(Indol-3-yl)-5,6,7,8-tetrahydro-4H-thiazolo[5,4-b]azepine hydrochloride

By the method of Example 1, the title compound was obtained by reacting 3-(indole-3-carbonyl)amino-ε-caprolactam and phosphorus pentasulfide, purifying and neutralizing with hydrogen chloride.

Yield 9.8% m.p. 227-229° (recrystallized from a mixture of methanol and ethyl ether).

IR(KBr)cm$^{-1}$: 3134, 1609, 1495, 1435, 1346, 1241, 740.

NMR($d_6$—DMSO)δ:1.60-1.80(4H,m), 2.91-2.97(2H,m), 3.00-3.10(2H,m), 7.27-7.32(2H,m), 7.56-7.61(1H,m), 7.79-7.84(1H,m), 8.67(1H,d,J=3Hz).

Elemental analysis for $C_{15}H_{15}N_3S\cdot HCl$:

Calculated: C, 58.90; H, 5.27; N, 13.74; S, 10.48; Cl, 11.59.

Found: C, 58.79; H, 5.14; N, 13.63; S, 10.19; Cl, 11.32.

EXAMPLE 137

2-(4-Chloro-3-nitrophenyl)-5,6,7,8-tetrahydro-4H-thiazolo[5,4-b]azepine

The title compound was obtained by reacting 4-chloro-3-nitrobenzoic acid, 3-amino-ε-caprolactam and phosphorus pentasulfide in the method described in Example 18.

Yield 30.7%.

m.p. 116-118° (recrystallized from methanol).

IR(KBr)cm$^{-1}$: 3372, 1562, 1528, 1484, 1440, 1369, 1352, 1339, 1296, 1260.

NMR(CDCl$_3$)δ: 1.71(2H,m), 1.85(2H,m), 2.94(2H,t), 3.15(2H,t), 4.09(1H,br.s), 7.51 (1H,d,J=8.47Hz), 7.86(1H,dd,J=2.17Hz, 8.47Hz), 8.23(1H,d,J=2.17Hz).

Elemental analysis for $C_{13}H_{12}N_3SClO\cdot 0.5H_2O$:

Calculated: C, 48.98; H, 4.11; N, 13.18; Cl, 11.12.

Found C, 49.35; H, 3.84; N, 13.09; Cl, 10.97.

EXAMPLE 138

2-(1-Methyl-2-pyrrolyl)-5,6,7,8-tetrahydro-4H-thiazolo[5,4-b]azepine hydrochloride By the method of Example 18, the title compound was obtained by reacting 1-methyl-2-pyrrolecarboxylic acid, 3-amino-ε-caprolactam and phosphorus pentasulfide, purifying and neutralizing with hydrogen chloride.

Yield 23.1%.

m.p. 193–196° (recrystallized from methanol).

IR(KBr)cm$^{-1}$: 3438, 3204, 1610, 1528, 1484, 1472, 1422, 1363, 1351, 1073.

NMR(d$_6$—DMSO—D$_2$O)δ: 1.70(2H,m), 1.82(2H,m), 2.88 (2H,t), 3.11(2H,t), 3.88(3H,s), 6.20(1H,m), 6.85(1H,m), 7.05(1H,m).

Elemental analysis for C$_{12}$H$_{16}$N$_3$SCl:

Calculated: C, 53.42; H, 5.98; N, 15.57; S, 11.89; Cl, 13.14.

Found C, 53.55; H, 6.06; N, 15.72; S, 12.00; Cl, 12.88.

EXAMPLE 139

2-(1,2-Dimethyl-5-benzimidazolyl)-5,6,7,8-tetrahydro-4H-thiazolo[5,4-b]azepine dihydrochloride By the method of Example 18, the title compound was obtained by reacting 1,2-dimethylbenzimidazole-5-carboxylic acid, 3-amino-ε-caprolactam and phosphorus pentasulfide, purifying and neutralizing with hydrogen chloride.

Yield 13.8%.

m.p. 172–175° (recrystallized from methanol).

IR(KBr)cm$^{-1}$: 3428, 1601, 1523, 1462, 1439, 1373, 1343, 1251.

NMR(d$_6$—DMSO—CDCl$_3$)δ: 1.73(2H,m), 1.88(2H,m), 2.93 (3H,s), 3.02(2H,m), 3.16(2H,m), 4.01(3H,s), 5.07(1H,br.s), 7.98(2H,t,J=9.71Hz), 8.32(1H,s).

Elemental analysis for C$_{16}$H$_{18}$N$_4$S·2HCl·2H$_2$O:

Calculated: C, 47.18; H, 5.94; N, 13.75; S, 7.87; Cl, 17.41.

Found: C, 47.40; H, 5.75; N, 13.79; S, 8.12; Cl, 17.31.

What we claim is:

1. A compound of the formula wherein R$^1$ is (1) a straight, branched or cyclic C$_{1-6}$ alkyl or a straight or branched C$_{2-6}$ alkenyl or alkynyl, each of which is unsubstituted or substituted by one to three substituents selected from the group A1 consisting of hydroxy, C$_{1-3}$ alkoxy, phenoxy, naphthoxy, phenyl-C$_{1-2}$-alkoxy, mercapto, C$_{1-3}$ alkylthio, phenylthio, naphthylthio, phenyl-C$_{1-2}$-alkylthio, amino, mono or di-C$_{1-3}$ alklyamino, halogen, C$_{2-4}$ alkoxycarbonyl, benzyloxycarbonyl, C$_{2-4}$ alkoxycarbonyloxy, formyl, C$_{2-3}$ alkanoyl, benzoyl, C$_{2-5}$ alkanoyloxy, bonylamino, phenyl-lower-alkoxycarbonylamino, pyrrolidino, morpholino, carboxyl, and carbamoyl;

(2) a group of the formula R3CO— wherein R3 is (i) a straight, branched or cyclic C$_{1-18}$ alkyl or a straight or branched C$_{2-6}$ alkenyl or alkynyl, each of which is unsubstituted or substituted by one to three substituents selected from the group A1 as defined above:

(ii) phenyl or naphthyl, each of which is unsubstituted or substituted by one to three substituents selected from the group A2 consisting of halogen; nitro; amino which is unsubstituted or substituted by one or two substituents selected from the group consisting of C$_{1-3}$ alkyl, C$_{2-4}$ alkenyl, C$_{3-8}$ cycloalkyl and phenyl; sulfo; mercapto; hydroxy; sulfoxy; sulfamoyl; C$_{1-6}$ alkyl which is unsubstituted or substituted by amino, di C$_{1-3}$ alkylamino, mono C$_{1-3}$ alkylamino, halogen, hydroxy, cyano or carboxy; C$_{1-6}$ alkoxy which is unsubstituted or substituted by a C$_{1-3}$ alkylthio, benzyloxy, C$_{1-3}$ alkylsulfonamido, or amidino which is unsubstituted or substituted by C$_{1-3}$ alkyl or benzyl; methylenedioxy; alkoxy forminidoyl; C$_{1-3}$ alkylsulfonyl; C$_{1-3}$ alkylsulfonylamino; C$_{2-4}$ alkoxycarbonyl; benzyloxycarbonyl; formyl; C$_{2-3}$ alkanoyl; benzoyl; alkanoyloxy; cyano; phthalimido; alkanoylamino; benzamido; C$_{2-4}$ alkoxycarbonylamino; phenyl lower alkoxycarbonylamino; pyrrolidino; morpholino; carboxy; carbamoyl; and phenyl which is unsubstituted or substituted by a halogen or a methoxy-C$_{1-3}$ alkyl; or (iii) a 5- or 6-membered heterocyclic group B1 containing one to four heteroatoms selected from the group consisting of nitrogen, oxygen and sulfur atoms, or a condensed group D1 selected from the group consisting of indolyl, quinolyl, benzimidazolyl, imidazopyridyl, and thiazolopyridyl, wherein the heterocyclic group B1 and the condensed group D1 are unsubstituted or substituted by one to three substituents selected from the group A3 consisting of amino optionally substituted with C$_{2-10}$ alkanoyl, benzoyl, halogen-substituted C$_{2-4}$ alkanoyl, phenyl or C$_{1-3}$ alkyl; halogen; nitro; sulfo; cyano; hydroxy; carboxy; oxy; C$_{1-10}$ alkyl which may be substituted by phenyl, halogen, amino, hydroxy, carboxy, C$_{1-3}$ alkoxy, C$_{1-3}$ alkylsulfonyl or C$_{1-3}$ dialkylamino; C$_{3-6}$ cycloalkyl; C$_{1-3}$ alkoxy; C$_{2-10}$ alkanoyl; benzoyl; phenyl which may be substituted by halogen, nitro, lower alkyl, lower alkoxy, amino, sulfo, hydroxy or cyano; and C$_{1-10}$ alkylthio which may be substituted by phenyl, halogen, amino, hydroxy, carboxy, C$_{1-3}$ alkoxy, C$_{1-3}$ alkylsulfonyl and di-C1-3 alkylamino; or (3) a C$_{1-3}$ alkylsulfonyl which is unsubstituted or substituted by one to three substituents selected from the group A1 as defined above or a phenylsulfonyl which is unsubstituted or substituted by one to three substituents selected from the group A2 as defined above;

and R$^2$ is (1) a hydrogen atom;

(2) a straight, branched or cyclic C$_{1-6}$ alkyl which is unsubstituted or substituted by one to three substituents selected from the group A1 as defined above;

(3) a straight or branched C$_{2-10}$ alkenyl or alkynyl, each of which is unsubstituted or substituted by one to three substituents selected from the group consisting of:

(i) the group A1 as defined above;

(ii) an oxo group;

(iii) a phenyl which is unsubstituted or substituted by one to three substituents selected from the group A2 as defined above; and (iv) a heterocyclic group B1 or a condensed group D1 as defined above, each of which is unsubstituted or substituted by one to three substituents selected from the group A3 as defined above;

(4) a phenyl or a naphthyl, each of which is unsubstituted or substituted by one to three substituents selected from the group A2 as defined above; or (5) a heterocylic group B1 or a condensed group D1 as defined above, each of which is unsubstituted or substituted by one to three substituents selected from the group A3 as defined above; or a pharmaceutically acceptable salt thereof.

2. A compound of the formula

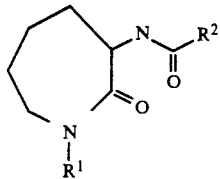

wherein $R^1$ is (1) a hydrogen atom;

(2) a straight, branched or cyclic $C_{1-6}$ alkyl or a straight or branched $C_{2-6}$ alkenyl or alkynyl, each of which is unsubstituted or substituted by one to three substituents selected from the group A1 consisting of hydroxy, $C_{1-3}$ alkoxy, phenoxy, naphthoxy, phenyl-$C_{1-2}$-alkoxy, mercapto, $C_{1-3}$ alkylthio, phenylthio, naphthylthio, phenyl-$C_{1-2}$-alkylthio, amino, mono or di-$C_{1-3}$ alklyamino, halogen, $C_{2-4}$ alkoxycarbonyl, benzyloxycarbonyl, $C_{2-4}$ alkoxycarbonyloxy, formyl, $C_{2-3}$ alkanoyl, benzoyl, $C_{2-5}$ alkanoyloxy, cyano, phthalimido, lower alkanoylamino, benzamido, $C_{2-5}$ alkoxycarbonylamino, phenyl-lower alkoxycarbonylamino, pyrrolidino, morpholino, carboxyl, and carbamoyl;

(3) a group of the formula R3CO- wherein R3 is (i) a straight, branched or cyclic $C_{1-18}$ alkyl or a straight or branched $C_{2-6}$ alkenyl or alkynyl, each of which is unsubstituted or substituted by one to three substituents selected from the group A1 as defined above;

(ii) a phenyl or a naphthyl, each of which is unsubstituted or substituted by one to three substituents selected from the group A2 consisting of halogen; nitro; amino which is unsubstituted or substituted by one or two substituents selected from the group consisting of $C_{1-3}$ alkyl, $C_{2-4}$ alkenyl, $C_{3-8}$ cycloalkyl and phenyl; sulfo; mercapto; hydroxy; sulfoxy; sulfamoyl; $C_{1-6}$ alkyl which is unsubstituted or substituted by amino, di $C_{1-3}$ alkylamino, mono $C_{1-3}$ alkylamino, halogen, hydroxy, cyano or carboxy; $C_{1-6}$ alkoxy which is unsubstituted or substituted by a $C_{1-3}$ alkylthio, benzyloxy, $C_{1-3}$ alkylsulfonamido, or amidino which is unsubstituted or substituted by $C_{1-3}$ alkyl or benzyl; methylenedioxy; alkoxy forminidoyl; $C_{1-3}$ alkylsulfonyl; $C_{1-3}$ alkylsulfonylamino; $C_{2-4}$ alkoxycarbonyl; benzyloxycarbonyl; formyl; $C_{2-3}$ alkanoyl; benzoyl; alkanoyloxy; cyano; phthalimido; alkanoylamino; benzamido; $C_{2-4}$ alkoxycarbonylamino; phenyl lower alkoxycarbonylamino; pyrrolidino; morpholino; carboxy; carbamoyl; and phenyl which is unsubstituted or substituted by a halogen or a methoxy-$C_{1-3}$ alkyl; or (iii) a 5- or 6-membered heterocyclic group B1 containing one to four heteroatoms selected from the group consisting of nitrogen, oxygen and sulfur atoms, or a condensed group D1 selected from the group consisting of indolyl, quinolyl, benzimidazolyl, imidazopyridyl, and thiazolopyridyl, wherein the heterocyclic group B1 and the condensed group D1 are unsubstituted or substituted by one to three substituents selected from the group A3 consisting of amino optionally substituted with $C_{2-10}$ alkanoyl, benzoyl, halogen-substituted $C_{2-4}$ alkanoyl, phenyl or $C_{1-3}$ alkyl; halogen; nitro; sulfo; cyano; hydroxy; carboxy; oxo; $C_{1-10}$ alkyl which may be substituted by phenyl, halogen, amino, hydroxy, carboxy, $C_{1-3}$ alkoxy, $C_{1-3}$ alkylsulfonyl or $C_{1-3}$ dialkylamino; $C_{3-6}$ cycloalkyl; $C_{1-3}$ alkoxy; $C_{2-10}$ alkanoyl; benzoyl; phenyl which may be substituted by halogen, nitro, lower alkyl, lower alkoxy, amino, sulfo, hydroxy or cyano; and $C_{1-10}$ alkylthio which may be substituted by phenyl, halogen, amino, hydroxy, carboxy, $C_{1-3}$ alkoxy, $C_{1-3}$ alkylsulfonyl and di-$C1-3$ alkylamino; or (4) a $C_{1-3}$ alkylsulfonyl which is unsubstituted or substituted by one to three substituents selected from the group A1 as defined above or a phenylsulfonyl which is unsubstituted or substituted by one to three substituents selected from the group A2 as defined above;

and R2 is a branched or cyclic $C_{1-6}$ alkyl which is unsubstituted or substituted by one the three substituents selected from the group A1 as defined above;

or a pharmaceutically acceptable salt thereof.

3. A compound of the formula

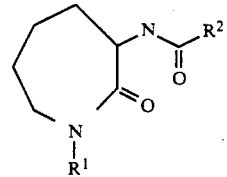

wherein $R^1$ is (1) a hydrogen atom;

(2) a straight, branched or cyclic $C_{1-6}$ alkyl or a straight or branched $C_{2-6}$ alkenyl or alkynyl, each of which is unsubstituted or substituted by one to three substituents selected from the group A1 consisting of hydroxy, $C_{1-3}$ alkoxy, phenoxy, naphthoxy, phenyl-$C_{1-2}$-alkoxy, mercapto, $C_{1-3}$ alkylthio, phenylthio, naphthylthio, phenyl-$C_{1-2}$-alkylthio, amino, mono or di-$C_{1-3}$ alklyamino, halogen, $C_{2-4}$ alkoxycarbonyl, benzyloxycarbonyl, $C_{2-4}$ alkoxycarbonyloxy, formyl, $C_{2-3}$ alkanoyl, benzoyl, $C_{2-5}$ alkanoyloxy, cyano, phthalimido, lower alkanoylamino, benzamido, $C_{2-5}$ alkoxycarbonylamino, phenyl-lower-alkoxycarbonylamino, pyrrolidino, morpholino, carboxyl, and carbamoyl;

(3) a group of the formula R3CO- wherein R3 is (i) a straight, branched or cyclic $C_{1-18}$ alkyl or a straight or branched $C_{2-6}$ alkenyl or alkynyl each of which is unsubstituted or substituted by one to three substituents selected from the group A1 as defined above;

(ii) a phenyl or a naphthyl, each of which is unsubstituted or substituted by one to three substituents selected from the group A2 consisting of halogen; nitro; amino which is unsubstituted or substituted by one or two substituents selected from the group consisting of $C_{1-3}$ alkyl, $C_{2-4}$ alkenyl, $C_{3-8}$ cycloalkyl and phenyl; sulfo; mercapto; hydroxy; sulfoxy; sulfamoyl; $C_{1-6}$ alkyl which is unsubstituted or substituted by amino, di $C_{1-3}$ alkylamino, mono $C_{1-3}$ alkylamino, halogen, hydroxy, cyano or carboxy; $C_{1-6}$ alkoxy which is unsubstituted or substituted by a $C_{1-3}$ alkylthio, benzyloxy, $C_{1-3}$ alkylsulfonamido, or amidino which is unsubstituted or substituted by $C_{1-3}$ alkyl or benzyl; methylenedioxy; alkoxy forminidoyl; $C_{1-3}$ alkylsulfonyl; $C_{1-3}$ alkylsulfonylamino; $C_{2-4}$ alkoxycarbonyl; benzyloxycarbonyl; formyl; $C_{2-3}$ alkanoyl; benzoyl; alkanoyloxy; cyano; phthalimido; alkanoylamino; benzamido; $C_{2-4}$ alkoxycarbonylamino; phenyl lower alkoxycarbonylamino; pyrrolidino; morpholino; carboxy; carbamoyl; and phenyl which is unsubstituted or substituted by a halogen or a methoxy-$C_{1-3}$ alkyl; or (iii) a 5- or 6-membered heterocyclic group B1 containing one to four heteroatoms selected from the group consisting of nitrogen, oxygen and sulfur atoms, or a condensed group D1 selected from the group consisting of indolyl, quinolyl, benzimidazolyl, imidazopyridyl, and thiazolopyridyl, wherein the heterocyclic group B1 and the condensed group D1 are unsubstituted or substituted by one to three substituents selected from the group A3 consisting of amino optionally substituted with $C_{2-10}$ alkanoyl, benzoyl, halogen-substituted $C_{2-4}$ alkanoyl, phenyl or $C_{1-3}$ alkyl; halogen; nitro; sulfo; cyano; hydroxy; carboxy; oxo; $C_{1-10}$ alkyl which may be substituted by phenyl, halogen, amino, hydroxy, carboxy, $C_{1-3}$ alkoxy, $C_{1-3}$ alkylsulfonyl or $C_{1-3}$ dialkylamino; $C_{3-6}$ cycloalkyl; $C_{1-3}$ alkoxy; $C_{2-10}$ alkanoyl; benzoyl; phenyl which may be substituted by halogen, nitro, lower alkyl, lower alkoxy, amino, sulfo, hydroxy or cyano; and $C_{1-10}$ alkylthio which may be substituted by phenyl, halogen, amino, hydroxy, carboxy, $C_{1-3}$ alkoxy, $C_{1-3}$ alkylsulfonyl and di-$C1-3$ alkylamino; or (4) a $C_{1-3}$ alkylsulfonyl which is unsubstituted or substituted by one to three substituents selected from the group A1 as defined above or a phenylsulfonyl which is unsubstituted or substituted by one to three substituents selected from the group A2 as defined above;

and $R^2$ is a straight $C_{1-6}$ alkyl which is substituted by one to three substituents selected from the group consisting of hydroxy, $C_{1-3}$ alkoxy, phenoxy, naphthoxy, phenyl-$C_{1-2}$-alkoxy, mercapto, $C_{1-3}$ alkylthio, phenylthio, naphthylthio, phenyl-$C_{1-2}$-alkylthio, halogen, $C_{2-4}$ alkoxycarbonyl, benzyloxycarbonyl, $C_{2-4}$ alkoxycarbonyloxy, formyl, $C_{2-3}$ alkanoyl, benzoyl, $C_{2-5}$ alkanoyloxy, cyano, phthalimido, pyrrolidino, morpholino, carboxyl, and carbamoyl; or a pharmaceutically acceptable salt thereof.

4. A compound of the formula

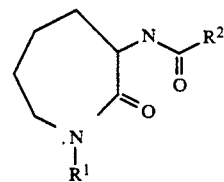

wherein $R^1$ is
(1) a hydrogen atom;
(2) a straight, branched or cyclic $C_{1-6}$ alkyl or a straight or branched $C_{2-6}$ alkenyl or alkynyl, each of which is unsubstituted or substituted by one to three substituents selected from the group A1 consisting of hydroxy, $C_{1-3}$ alkoxy, phenoxy, naphthoxy, phenyl-$C_{1-2}$-alkoxy, mercapto, $C_{1-3}$ alkylthio, phenylthio, naphthylthio, phenyl-$C_{1-2}$-alkylthio, amino, mono or di-$C_{1-3}$ alkylamino, halogen, $C_{2-4}$ alkoxycarbonyl, benzyloxycarbonyl, $C_{2-4}$ alkoxycarbonyloxy, formyl, $C_{2-3}$ alkanoyl, benzoyl, $C_{2-5}$ alkanoyloxy, cyano, phthalimido, lower alkanoylamino, benzamido, $C_{2-5}$ alkoxycarbonylamino, phenyl-lower-alkoxycarbonylamino, pyrrolidino, morpholino, carboxyl, and carbamoyl;
(3) a group of the formula R3CO- wherein R3 is
(i) a straight, branched or cyclic $C_{1-18}$ alkyl or a straight or branched $C_{2-6}$ alkenyl or alkynyl each of which is unsubstituted or substituted by one to three substituents selected from the group A1 as defined above;
(ii) a phenyl or a naphthyl, each of which is unsubstituted or substituted by one to three substituents selected from the group A2 consisting of halogen; nitro; amino which is unsubstituted or substituted by one or two substituents selected from the group consisting of $C_{1-3}$ alkyl, $C_{2-4}$ alkenyl, $C_{3-8}$ cycloalkyl and phenyl; sulfo; mercapto; hydroxy; sulfoxy; sulfamoyl; $C_{1-6}$ alkyl which is unsubstituted or substituted by amino, di $C_{1-3}$ alkylamino, mono $C_{1-3}$ alkylamino, halogen, hydroxy, cyano or carboxy; $C_{1-6}$ alkoxy which is unsubstituted or substituted by a $C_{1-3}$ alkylthio, benzyloxy, $C_{1-3}$ alkylsulfonamido, or amidino which is unsubstituted or substituted by $C_{1-3}$ alkyl or benzyl; methylenedioxy; alkoxy forminidoyl; $C_{1-3}$ alkylsulfonyl; $C_{1-3}$ alkylsulfonylamino; $C_{2-4}$ alkoxycarbonyl; benzyloxycarbonyl; formyl; $C_{2-3}$ alkanoyl; benzoyl; alkanoyloxy; cyano; phthalimido; alkanoylamino; benzamido; $C_{2-4}$ alkoxycarbonylamino; phenyl lower alkoxycarbonylamino; pyrrolidino; morpholino; carboxy; carbamoyl; and phenyl which is unsubstituted or substituted by a halogen or a methoxy-$C_{1-3}$ alkyl; or (iii) a 5- or 6-membered heterocyclic group B1 containing one to four heteroatoms selected from the group consisting of nitrogen, oxygen and sulfur atoms, or a condensed group D1 selected from the group consisting of indolyl, quinolyl, benzimidazolyl, imidazopyridyl, and thiazolopyridyl, wherein the heterocyclic group B1 and the condensed group D1 are unsubstituted or substituted by one to three substituents selected from the group A3 consisting of amino optionally substituted with $C_{2-10}$ alkanoyl, benzoyl, halogen- substituted $C_{2-4}$ alkanoyl, phenyl or $C_{1-3}$ alkyl; halogen, nitro; sulfo; cyano; hydroxy; carboxy; oxo; $C_{1-10}$ alkyl which may be substituted by phenyl, halogen, amino, hydroxy, carboxy, $C_{1-3}$ alkoxy, $C_{1-3}$ alkylsulfonyl or $C_{1-3}$ dialkylamino; $C_{3-6}$ cycloalkyl; $C_{1-3}$ alkoxy; $C_{2-10}$ alkanoyl; benzoyl; phenyl which may be substituted by halogen, nitro, lower alkyl, lower alkoxy, amino, sulfo, hydroxy or cyano; and $C_{1-10}$ alkylthio which may be substituted by phenyl, halogen, amino, hydroxy, carboxy, $C_{1-3}$ alkoxy, $C_{1-3}$ alkylsulfonyl and di-C1-3 alkylamino; or (4) a $C_{1-3}$ alkylsulfonyl which is unsubstituted or substituted by one to three substituents selected from the group A1 as defined above or a phenylsulfonyl which is unsubstituted or substituted by one to three substituents selected from the group A2 as defined above;

and $R^2$ is (1) a hydrogen atom;

(2) a straight or branched $C_{2-10}$ alkenyl or alkynyl, each of which is unsubstituted or substituted by one to three substituents selected from the group consisting of (i) the group A1 as defined above;

(ii) an oxo group;

(iii) a phenyl which is unsubstituted or substituted by one to three substituents selected from the group A2 as defined above; and (iv) a heterocyclic group B1 or a condensed group D1 defined as above, each of which is unsubstituted or substituted by one to three substituents selected from the group A3 as defined above;

(3) a phenyl or a naphthyl, each of which is unsubstituted or substituted by one to three substituents selected from the group A2 as defined above; or (4) a heterocyclic group B1 or a condensed group D1 defined as above, each of which is unsubstituted or substituted by one to three substituents selected from the group A3 as defined above; or a pharmaceutically acceptable salt thereof.

5. A compound as claimed in claim 1, which is 3-(4-methoxybenzoyl) amino-ε-caprolactam.

6. A compound as claimed in claim 1, which is 3-(4-dimethoxybenzoyl) amino-ε-caprolactam.

7. A compound as claimed in claim 1, which is 3-(2,4-dimethoxybenzoyl) amino-ε-caprolactam.

8. A compound as claimed in claim 1, which is 3-(3-methoxybenzoyl) amino-ε-caprolactam.

9. A compound as claimed in claim 1, which is 3-(4-trifluoromethylbenzoyl) amino-ε-caprolactam.

10. A compound as claimed in claim 1, which is 3-(2,3,4-trimethoxy-benzoyl) amino-ε-caprolactam.

11. A compound as claimed in claim 1, which is 3-nicotinoylamino-ε-caprolactam.

* * * * *

UNITED STATES PATENT AND TRADEMARK OFFICE
CERTIFICATE OF CORRECTION

PATENT NO. : 5,300,639

DATED : April 5, 1994

INVENTOR(S) : Tetsuya AONO et al.

It is certified that error appears in the above-identified patent and that said Letters Patent is hereby corrected as shown below:

Column 63,

Claim 1, line 14: delete "bonylamino" and insert therein --cyano, phthalimido, lower alkanoylamino, benzamido, $C_{2-5}$ alkoxycarbonylamino--.

Signed and Sealed this

First Day of November, 1994

*Attest:*

BRUCE LEHMAN

*Attesting Officer*   *Commissioner of Patents and Trademarks*